United States Patent [19]

De

[11] Patent Number: 5,364,869

[45] Date of Patent: Nov. 15, 1994

[54] HETEROCYCLE-SUBSTITUTED BENZYAMINOPYRIDINE ANGIOTENSIN II RECEPTOR ANTAGONISTS

[75] Inventor: Biswanath De, Cincinnati, Ohio

[73] Assignee: Abbott Laboratories, Abbott Park, Ill.

[21] Appl. No.: 1,472

[22] Filed: Jan. 7, 1993

Related U.S. Application Data

[63] Continuation-in-part of Ser. No. 848,618, Mar. 9, 1992, abandoned.

[51] Int. Cl.$^5$ .................. C07D 401/12; C07D 215/42; A61K 31/435
[52] U.S. Cl. ..................... 514/340; 514/256; 514/337; 544/326; 544/328; 544/329; 546/271; 546/274; 546/275; 546/276; 546/304; 548/254; 549/61; 549/474
[58] Field of Search .............. 514/337, 256, 340; 544/328, 329; 546/274, 275, 276, 304, 271

[56] References Cited

U.S. PATENT DOCUMENTS

| | | | |
|---|---|---|---|
| 4,551,468 | 11/1985 | Cross et al. | 546/274 X |
| 4,611,059 | 9/1986 | Sih | 546/274 |
| 4,698,352 | 10/1987 | Narith et al. | 514/339 |
| 5,021,444 | 6/1991 | Trada et al. | 514/337 X |

FOREIGN PATENT DOCUMENTS

| | | | |
|---|---|---|---|
| 0069521 | 1/1983 | European Pat. Off. | 546/274 |
| 0403159 | 12/1990 | European Pat. Off. | 546/274 |
| 0425211 | 5/1991 | European Pat. Off. | 546/274 |
| 0429257 | 5/1991 | European Pat. Off. | 546/274 |
| 0427463 | 6/1991 | European Pat. Off. | 546/274 |
| 0430709 | 6/1991 | European Pat. Off. | 546/274 |
| 0434249 | 6/1991 | European Pat. Off. | 546/274 |
| 0437103 | 7/1991 | European Pat. Off. | 546/274 |
| 0450566 | 10/1991 | European Pat. Off. | 546/274 |
| 0468372 | 1/1992 | European Pat. Off. | 546/274 |
| 475206 | 3/1992 | European Pat. Off. | 514/337 |
| 480204 | 4/1992 | European Pat. Off. | 514/337 |
| 487745 | 6/1992 | European Pat. Off. | 514/337 |
| 499415 | 8/1992 | European Pat. Off. | 514/337 |
| 2118552 | 11/1983 | United Kingdom | 546/274 |

*Primary Examiner*—Floyd D. Higel
*Attorney, Agent, or Firm*—Steven R. Crowley

[57] ABSTRACT

Compounds are disclosed having the formula:

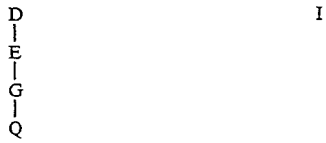

wherein D is a substituted heterocycle, especially substituted pyridyl, E-G is a linking group, especially —N(R$_5$)—CH$_2$—, and Q is a substituted phenyl or substituted heterocyclic group, especially substituted benzothiopene. The compounds of the invention are angiotensin II receptor antagonists.

8 Claims, No Drawings

HETEROCYCLE-SUBSTITUTED BENZYAMINOPYRIDINE ANGIOTENSIN II RECEPTOR ANTAGONISTS

This is a continuation-in-part of U.S. patent application Ser. No. 848,618, filed Mar. 9, 1992 abandoned.

TECHNICAL FIELD

This invention relates to compounds and compositions which block angiotensin II receptors, processes for making such compounds, synthetic intermediates employed in these processes and a method of treating hypertension, edema, renal failure, benign prostatic hypertrophy, diabetic nephropathy, Alzheimer's disease or congestive heart failure with such compounds. The present invention also relates to compositions and a method for treating glaucoma, preventing or treating atherosclerosis, preventing or treating stroke and treatment of a variety of obesity-related disorders with such compounds. The present invention also relates to compositions and a method for treating CNS disorders.

BACKGROUND OF THE INVENTION

Blood pressure is regulated by a multitude of interrelated factors involving neural, vascular and volume-related effects. The renin-angiotensin system (RAS) is one of the important blood pressure regulating systems.

The RAS functions as shown in the scheme below. Low renal perfusion pressure stimulates the juxtaglomerular cells of the kidney to produce the proteolytic enzyme renin. This enzyme acts on a circulating protein, angiotensinogen, cleaving off a decapeptide angiotensin I. Angiotensin I is then cleaved to the octapeptide angiotensin II by angiotensin converting enzyme (ACE). Angiotensin II is the most powerful pressor substance in the RAS. Angiotensin II binds to vascular smooth muscle receptors and induces vasoconstriction, but has little or no stimulating action on the heart.

Saralasin, however, has several disadvantages. Because it is a peptide, saralasin has very poor oral bioavailability. The use of saralasin, therefore, is limited to administration to hospitalized patients by continuous intravenous infusion. Saralasin is also known to cause an initial increase in blood pressure after intravenous administration due to its activity as an angiotensin receptor agonist. Therefore, non-peptidyl angiotensin II receptor antagonists are preferred.

DISCLOSURE OF THE INVENTION

In accordance with the present invention, there are compounds of the formula I:

$$\begin{array}{c} D \\ | \\ E \\ | \\ G \\ | \\ Q \end{array} \quad I$$

wherein
D is

wherein V, W, X, Y and Z are independently selected from N, —N(O)—, CH, $C(R_3)$ and $C(R_4)$,
wherein
(1) 0, 1 or 2 of V, W, X, Y and Z are $C(R_3)$,
(2) 0 or 1 of V, W, X, Y and Z is $C(R_4)$, and
(3) 0, 1, or 3 of V, W, X, Y and Z are N,
    (II) a 5-membered heterocyclic ring comprising 1, 2, 3 or 4 nitrogen atoms or 2 nitrogen atoms and

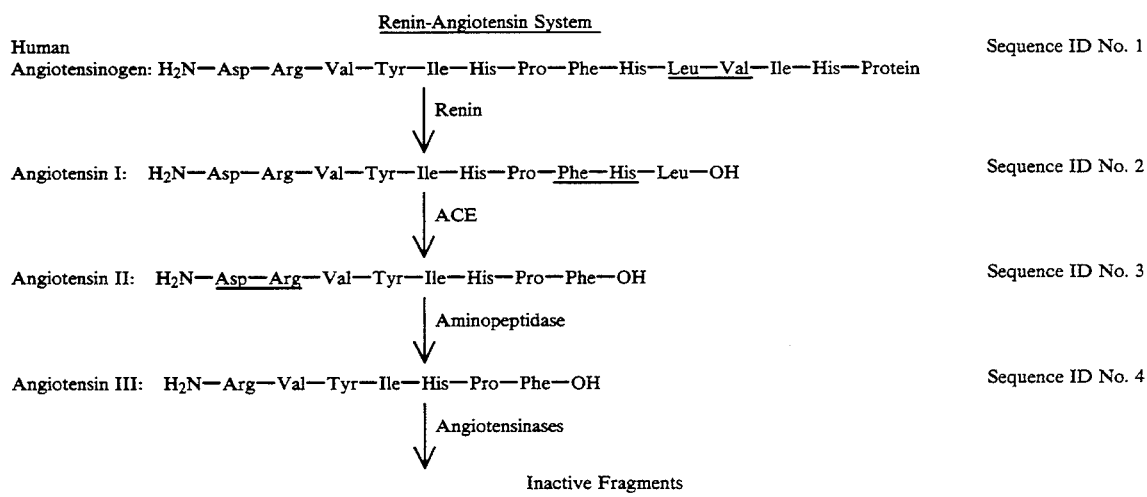

Inhibitors of renin (for example enalkiren) and inhibitors of ACE (for example, captopril and enalapril) have clinical efficacy in treating hypertension and congestive heart failure. ACE inhibitors, however, have reported side effects including cough and skin rash.

Peptidyl and non-peptidyl angiotensin II receptor antagonists are known. The peptidyl compound saralasin or [Sar¹, Ala⁸] angiotensin II has been found to be a potent antagonist of the actions of angiotensin II.

1 oxygen atom or 2 nitrogen atoms and 1 sulfur atom or 1 nitrogen atom and 1 sulfur atom or 1 nitrogen atom and 1 oxygen atom or 1 sulfur atom and 1 oxygen atom or 1 oxygen atom or 1 sulfur atom, the remaining ring atoms being carbon atoms and the 5-membered heterocyclic ring comprising 0, 1 or 2 double bonds; the nitrogen atoms of the 5-membered heterocyclic ring can be substituted with a substituent $R_2$ wherein at each occurrence $R_2$ is independently selected from hydrogen, loweralkyl, carboxy-substituted loweralkyl or alkoxycarbonyl-substituted loweralkyl; one or two carbon atoms of the 5-membered heterocyclic ring can also be substituted with an oxo (=O) substituent and the sulfur atoms of the 5-membered heterocyclic ring can be substituted with one or two oxo (=O) substituents; the nitrogen atoms of the 5-membered heterocyclic ring can be oxidized; the 5-membered heterocyclic ring can also be substituted with one or two substituents independently selected from $R_3$ and $R_4$, $R_3$ being bonded to a carbon atom or a nitrogen atom of the 5-membered heterocyclic ring and $R_4$ being bonded to a carbon atom or a nitrogen atom of the 5-membered heterocyclic ring, (iii) a bicyclic heterocycle comprising a 6-membered ring fused to a 5membered ring, the bicyclic heterocycle comprising at least one heteroatom selected from N, O and S; the 6membered ring of the bicyclic heterocycle comprising 0, 1, 2 or 3 nitrogen atoms or 1 nitrogen atom and 1 oxygen atom or 1 nitrogen atom and 1 sulfur atom or 1 oxygen atom and 1 sulfur atom or 2 oxygen atoms or 2 sulfur atoms or 1 oxygen atom or 1 sulfur atom, the remaining ring atoms being carbon atoms and the 6-membered ring comprising 0, 1, 2 or 3 double bonds; the 5-membered ring of the bicyclic heterocycle comprising 0, 1, 2 or 3 nitrogen atoms or 1 nitrogen and 1 oxygen atom or 1 nitrogen and 1 sulfur atom or 1 oxygen atom and 1 sulfur atom or 1 sulfur atom or 1 oxygen atom, the remaining ring atoms being carbon atoms and the 5-membered ring comprising 0, 1 or 2 double bonds; the nitrogen atoms of the bicyclic heterocycle can be substituted with a substituent $R_2$ wherein at each occurrence $R_2$ is independently selected from hydrogen, loweralkyl, carboxy-substituted loweralkyl or alkoxycarbonyl-substituted loweralkyl; the nitrogen atoms of the bicyclic heterocycle can be oxidized; one or two carbon atoms of the bicyclic heterocycle can be substituted with an oxo (=O) substituent and the sulfur atoms of the bicyclic heterocycle can be substituted with one or two oxo (=O) substituents; the bicyclic heterocycle can be substituted with one, two or three substituents independently selected from $R_3$ and $R_4$, $R_3$ being bonded to a carbon atom or a nitrogen atom of the bicyclic heterocycle and $R_4$ being bonded to a carbon atom or a nitrogen atom of the bicycle heterocycle, (iv) a bicyclic heterocycle comprising a 5-membered ring fused to a 5-membered ring, the bicyclic heterocycle comprising at least one heteroatom selected from N, O and S; each of the 5-membered rings of the bicyclic heterocycle independently comprising 0, 1, 2 or 3 nitrogen atoms or 1 oxygen atom or 1 nitrogen and 1 sulfur atom or 1 oxygen atom and 1 sulfur atom or 1 atom or 1 oxygen atom, the remaining ring atoms being carbon atoms and each of the 5-membered rings independently comprising 0, 1 or 2 double bonds; the nitrogen atoms of the bicyclic heterocycle can be substituted with a substituent $R_2$ wherein at each occurrence $R_2$ is independently selected from hydrogen, loweralkyl, carboxy-substituted loweralkyl or alkoxycarbonyl-substituted loweralkyl; the nitrogen atoms of the bicyclic heterocycle can be oxidized; one or two carbon atoms of the bicyclic heterocycle can be substituted with an oxo (=O) substituent and the sulfur atoms of the bicyclic heterocycle can be substituted with one or two oxo (=O) substituents; the bicyclic heterocycle can be substituted with one or two substituents independently selected from $R_3$ and $R_4$, $R_3$ being bonded to a carbon atom or a nitrogen atom of the bicyclic heterocycle and $R_4$ being bonded to a carbon atom or a nitrogen atom of the bicyclic heterocycle,

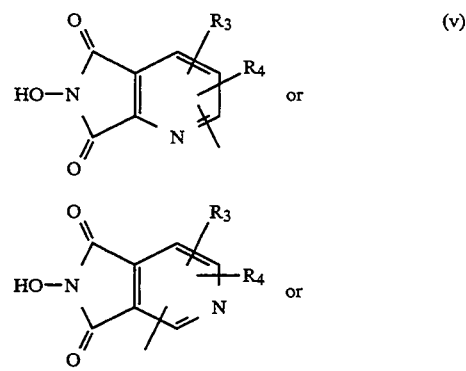

(vi) a bicyclic heterocycle comprising a 6-membered ring fused to another 6-membered ring, the bicyclic heterocycle comprising at least one heteroatom selected from N, O and S; each of the 6-membered rings of the bicyclic heterocycle independently comprising 0, 1, 2 or 3 nitrogen atoms or 1 nitrogen atom and 1 oxygen atom or 1 nitrogen atom and 1 sulfur atom or 1 oxygen atom and 1 sulfur atom or 2 oxygen atoms or 2 sulfur atoms or 1 oxygen atom or 1 sulfur atom, the remaining ring atoms being carbon atoms and each of the 6-membered rings of the bicyclic heterocycle comprising 0, 1, 2 or 3 double bonds; the nitrogen atoms of the bicyclic heterocycle can be substituted with a substituent $R_2$ wherein at each occurrence $R_2$ is independently selected from hydrogen, loweralkyl, carboxy-substituted loweralkyl or alkoxycarbonyl-substituted loweralkyl; the nitrogen atoms of the bicyclic heterocycle can be oxidized; one or two carbon atoms of the bicyclic heterocycle can be substituted with an oxo (=O) substituent and the sulfur atoms of the bicyclic heterocycle can be substituted with one or two oxo (=O) substituents; the bicyclic heterocycle can be substituted with one, two or three substituents independently selected from $R_3$ and $R_4$, $R_3$ being bonded to a carbon atom or a nitrogen atom of the bicyclic heterocycle and $R_4$ being bonded to a carbon atom or a nitrogen atom of the bicyclic heterocycle, E-G is
(i) —N($R_5$)—,
(ii) —O—,
(iii) —S—,
(iv) —N($R_5$)—CH($R_5$)—,
(v) —O—CH($R_5$)—,
(vi) —S—CH($R_5$)—, (vii) —C(R₅')(R₅)—CH(R₅)—,
(viii) —CH(R₅)—C(R₅')(R₅)—,
(ix) —CH(R₅)—N(R₅)—,
(x) —CH(R₅)—O—,
(xi) —CH(R₅)—S—,
(xii) —N(R₅)—N(R₅)—,
(xiii) —N(R₅)—C(O)—,
(xiv) —C(O)—N(R₅)—,
(xiii) —C(R₅)═C(R₅)— or
(xiv) —CH(R₅)—C(R₅')(R₅)—N(R₅)— wherein at each occurrence R₅ is independently selected from hydrogen, loweralkyl, alkoxy-substituted loweralkyl, halo-substituted loweralkyl, carboxy-substituted loweralkyl, heterocyclic-substituted loweralkyl, alkenyl, alkynyl, cycloalkyl or cycloalkylalkyl and R₅' is hydrogen, halo, hydroxy, carboxy, alkoxy or thioalkoxy; and Q is (i)

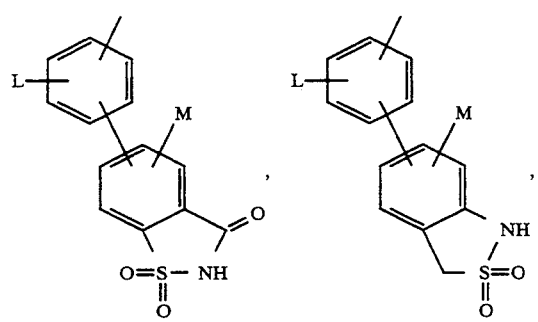

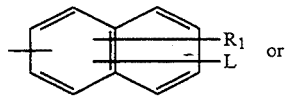

(iii)

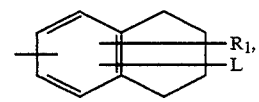

(iv)

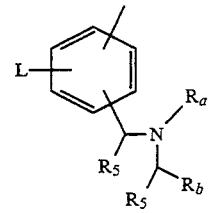

wherein

R_a is —COOR₂₄ or —CH₂COOR₂₄ wherein R₂₄ is hydrogen or a carboxy-protecting group or R_a is tetrazolyl or

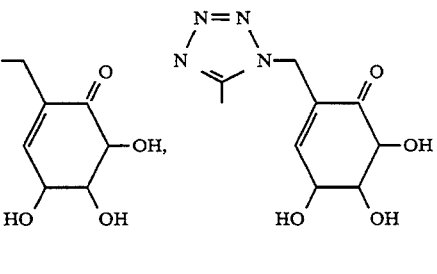

or

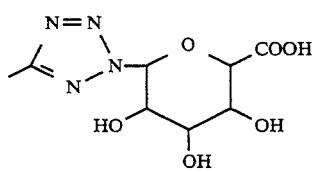

and R_b is loweralkyl or aryl, (ii)

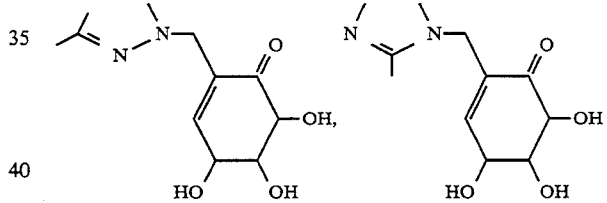

(v)

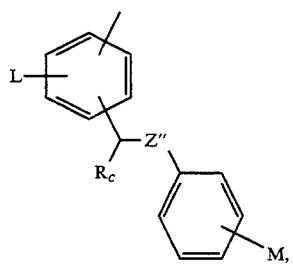

-continued

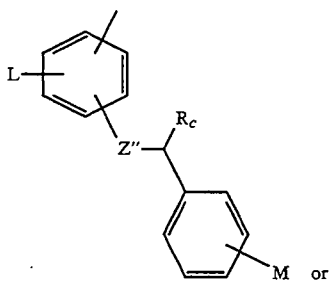

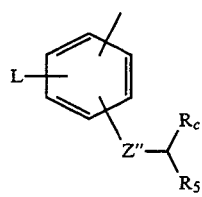

wherein
Z" is O, S or —N(R$_5$)—, R$_5$ is defined as above, R$_c$ is —COOR$_{24}$ or —CH$_2$COOR$_{24}$ wherein R$_{24}$ is hydrogen or a carboxy-protecting group or R$_c$ is tetrazolyl or

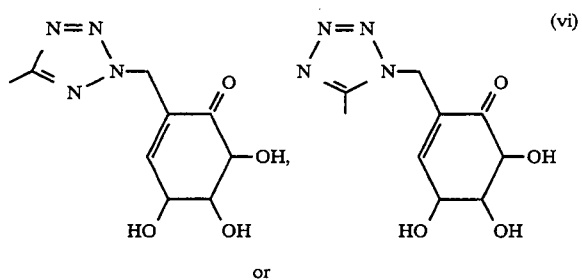

(vi)

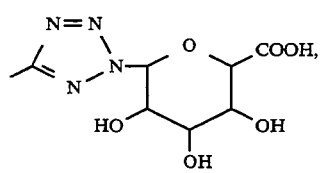

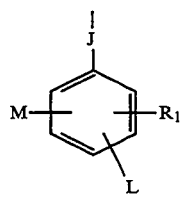

where J is (1) a 5-membered heterocyclic ring comprising 1, 2, 3 or 4 nitrogen atoms or 2 nitrogen atoms and 1 oxygen atom or 2 nitrogen atoms and 1 sulfur atom or 1 nitrogen atom and 1 sulfur atom or 1 nitrogen atom and 1 oxygen atom or 1 sulfur atom and 1 oxygen atom or 1 oxygen atom or 1 sulfur atom, the remaining ring atoms being carbon atoms and the 5-membered heterocyclic ring comprising 0, 1 or 2 double bonds; the nitrogen atoms of the 5-membered heterocyclic ring can be substituted with a substituent R$_2$ wherein at each occurrence R$_2$ is independently selected from hydrogen, loweralkyl, carboxy-substituted loweralkyl or alkoxycarbonyl-substituted loweralkyl; one or two carbon atoms of the 5-membered heterocyclic ring can also be substituted with an oxo (=O) substituent and the sulfur atoms of the 5-membered heterocyclic ring can be substituted with one or two oxo (=O) substituents; the nitrogen atoms of the 5-membered heterocyclic ring can be oxidized; the 5-membered heterocyclic ring can also be substituted with one or two substituents independently selected from R$_3$ and R$_4$, R$_3$ being bonded to a carbon atom or a nitrogen atom of the 5-membered heterocyclic ring and R$_4$ being bonded to a carbon atom or a nitrogen atom of the 5-membered heterocyclic ring,
or J is (2)

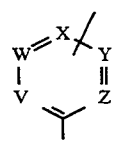

wherein
V, W, X, Y and Z are independently selected from N, —N(O)—, CH, C(R$_3$) and C(R$_4$), wherein
(1) 0, 1 or 2 of V, W, X, Y and Z are C(R$_3$),
(2) 0 or 1 of V, W, X, Y and Z is C(R$_4$), and
(3) 0, 1, 2 or 3 of V, W, X, Y and Z are N,
or J is (3) a bicyclic heterocyclic ring comprising a 6-membered ring fused to a 5-membered ring, the bicyclic heterocycle comprising at least one heteroatom selected from N, O and S; the 6-membered ring of the bicyclic heterocycle comprising 0, 1, or 3 nitrogen atoms or 1 nitrogen atom and 1 oxygen atom or 1 nitrogen atom and 1 sulfur atom or 1 oxygen atom and 1 sulfur atom or 2 oxygen atoms or 2 sulfur atoms or 1 oxygen atom or 1 sulfur atom, the remaining ring atoms being carbon atoms and the 6-membered ring comprising 0, 1, 2 or 3 double bonds; the 5-membered ring of the bicyclic heterocycle comprising 0, 1, 2 or 3 nitrogen atoms or 1 nitrogen and 1 oxygen atom or 1 nitrogen and 1 sulfur atom or 1 oxygen atom and 1 sulfur atom or 1 sulfur atom or 1 oxygen atom, the remaining ring atoms being carbon atoms and the 5-membered ring comprising 0, 1 or 2 double bonds; the nitrogen atoms of the bicyclic heterocycle can be substituted with a substituent R$_2$ wherein at each occurrence R$_2$ is independently selected from hydrogen, loweralkyl, carboxy-substituted loweralkyl or alkoxycarbonyl-substituted loweralkyl; the nitrogen atoms of the bicyclic heterocycle can be oxidized; one or two carbon atoms of the bicyclic heterocycle can be substituted with an oxo(=O) substituent and the sulfur atoms of the bicyclic heterocycle can be substituted with one or two oxo (=O) substituents; the bicyclic heterocycle can be substituted with one, two or three substituents independently selected from R$_1$, R$_3$ and R$_4$, R$_1$, R$_3$ and R$_4$ being bonded to a carbon atom or a nitrogen atom of the bicyclic heterocycle,
or J is (4) a bicyclic heterocyclic ring comprising a 6-membered ring fused to another 6-membered ring, the bicyclic heterocycle comprising at least one heteroatom selected from N, O and S; each of the 6-membered rings of the bicyclic heterocycle independently comprising 0, 1, 2 or 3 nitrogen atoms or 1 nitrogen atom and 1 oxygen atom or 1 nitrogen atom and 1 sulfur atom or 1 oxygen atom and 1 sulfur atom or 2 oxygen atoms or 2 sulfur atoms or 1 oxygen atom or 1 sulfur atom, the remaining ring atoms being carbon atoms and each of the 6-membered rings of the bicyclic heterocycle comprising 0, 1, 2 or 3 double bonds; the nitrogen atoms of the bicyclic heterocycle can be substituted with a substituent $R_2$ wherein at each occurrence $R_2$ is independently selected from hydrogen, loweralkyl, carboxy-substituted loweralkyl or alkoxycarbonyl-substituted loweralkyl; the nitrogen atoms of the bicyclic heterocycle can be oxidized; one or two carbon atoms of the bicyclic heterocycle can be substituted with an oxo ($=$O) substituent and the sulfur atoms of the bicyclic heterocycle can be substituted with one or two oxo ($=$O) substituents; the bicyclic heterocycle can be substituted with one, two or three substituents independently selected from $R_1$, $R_3$ and $R_4$, $R_1$, $R_3$ and $R_4$ being bonded to a carbon atom or a nitrogen atom of the bicyclic heterocycle, (vii) a 5-membered heterocyclic ring comprising 1, 2, 3 or 4 nitrogen atoms or 2 nitrogen atoms and 1 oxygen atom or 2 nitrogen atoms and 1 sulfur atom or 1 nitrogen atom and 1 sulfur atom or 1 nitrogen atom and 1 oxygen atom or 1 sulfur atom and 1 oxygen atom or 1 oxygen atom and 1 sulfur atom, the remaining ring atoms being carbon atoms and the 5-membered heterocyclic ring comprising 0, 1 or 2 double bonds; the nitrogen atoms of the 5-membered heterocyclic ring can be substituted with a substituent $R_2$ wherein at each occurrence $R_2$ is independently selected from hydrogen, loweralkyl, carboxyl-substituted loweralkyl or alkoxycarbonyl-substituted loweralkyl; one or two carbon atoms of the 5-membered heterocyclic ring can also be substituted with an oxo ($=$O) substituent and the sulfur atoms of the 5-membered heterocyclic ring can be substituted with one or two oxo ($=$O) substituents; the nitrogen atoms of the 5-membered heterocyclic ring can be oxidized; the 5-membered heterocyclic ring can also be substituted with one or two substituents independently selected from $R_3$ and $R_4$, $R_3$ being bonded to a carbon atom or a nitrogen atom of the 5-membered heterocyclic ring and $R_4$ being bonded to a carbon atom or a nitrogen atom of the 5-membered heterocyclic ring,

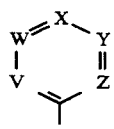
(viii)

wherein

V, W, X, Y and Z are independently selected from N, —N(O)—, CH, C($R_3$) and C($R_4$), wherein (1) 0, 1 or 2 of V, W, X, Y and Z are C($R_3$),
(2) 0 or 1 of V, W, X, Y and Z is C($R_4$), and
(3) 0, 1, 2 or 3 of V, W, X, Y and Z are N, (ix) a bicyclic heterocyclic ring comprising a 6-membered ringfused to a 5-membered ring, the bicyclic heterocycle comprising at least heteroatom selected from N, O and S; the 6-membered ring of the bicyclic heterocycle comprising 0, 1, 2 or 3 nitrogen atoms or 1 nitrogen atom and 1 oxygen atom or 1 nitrogen atom and 1 sulfur atom or 1 oxygen atom and 1 sulfur atom or 2 oxygen atoms or 2 sulfur atoms or 1 oxygen atom or 1 sulfur atom, the remaining ring atoms being carbon atoms and the 6-membered ring comprising 0, 1, 2 or 3 double bonds; the 5-membered ring of the bicyclic heterocycle comprising 0, 1, 2 or 3 nitrogen atoms or 1 nitrogen and 1 oxygen atom or 1 nitrogen and 1 sulfur atom or 1 oxygen atom and 1 sulfur atom or 1 sulfur atom or 1 oxygen atom, the remaining ring atoms being carbon atoms and the 5-membered ring comprising 0, 1 or 2 double bonds; the nitrogen atoms of the bicyclic heterocycle can be substituted with a substituent $R_2$ wherein at each occurrence $R_2$ is independently selected from hydrogen, loweralkyl, carboxy-substituted loweralkyl or alkoxycarbonyl-substituted loweralkyl; the nitrogen atoms of the bicyclic heterocycle can be oxidized; one or two carbon atoms of the bicyclic heterocycle can be substituted with an oxo ($=$O) substituent and the sulfur atoms of the bicyclic heterocycle can be substituted with one or two oxo ($=$O) substituents; the bicyclic heterocycle can be substituted with one, two or three substituents independently selected from $R_1$, $R_3$ and $R_4$, $R_1$, $R_3$ and $R_4$ being bonded to a carbon atom or a nitrogen atom of the bicyclic heterocycle, (x) a bicyclic heterocyclic ring a 6-membered ring fused to another 6-membered ring, the bicyclic heterocycle comprising at least one heteroatom selected from N, O and S; each of the 6-membered rings of the bicyclic heterocycle independently comprising 0, 1, 2 or 3 nitrogen atoms or 1 nitrogen atom and 1 oxygen atom or 1 nitrogen atom and 1 sulfur atom or 1 oxygen atom and 1 sulfur atom or 2 oxygen atoms being carbon atoms and each of the 6-membered rings of the bicyclic heterocycle comprising 0, 1, 2 or 3 double bonds; the nitrogen atoms of the bicyclic heterocycle can be substituted with a substituent $R_2$ wherein at each occurrence $R_2$ is independently selected from hydrogen, loweralkyl, carboxy-substituted loweralkyl or alkoxycarbonyl-substituted loweralkyl; the nitrogen atoms of the bicyclic heterocycle can be oxidized; one or two carbon atoms of the bicyclic heterocycle can be substituted with an oxo ($=$O) substituent and the sulfur atoms of the bicyclic heterocycle can be substituted with one or two oxo ($=$O) substituents; the bicyclic heterocycle can be substituted with one, two or three substituents independently selected from $R_1$, $R_3$ and $R_4$, $R_1$, $R_3$ and $R_4$ being bonded to a carbon atom or a nitrogen atom of the bicyclic heterocycle,

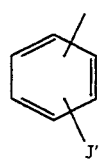
(xi)

wherein j' is (1) a 5-membered heterocyclic ring comprising 1, 2, 3 or 4 nitrogen atoms or 2 nitrogen atoms and 1 oxygen atom or 2 nitrogen atoms and 1 sulfur atom or 1 nitrogen atom and 1 sulfur atom and or 1 nitrogen atom and 1 oxygen atom or 1 sulfur atom and 1 oxygen atom or 1 oxygen atom or 1 sulfur atom, the remaining ring atoms being carbon atoms and the 5-membered heterocyclic ring comprising 0, 1 or 2 double bonds; the nitrogen atoms of the 5-membered heterocyclic ring can be substituted with a substituent $R_2$ wherein at each occurrence $R_2$ is independently selected from hydrogen, loweralkyl, carboxy-substituted loweralkyl or alkoxycarbonyl-substituted loweralkyl; one or two carbon atoms of the 5-membered heterocyclic ring can also be substituted with an oxo (=O) substituent and the sulfur atoms of the 5-membered heterocyclic ring can be substituted with one or two oxo (=O) substituents; the nitrogen atoms of the 5-membered heterocyclic ring can be oxidized; the 5-membered heterocycle ring can also be substituted with one or two substituents independently selected from $R_3$ and $R_4$, $R_3$ being bonded to a carbon atom or a nitrogen atom of the 5-membered heterocyclic ring and $R_4$ being bonded to a carbon atom or a nitrogen atom of the 5-membered heterocyclic ring, or j' is (2)

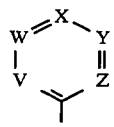

wherein
V, W, X, Y and Z are independently selected from N, —N(O)—, CH, C($R_3$) and C($R_4$), wherein
(1) 0, 1 or 2 of V, W, X, Y and Z are C($R_3$),
(2) 0 or 1 of V, W, X, Y and Z is C($R_4$), and
(3) 0, 1, 2 or 3 or V, W, X, Y and Z are N, or j' is (3) a bicyclic heterocyclic ring comprising a 6-membered ring fused to a 5-membered ring, the bicyclic heterocycle comprising at least one heteroatom selected from N, O and S; the 6-membered ring of the bicyclic heterocycle comprising 0, 1, 2 or 3 nitrogen atoms or 1 nitrogen atom and 1 oxygen atom or 1 nitrogen atom and 1 sulfur atom or 1 oxygen atom and 1 sulfur atom or 2 oxygen atoms or 2 sulfur atoms or 1 oxygen atom or 1 sulfur atom, the remaining ring atoms being carbon atoms and the 6-membered ring comprising 0, 1, 2 or 3 double bonds; the 5-membered ring of the bicyclic heterocycle comprising 0, 1, 2 or 3 nitrogen atoms or 1 nitrogen and 1 oxygen atom or 1 nitrogen and 1 sulfur atom or 1 oxygen atom and 1 sulfur atom or 1 sulfur atom or 1 oxygen atom, the remaining ring atoms being carbon atoms and the 5-membered ring comprising 0, 1 or 2 double bonds; the nitrogen atoms of the bicyclic heterocycle can be substituted with a substituent $R_2$ wherein at each occurrence $R_2$ is independently selected from hydrogen, loweralkyl, carboxy-substituted loweralkyl or alkoxycarbonyl-substituted loweralkyl; the nitrogen atoms of the bicyclic heterocycle can be oxidized; one or two carbon atoms of the bicyclic heterocycle can be substituted with an oxo (=O) substituent and the sulfur atoms of the bicyclic heterocycle can be substituted with one or two oxo (=O) substituents; the bicyclic heterocycle can be substituted with one, two or three substituents independently selected from $R_1$, $R_3$ and $R_4$, $R_1$, $R_3$ and $R_4$ being bonded to a carbon atom or a nitrogen atom of the bicyclic heterocycle, or J'is (4) a bicyclic heterocyclic ring comprising a 6-membered ring fused to another 6-membered ring, the bicyclic heterocycle comprising at least one heteroatom selected from N, O and S; each of the 6-membered rings of the bicyclic heterocycle independently comprising 0, 1, 2 or 3 nitrogen atoms or 1 nitrogen atom and 1 oxygen atom or 1 nitrogen atom and 1 sulfur atom or 1 oxygen atom and 1 sulfur atom or 2 oxygen atoms or 2 sulfur atoms or 1 oxygen atom or 1 sulfur atom, the remaining ring atoms being carbon atoms and each of the 6-membered rings of the bicyclic heterocycle comprising 0, 1, 2 or 3 double bonds; the nitrogen atoms of the bicyclic heterocycle can be substituted with a substituent $R_2$ wherein at each occurrence $R_2$ is independently selected from hydrogen, loweralkyl, carboxy-substituted loweralkyl or alkoxycarbonyl-substituted loweralkyl; the nitrogen atoms of the bicyclic heterocycle can be oxidized; one or two carbon atoms of the bicyclic heterocycle can be substituted with an oxo (=O) substituent and the sulfur atoms of the bicyclic heterocycle can be substituted with one or two oxo (=O) substituents; the bicyclic heterocycle can be substituted with one, two or three substituents independently selected from $R_1$, $R_3$ and $R_4$, $R_1$, $R_3$ and $R_4$ being bonded to a carbon atom or a nitrogen atom of the bicyclic heterocycle, or

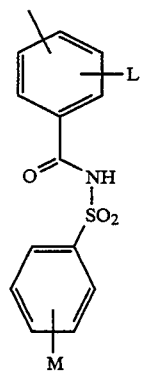

(xii)

or

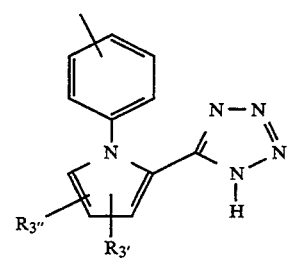

(xiii)

or

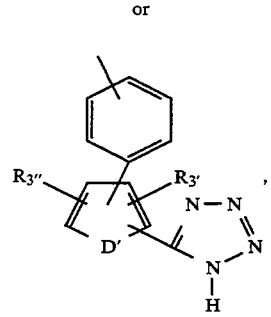

wherein
D' is O, S or N(R₃'") wherein R₃'" is hydrogen or loweralkyl and at each occurrence R₃, R₃' and R₃" are independently selected from
(i) hydrogen,
(ii) loweralkyl,
(iii) halo,
(iv) halo-substituted loweralkyl,
(v) thioalkoxy,
(vi) alkoxy-substituted loweralkyl,
(vii) thioalkoxy-substituted loweralkyl,
(viii) aryl,
(ix) arylalkyl,
(x) —NO₂,
(xi) —COOR₈ wherein R₈ is hydrogen or a carboxy-protecting group,
(xii)

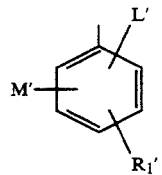

(xiii) —OR₉ wherein R₉ is hydrogen, loweralkyl, halo-substituted loweralkyl, aryl, arylalkyl, heterocyclic-substituted loweralkyl or —C(O)R₁₀ wherein R₁₀ is loweralkyl, halo-substituted loweralkyl, —PO₃H₂ or —NR₁₁R₁₂ wherein R₁₁ and R₁₂ are independently selected from hydrogen and loweralkyl and (xiv) —NR₁₃R₁₄ or —CH₂NR₁₃R₁₄ wherein R₁₃ and R₁₄ are independently selected from (1) hydrogen, (2) lower alkyl, (3) arylalkyl, (4) —C(O)R₁₅, (5) —S(O)₂R₁₅ wherein R₁₅ is loweralkyl or halo-substituted loweralkyl and (6) —R₁₆—R₁₇ wherein R₁₆ is alkylene and R₁₇ is (a)—NR₁₈R₁₉ wherein R₁₈ and R₁₉ are independently selected from hydrogen and loweralkyl or (b) unsubstituted or loweralkyl substituted aziridinyl, azetidinyl, pyrrolidinyl, piperidinyl, piperazinyl, morpholinyl, thiomorpholinyl, pyridinyl or pyrimidinyl, or R₁₃ and R₁₄ taken together with the nitrogen atom to which they are attached form a 5- to 7-membered aliphatic heterocycle and at each occurrence R₄ is independently selected from
(i) hydrogen,
(ii) loweralkyl,
(iii) halo-substituted loweralkyl,
(iv) —CN,
(v) —NO₂,
(vi) —NH₂,
(vii) —NH—C(=N(R₂₅ₐ))(R₂₆ₐ) wherein R₂₅ₐ is hydrogen, —CN, or —NO₂ and R₂₆ₐ is hydrogen, loweralkyl, alkylamino, dialkylamino, alkoxy or thioalkoxy,
(viii) —NH(R₂₆ᵦ) wherein R₂₆ᵦ is a 5-membered aromatic heterocyclic ring wherein the heterocyclic ring contains 1, 2, 3 or 4 nitrogen atoms or 1 nitrogen atom and 1 oxygen atom or 2 nitrogen atoms and 1 oxygen atom or 1 oxygen atom and 1 sulfur atom and wherein the 5-membered heterocyclic ring is unsubstituted or substituted with a substituent selected from amino, alkylamino, dialkylamino, hydroxy, alkoxy, thioalkoxy, halo, loweralkyl and halo-substituted loweralkyl,
(ix) —CHO or —CH(=N—OH),
(x) tetrazolyl,
(xi) —NHS(O)₂R₂₀ or —CH₂NHS(O)₂R₂₀ or —NHC(O)R₂₁ or —N(OH)C(O)R₂₁ or —CH₂NHC(O)R₂₁ or CH₂N(OH)C(O)R₂₁ wherein R₂₀ is loweralkyl, halo-substituted loweralkyl or —NR₂₇ₐR₂₇ᵦ wherein R₂₇ₐ and R₂₇ᵦ are independently selected from hydrogen, —OH and loweralkyl and R₂₁ is loweralkyl, halo-substituted loweralkyl, amino, alkylamino, dialkylamino or —COOH,
(xii) —CH(OH)R₂₂ or —C(O)R₂₂ wherein R₂₂ is loweralkyl, halo-substituted loweralkyl, —CF₂COOR₂₃ or —CH₂COOR₂₃ wherein R₂₃ is hydrogen or a carboxy-protecting group,
(xiii) —COOR₂₄ or —CH₂COOR₂₄ wherein R₂₄ is hydrogen or a carboxy-protecting group,
(xiv) —C(O)NR₂₅R₂₆ or —CH₂C(O)NR₂₅R₂₆ or —NHC(O)NR₂₅R₂₆ or —CH₂NHC(O)NR₂₅R₂₆ or —NHC(S)NR₂₅R₂₆
or —CH₂NHC(S)NR₂₅R₂₆ wherein R₂₅ and R₂₆ are independently selected from hydrogen, loweralkyl, hydroxy, alkoxy, hydroxy-substituted loweralkyl, alkoxy-substituted loweralkyl, alkoxy-substituted alkoxy and —S(O)₂R₂₈ₐ wherein R₂₈ₐ is loweralkyl or aryl, or R₂₅ and R₂₆ taken together with the nitrogen atom to which they are attached form a 5- to 7-membered aliphatic heterocycle;
(xv) —CH₂OR₂₇ wherein R₂₇ is selected from hydrogen, loweralkyl and —C(O)R₂₈ wherein R₂₈ is hydrogen, loweralkyl or aryl;
(xvi) —CH₂NR₂₉R₃₀ wherein R₂₉ is selected from hydrogen, loweralkyl, —C(O)R₃₁, —C(O)NR₃₁R₃₂ and —S(O)₂R₃₃ wherein R₃₁ is selected from hydrogen, loweralkyl and aryl and R₃₃ is selected from loweralkyl and halo-substituted loweralkyl and wherein R₃₀ and R₃₂ are independently selected from loweralkyl, hydroxy and alkoxy;
(xvii) —SO₃H, —OSO₃H or —CH₂SO₃H,
(xviii) —OPO₃H, —PO₃H₂ or —CH₂PO₃H₂,
(xix) —SO₂NR₂₅R₂₆ or —CH₂SO₂NR₂₅R₂₆ wherein R₂₅ and R₂₆ are defined as above;
(xx) —C(O)NHSO₂R₅₉, —C(O)NHC(O)R₅₉ or —C(O)NHNHSO₂R₅₉ wherein R₅₉ is loweralkyl, halo-substituted loweralkyl or aryl; and
(xxi) —CH=C(R_d)(R_e) or —CH₂—C(R_d)(R_e)(R_f) or —CH₂C(O)NHCH(R_g) (R_h) wherein R_d is —COOH or tetrazolyl or

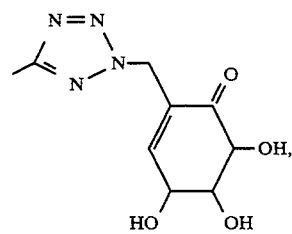

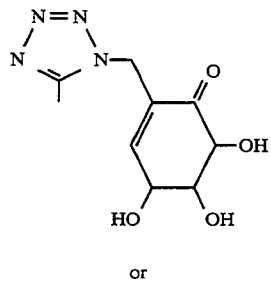

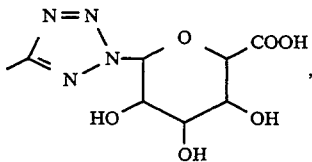

$R_e$ is thienylmethyl, $R_f$ is loweralkyl, $R_g$ is thienyl and $R_h$ is —COOH, L, L', M and M' are independently selected from
(i) hydrogen,
(ii) loweralkyl,
(iii) halo-substituted loweralkyl,
(iv) halo,
(v) —CN,
(vi) —NO$_2$,
(vii) —OH,
(viii) hydroxy-substituted loweralkyl,
(ix) alkoxy-substituted loweralkyl,
(x) —NH$_2$,
(xi) alkylamino,
(xii) dialkylamino,
(xiii) —SH,
(xiv) alkoxy and
(xv) thioalkoxy; and $R_1$ and $R_1'$ are independently selected from
(i) tetrazolyl,

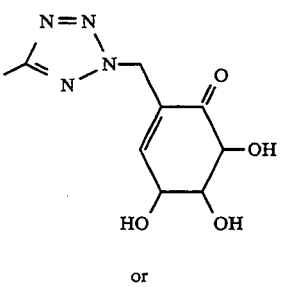

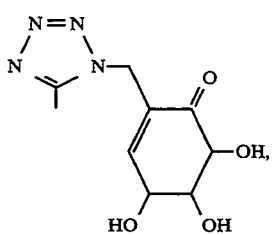

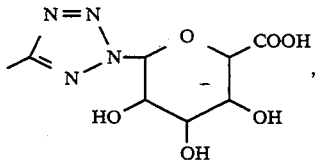

(iv) —NH—C(=N($R_{50a}$))($R_{51a}$) wherein $R_{50a}$ is hydrogen, —CN or —NO$_2$ and $R_{51a}$ is hydrogen, loweralkyl, alkylamino, dialkylamino, alkoxy or thioalkoxy, (v) —NH($R_{51b}$) wherein $R_{51b}$ is a 5-membered aromatic heterocyclic ring wherein the heterocyclic ring contains 1, 2, 3 or 4 nitrogen atoms or 1 nitrogen atom and 1 oxygen atom or 2 nitrogen atoms and 1 oxygen atom or 1 oxygen atom and 1 sulfur atom and wherein the 5-membered heterocyclic ring is unsubstituted or substituted with a substituent selected from amino, alkylamino, dialkylamino, hydroxy, alkoxy, thioalkoxy, halo, loweralkyl and halo-substituted loweralkyl, (vi) —COOR$_6$ or —CH$_2$COOR$_6$ wherein $R_6$ is hydrogen or a carboxy-protecting group or (vii) —NHS(O)$_2$R$_7$ or —CH$_2$NHS(O)$_2$R$_7$ or —NHC(O)R$_{7a}$ or —CH$_2$NHC(O)R$_{7a}$ wherein $R_7$ is loweralkyl, halo-substituted loweralkyl or —NR$_{7b}$R$_{7c}$ wherein $R_{7b}$ and $R_{7c}$ are independently selected from hydrogen and loweralkyl and $R_{7a}$ is loweralkyl, halo-substituted loweralkyl, amino, alkylamino, dialkylamino or —COOH;

(viii) —C(O)NR$_{50}$R$_{51}$ or —CH$_2$C(O)NR$_{50}$R$_{51}$ or —NHC(O)NR$_{50}$R$_{51}$ or —CH$_2$NHC(O)NR$_{50}$R$_{51}$ or —NHC(S)NR$_{50}$R$_{51}$ or —CH$_2$NHC(S)NR$_{50}$R$_{51}$ wherein $R_{50}$ and $R_{51}$ are independently selected from hydrogen, loweralkyl, hydroxy, alkoxy, hydroxy-substituted loweralkyl, alkoxy-substituted loweralkyl, alkoxy-substituted alkoxy and —S(O)$_2$R$_{50a}$ wherein $R_{50a}$ is loweralkyl or aryl, or $R_{50}$ and $R_{51}$ taken together with the nitrogen atom to which they are attached form a 5- to 7-membered aliphatic heterocycle;

(ix) —CH$_2$OR$_{52}$ wherein $R_{52}$ is selected from hydrogen, loweralkyl, and —C(O)R$_{53}$ wherein $R_{53}$ is hydrogen, loweralkyl, or aryl;

(x) —CH(OH)R$_{52a}$ or —C(O)R$_{52a}$ wherein $R_{52a}$ is loweralkyl, halo-substituted loweralkyl, —CF$_2$COOR$_{53a}$ or —CH$_2$COOR$_{53a}$ wherein $R_{53a}$ is hydrogen or a carboxy-protecting group, (xii) —CH$_2$NR$_{54}$R$_{55}$ wherein $R_{54}$ is selected from hydrogen, loweralkyl, —C(O)R$_{56}$, —C(O)NR$_{56}$R$_{57}$ and —S(O)$_2$R$_{58}$ wherein $R_{56}$ is selected from hydrogen, loweralkyl and aryl and $R_{58}$ is selected from lower alkyl and halo-substituted loweralkyl and wherein $R_{55}$ and $R_{57}$ are independently selected from hydrogen, loweralkyl, hydroxy and alkoxy;

(xiii) —N($R_5$)CH($R^{}$)$R_{58a}$ or —OCH($R^{}$)$R_{58a}$ or —SCH($R^{}$)$R_{58a}$ wherein $R_5$ is independently defined as above, $R^{}$ is hydrogen, loweralkyl or aryl and $R_{58a}$ is —COOR$_{24}$ wherein $R_{24}$ is independently defined as above or $R_{58a}$ is tetrazolyl or

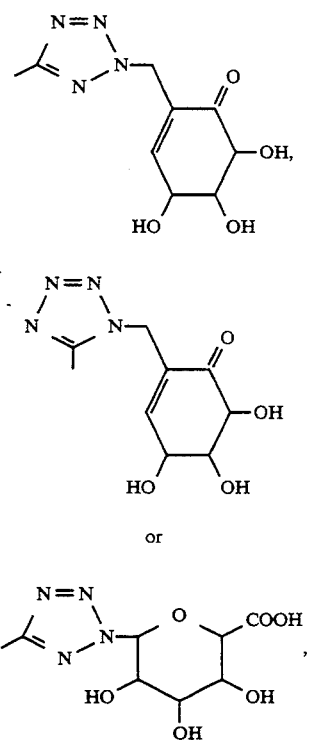

(xiv) —SO$_3$H, —OSO$_3$H or —CH$_2$SO$_3$H,
(xv) —OPO$_3$H$_2$, —PO$_3$H$_2$ or —CH$_2$PO$_3$H$_2$,
(xvi) —SO$_2$NR$_{50}$R$_{51}$ or —CH$_2$SO$_2$NR$_{50}$R$_{51}$ wherein R$_{50}$ and R$_{51}$ are defined as above and
(xvii) —C(O)NHSO$_2$R$_{60}$, —C(O)NHC(O)R$_{60}$ or —C(O)NHNHSO$_2$R$_{60}$ wherein R$_{60}$ is loweralkyl, halo-substituted loweralkyl or aryl; or a pharmaceutically acceptable salt or prodrug thereof.

Preferred compounds of the invention are compounds wherein Q is

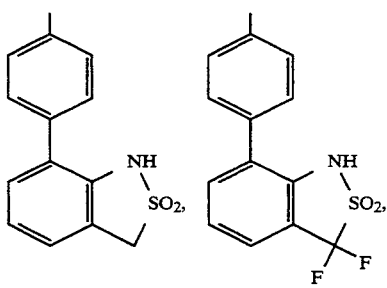

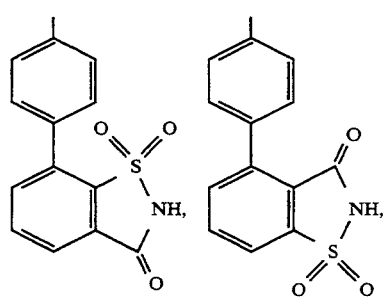

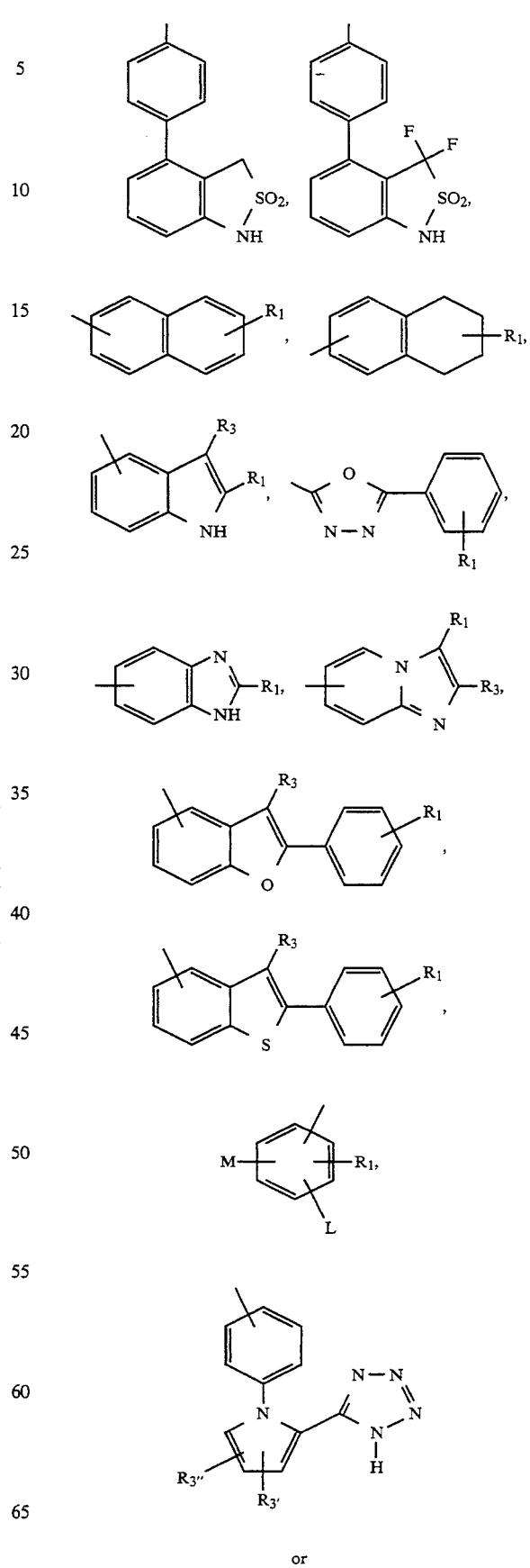

or

-continued
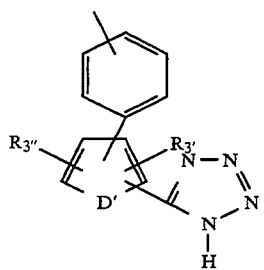
and the like.
Preferred compounds of the invention are compounds wherein D is
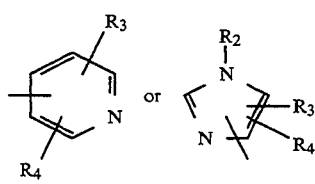
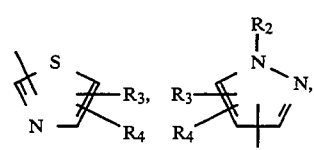
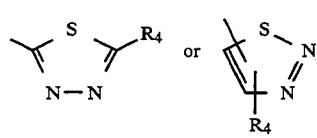
or
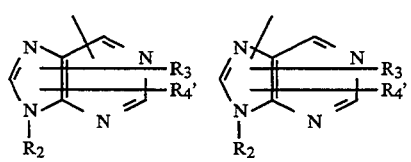
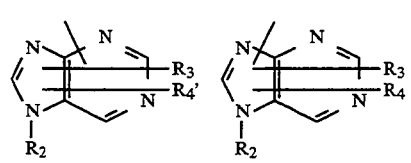
or
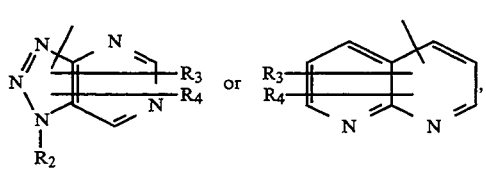
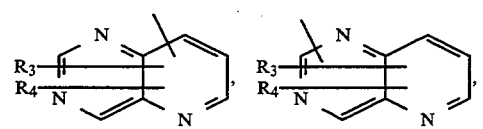
-continued
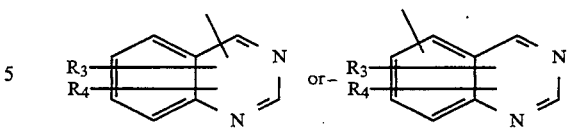
and the like.
Preferred compounds of the invention are compounds wherein —G—E— is —CH$_2$—N(R$_5$)— wherein R$_5$ is defined as above.
More preferred compounds of the invention are compounds of the formula:
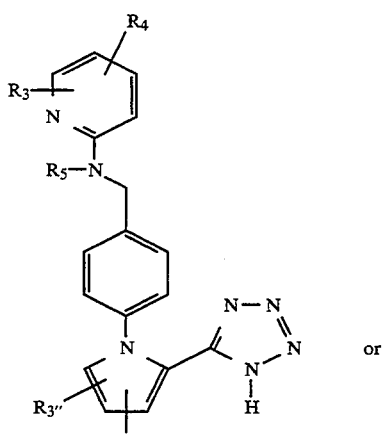
or
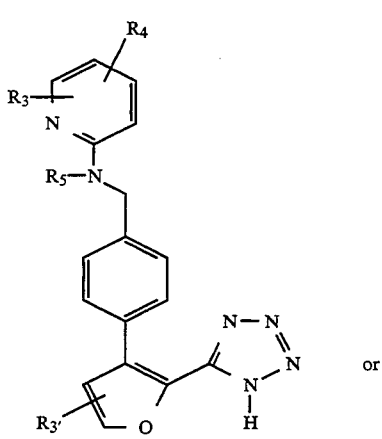
or
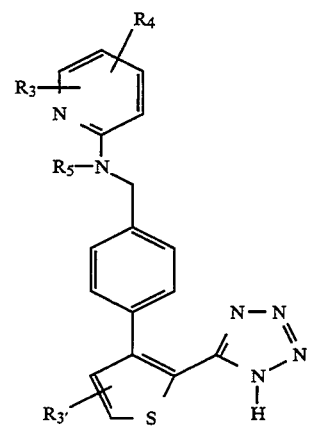
wherein R$_3$, R$_{3'}$, R$_{3''}$, R$_4$ and R$_5$ are defined as above.

Even more preferred compounds of the invention are compounds of the formula:

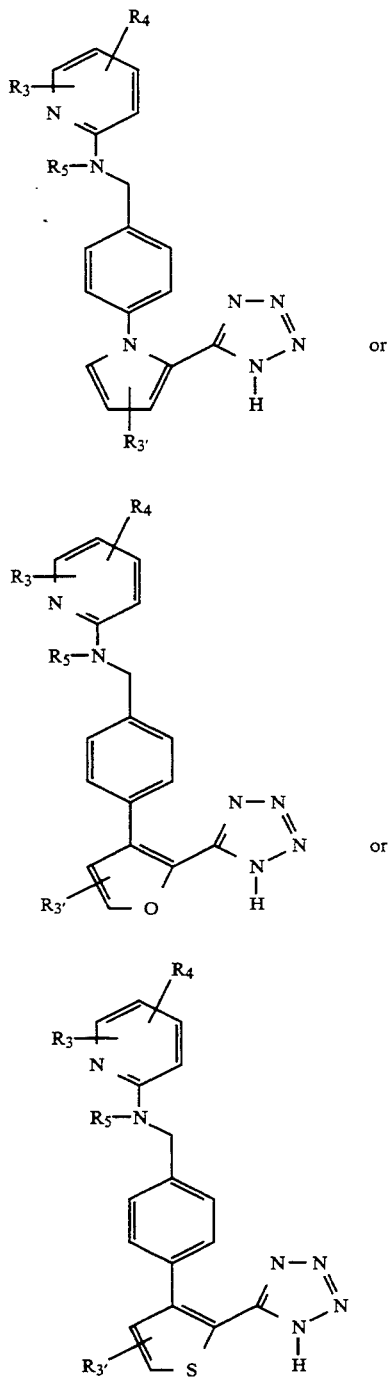

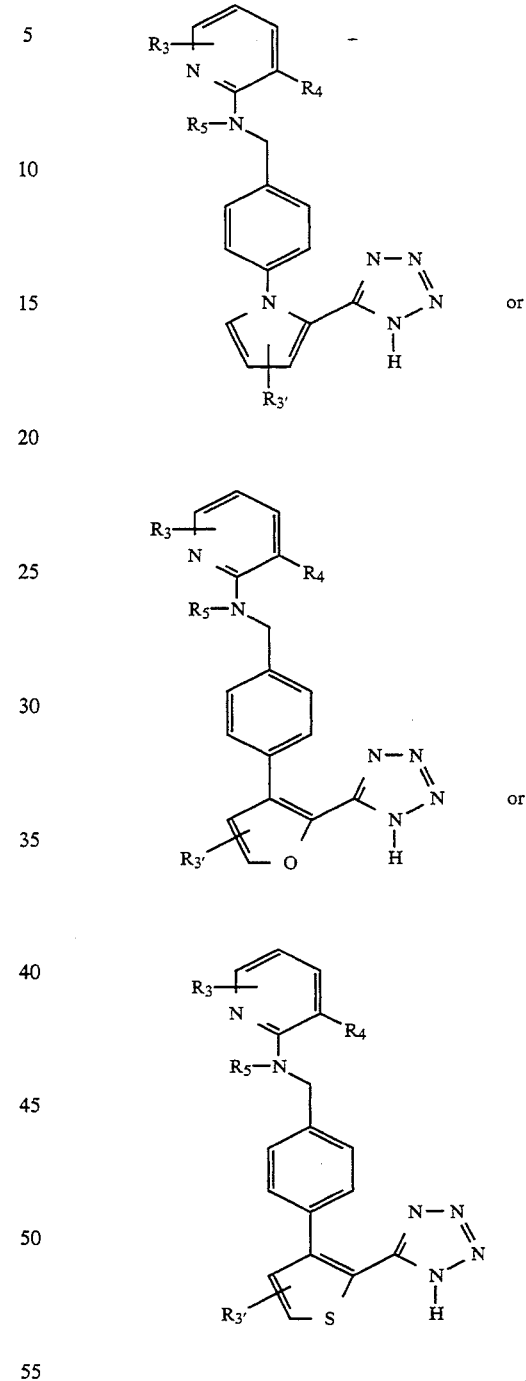

wherein $R_3$ is hydrogen, loweralkyl, halo or alkoxy, $R_{3'}$ is hydrogen, loweralkyl or halo, $R_4$ is —$COOR_{24}$ wherein $R_{24}$ is hydrogen or a carboxy-protecting group and $R_5$ is hydrogen, loweralkyl, alkoxy-substituted loweralkyl, halo-substituted loweralkyl, alkenyl, alkynyl, cycloalkyl or cycloalkylalkyl.

Even more highly preferred compounds of the invention are compounds of the formula:

wherein $R_3$ is hydrogen, loweralkyl, halo or alkoxy, $R_{3'}$ is hydrogen, loweralkyl or halo, $R_4$ is —$COOR_{24}$ wherein $R_{24}$ is hydrogen or a carboxy-protecting group and $R_5$ is hydrogen, loweralkyl, alkoxy-substituted loweralkyl, halo-substituted loweralkyl, alkenyl, alkynyl, cycloalkyl or cycloalkylalkyl.

Most preferred compounds of the invention are compounds of the formula:

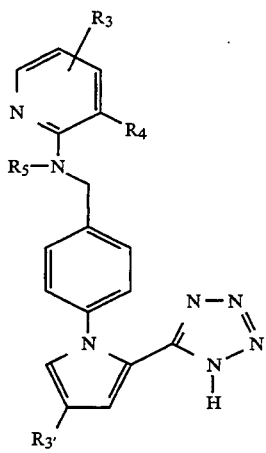
wherein R₃ is hydrogen, halo or alkoxy, R₃' is hydrogen, loweralkyl or halo, R₄ is —COOH and R₅ is loweralkyl.
Representative heterocyclic substituents D and Q are:
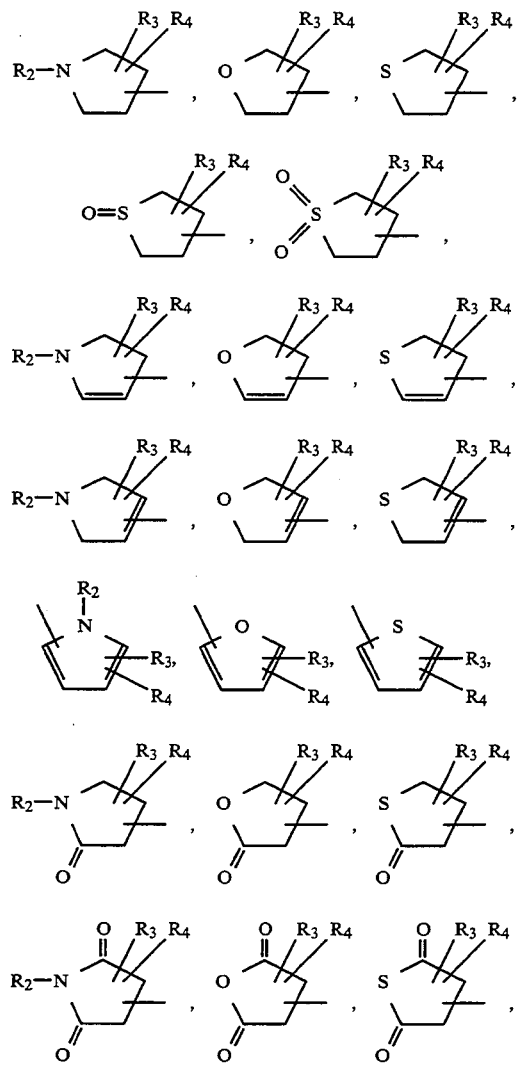
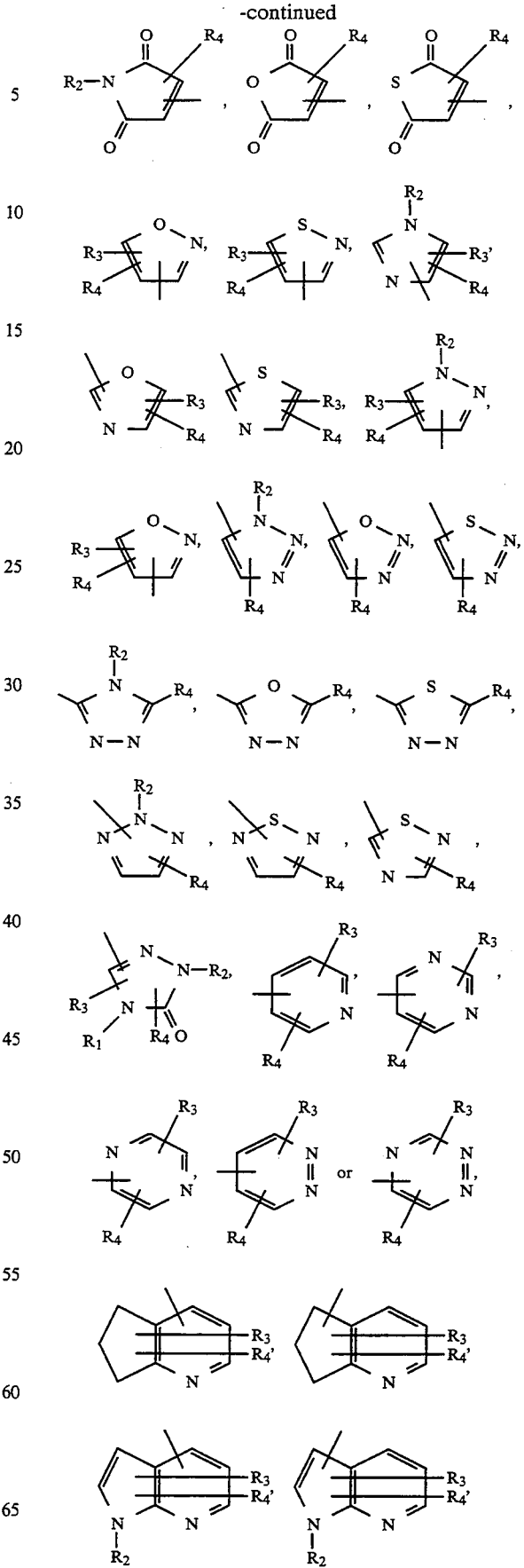

-continued
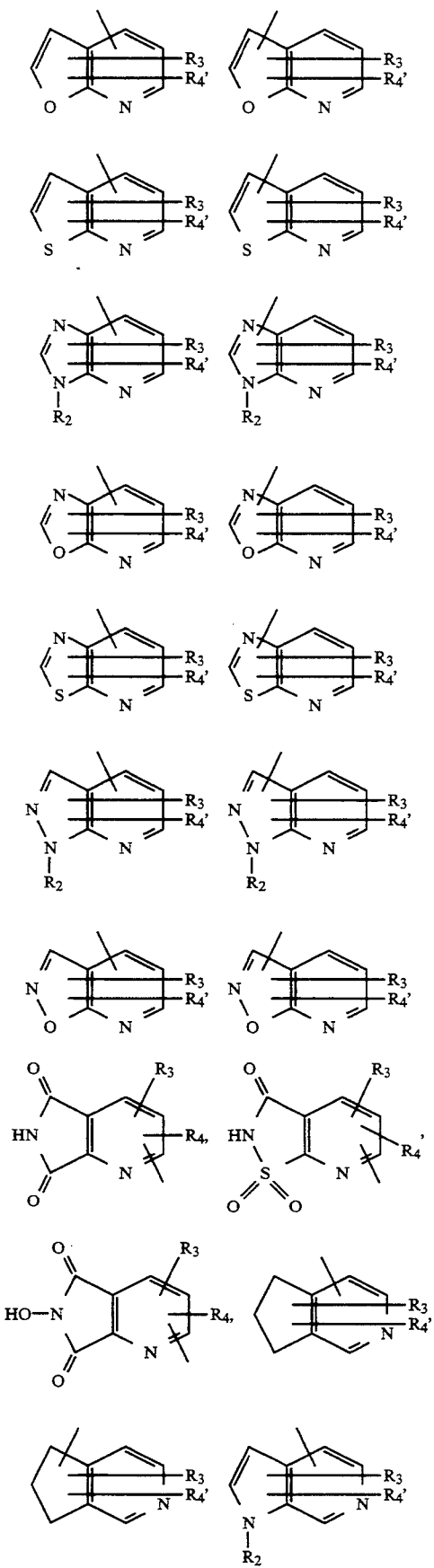
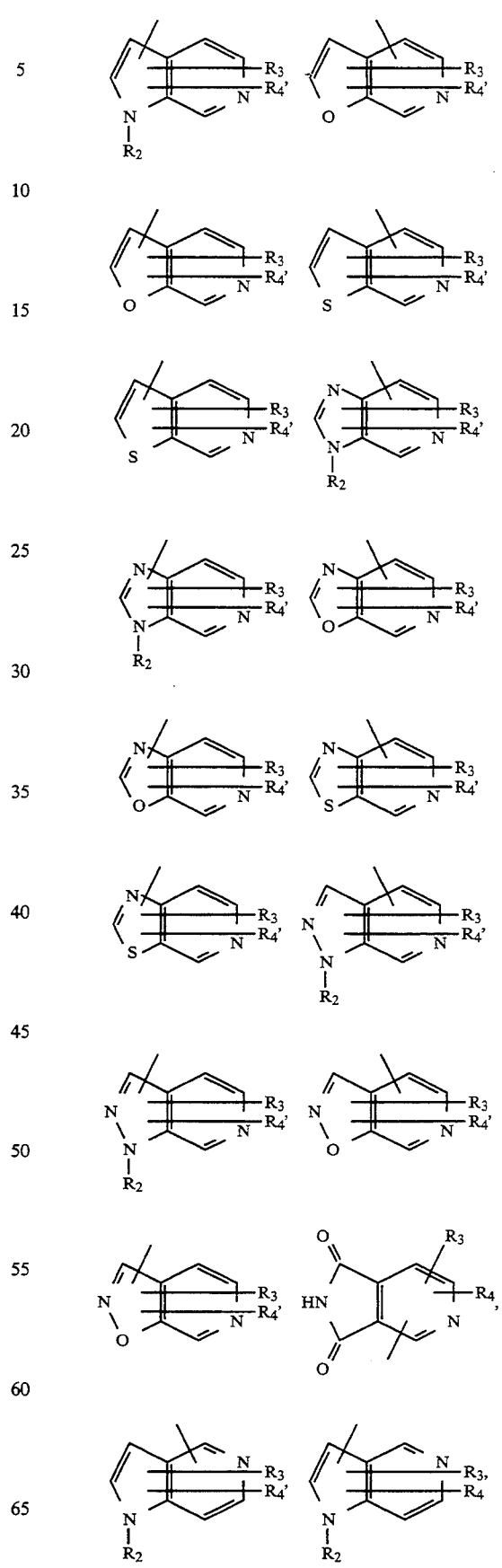

-continued
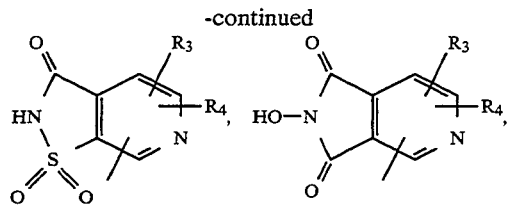
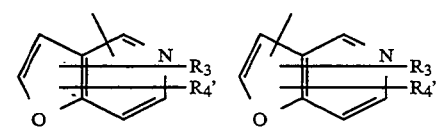
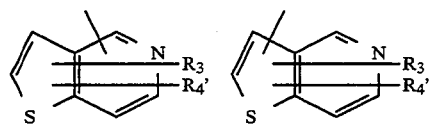
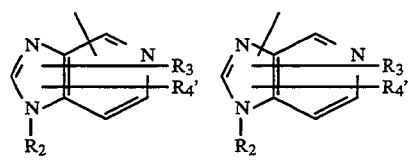
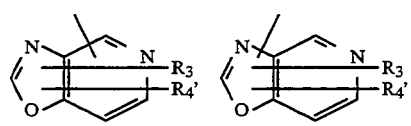
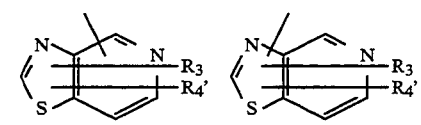
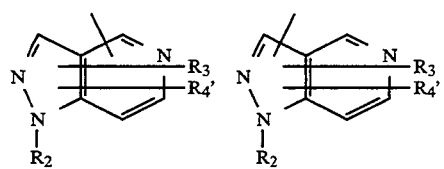
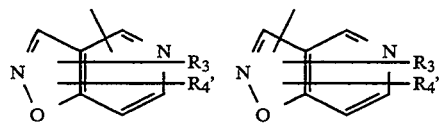
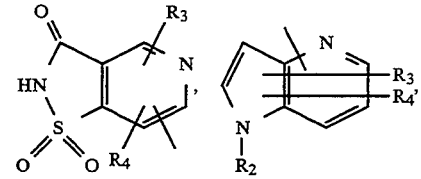
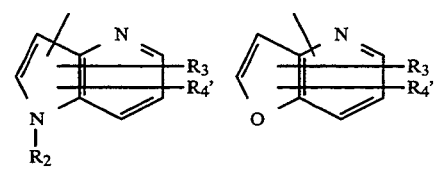
-continued
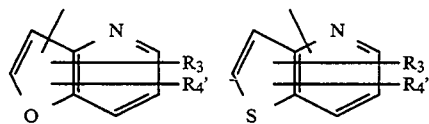
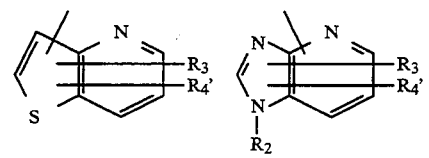
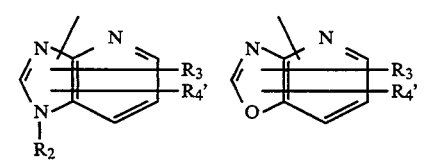
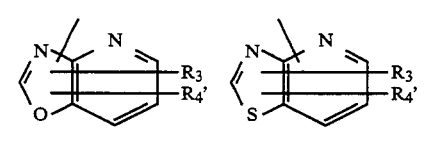
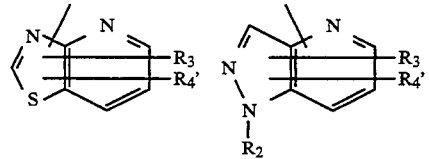
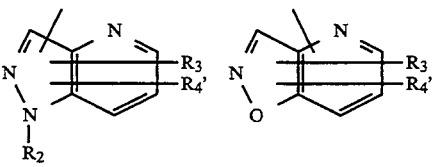
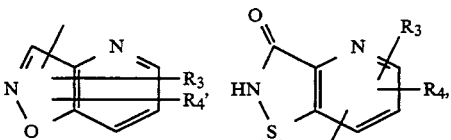
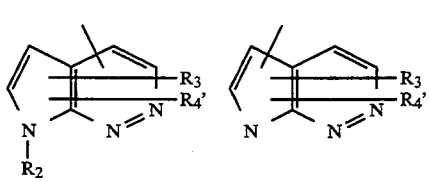
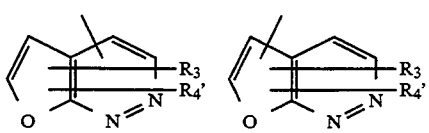
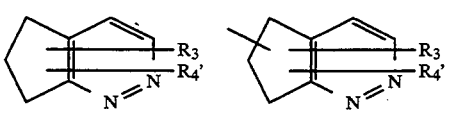

-continued
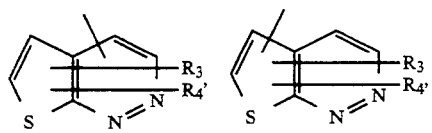
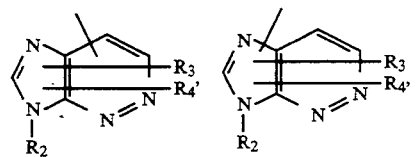
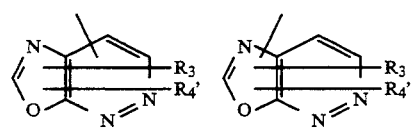
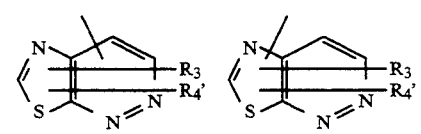
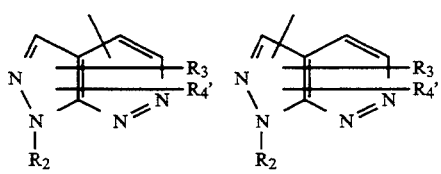
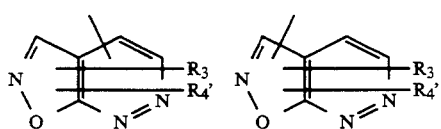
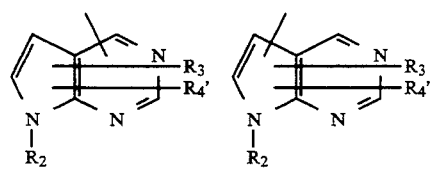
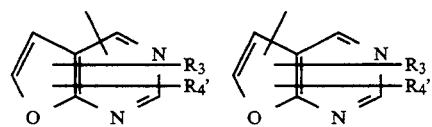
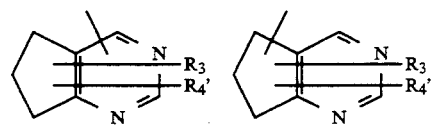
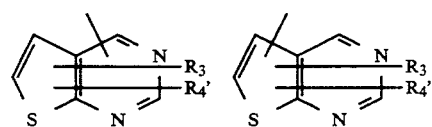
-continued
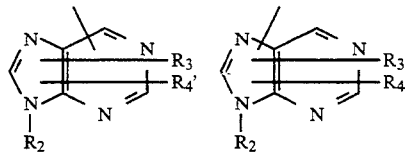
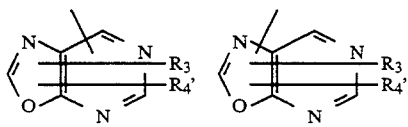
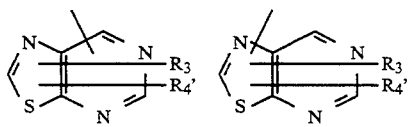
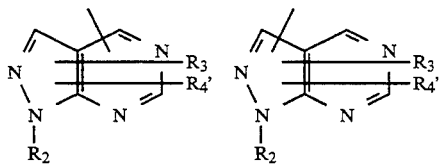
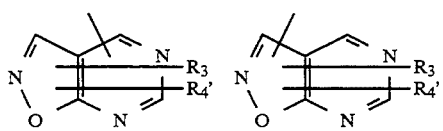
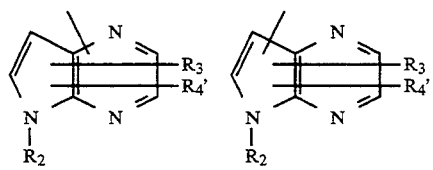
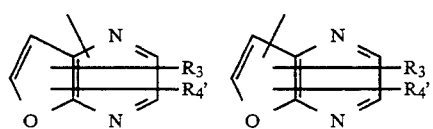
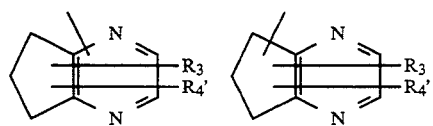
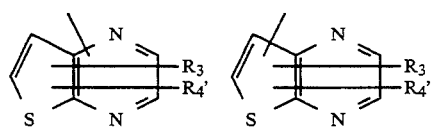
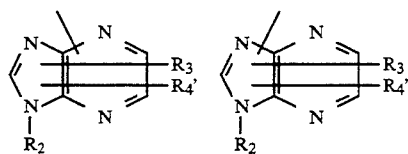

-continued
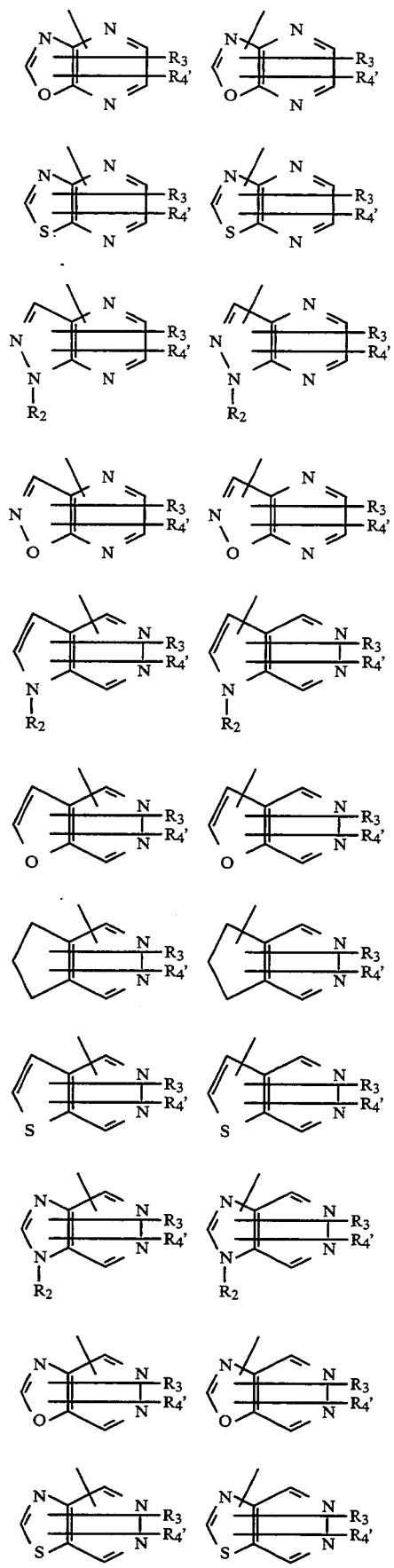
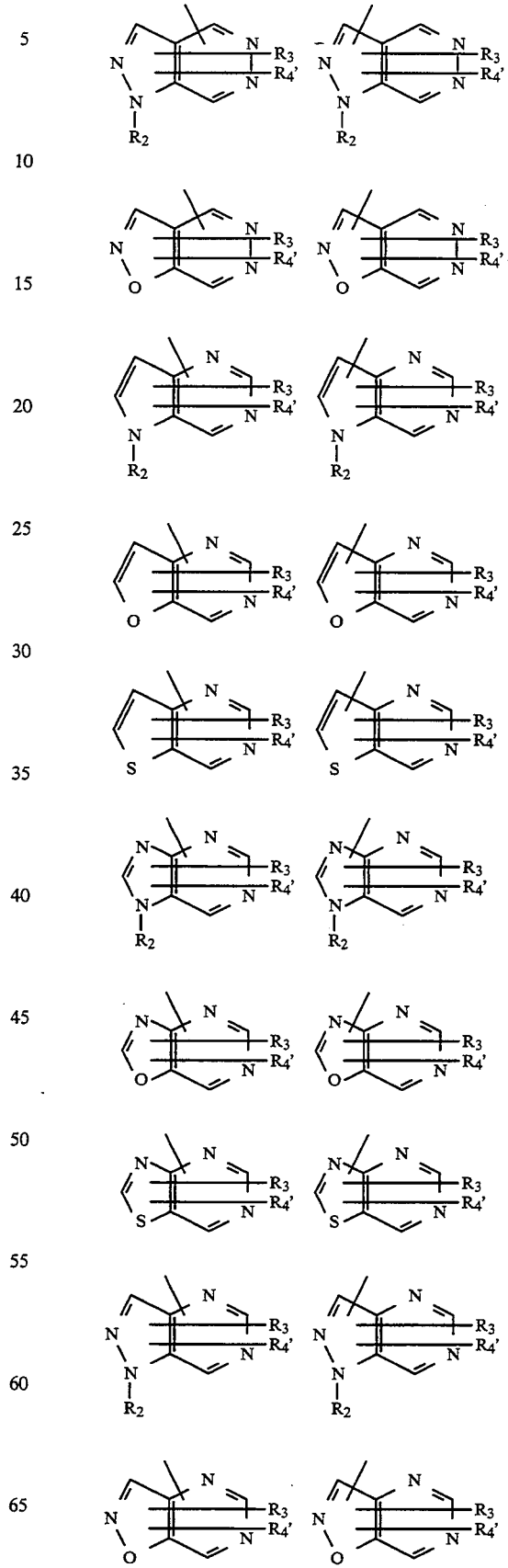

-continued
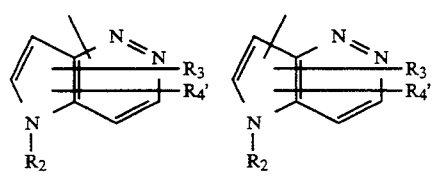 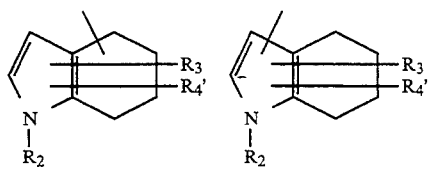
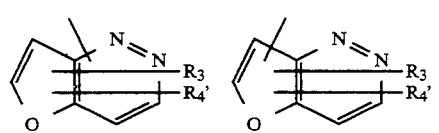 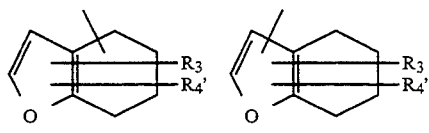
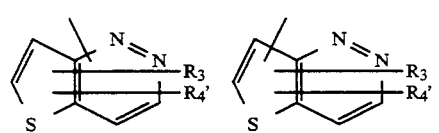 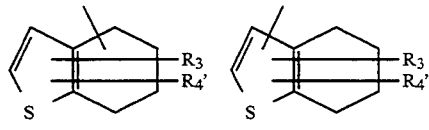
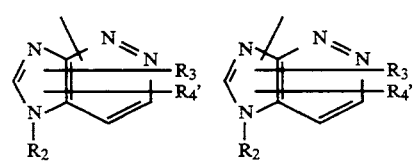 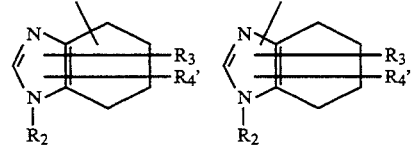
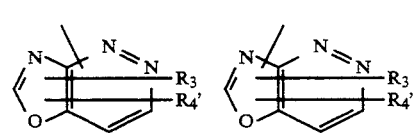 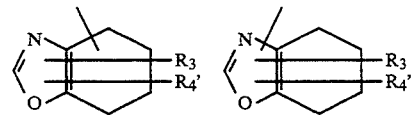
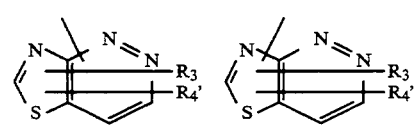 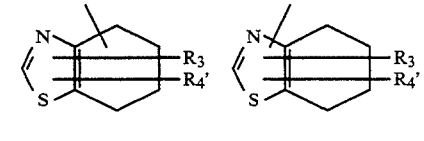
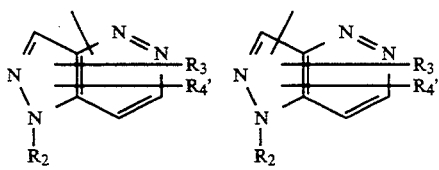 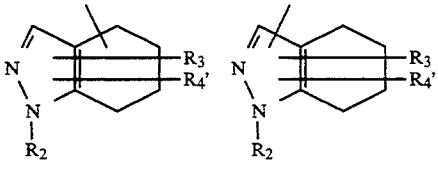
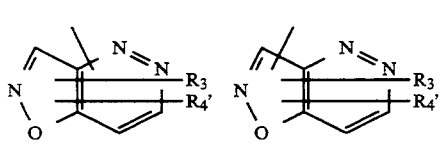 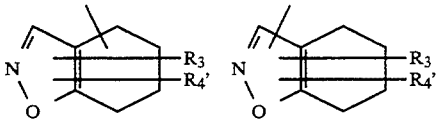
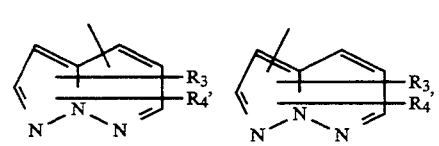 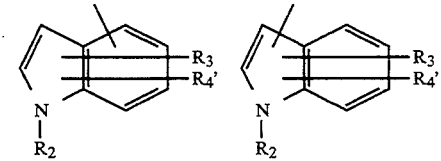
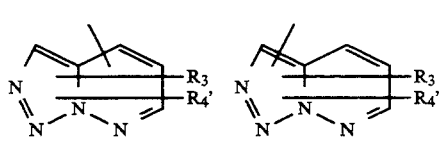 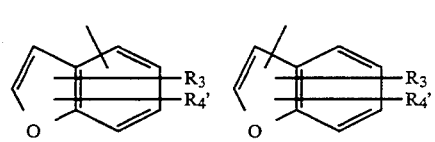

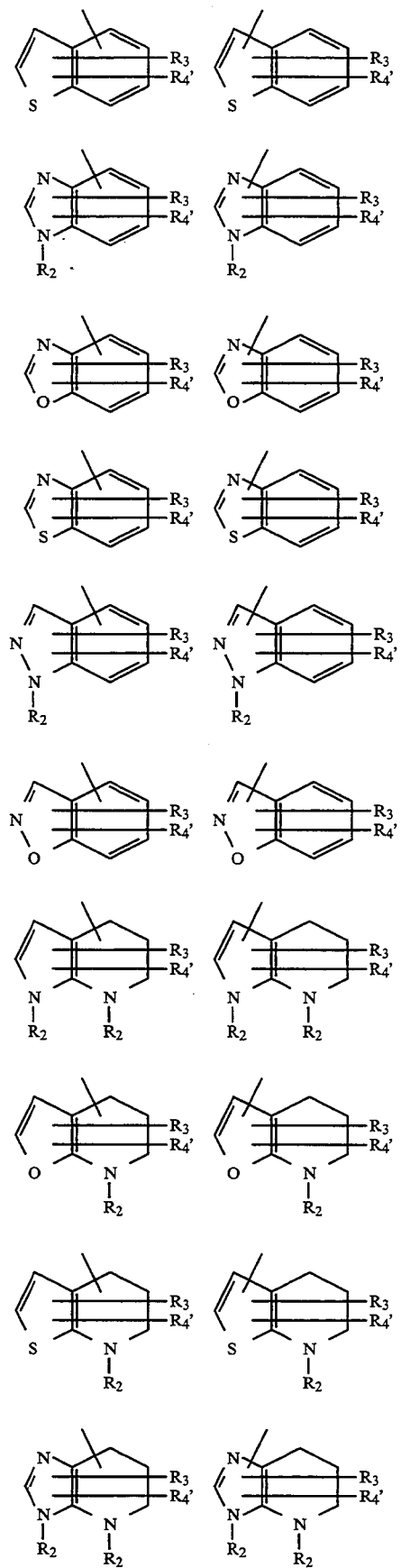
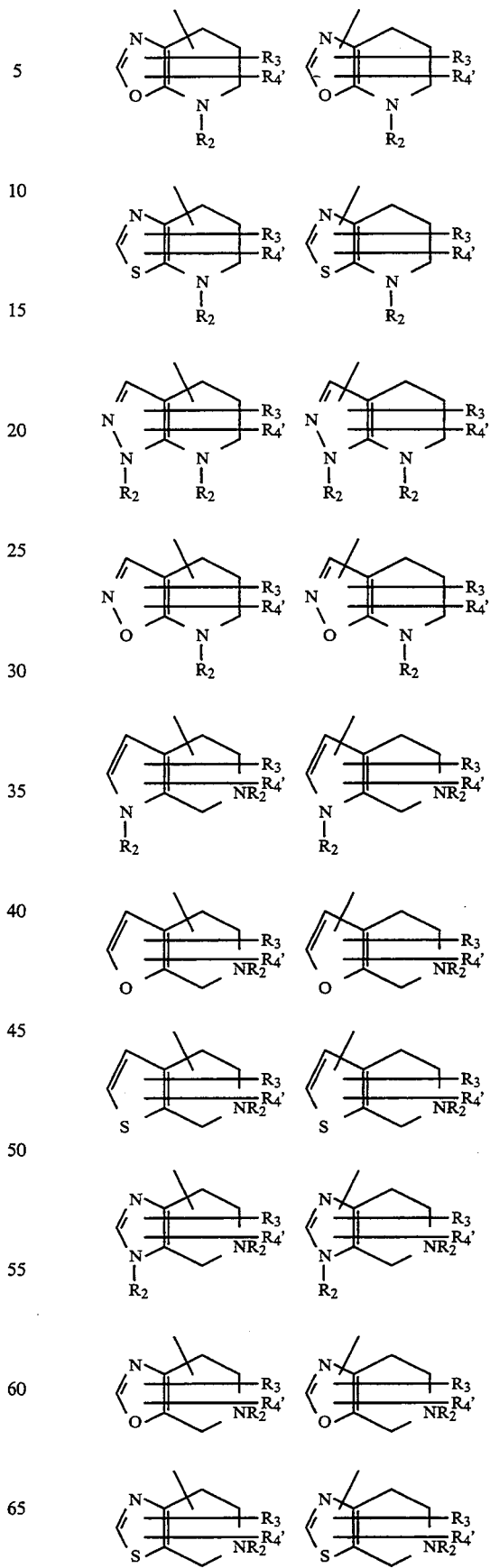

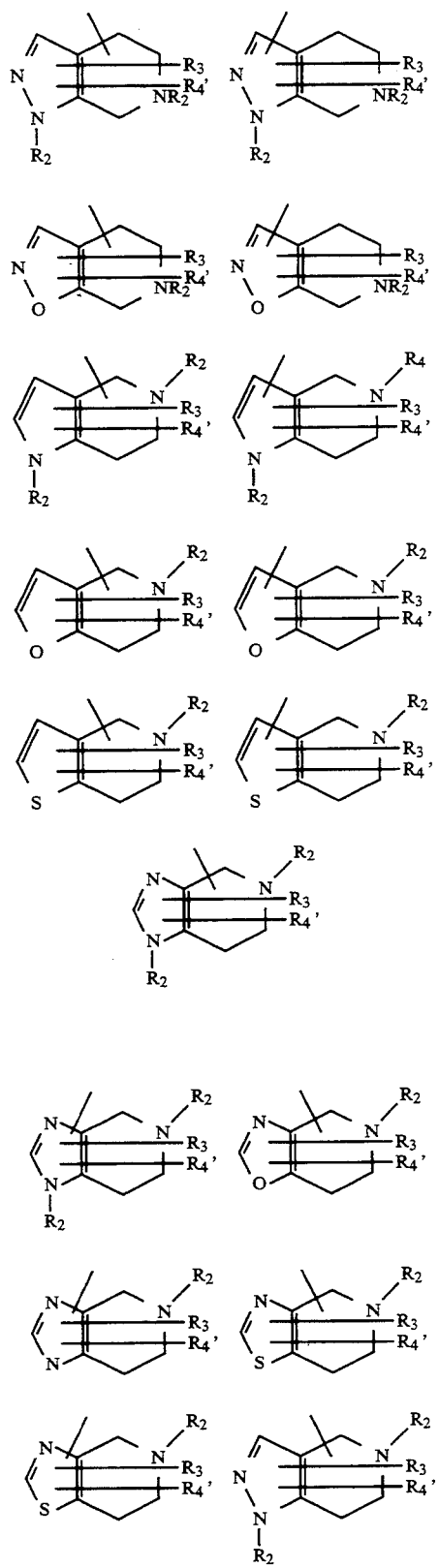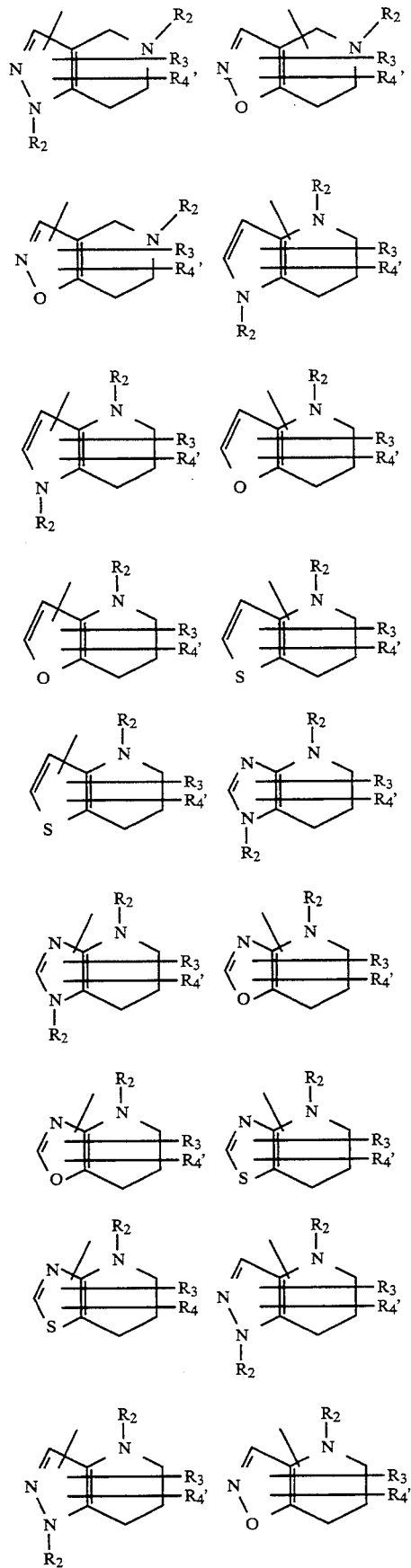

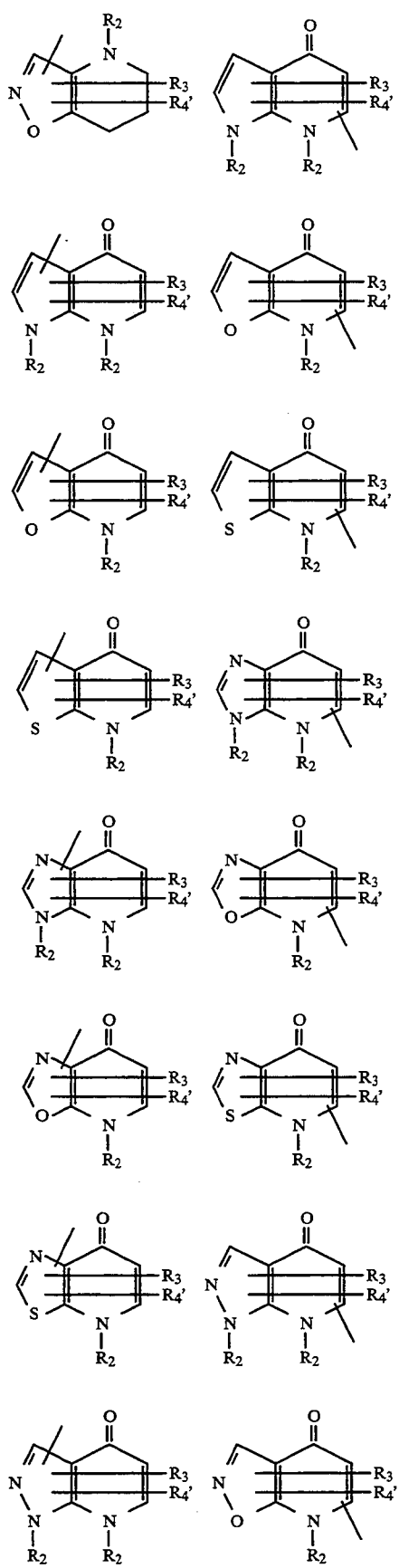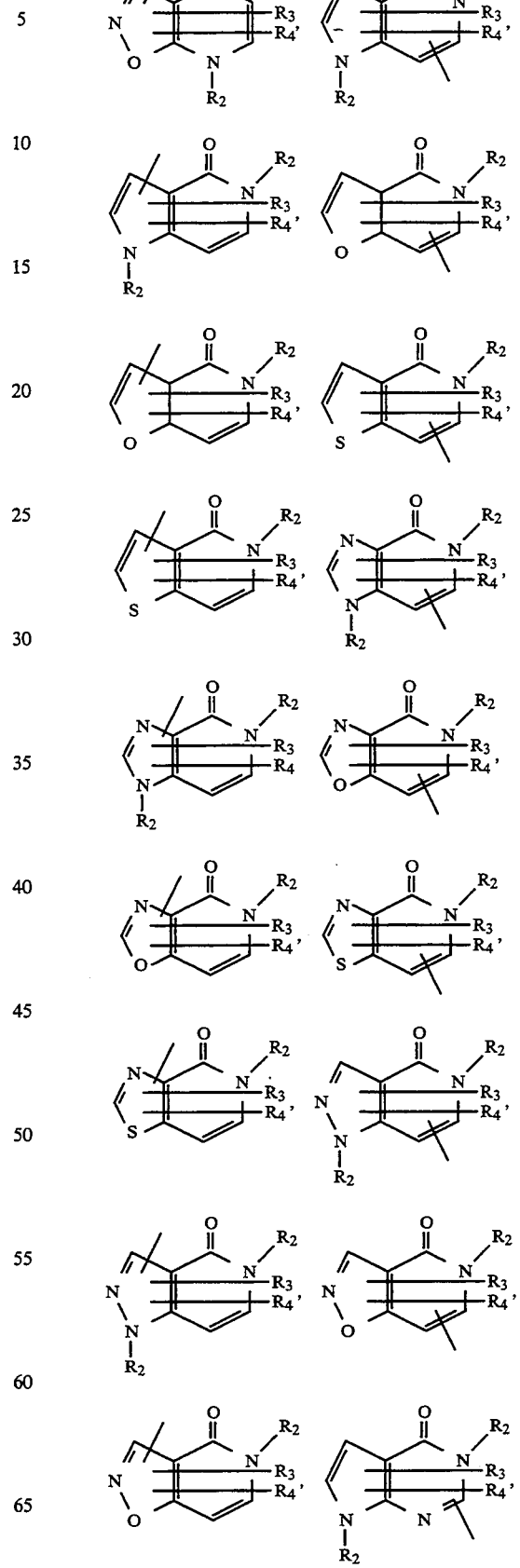

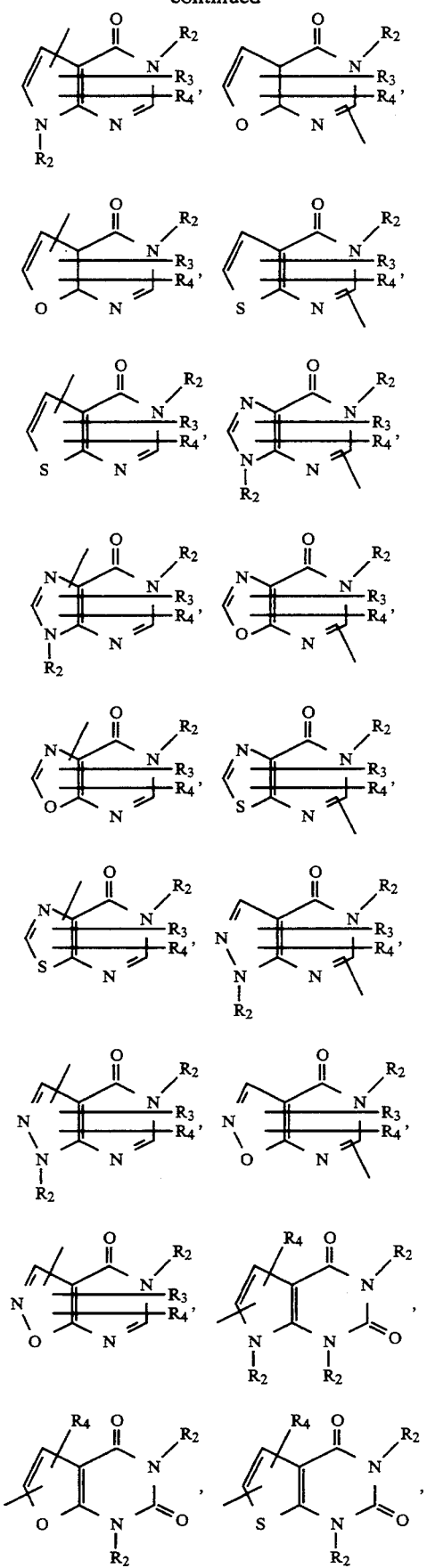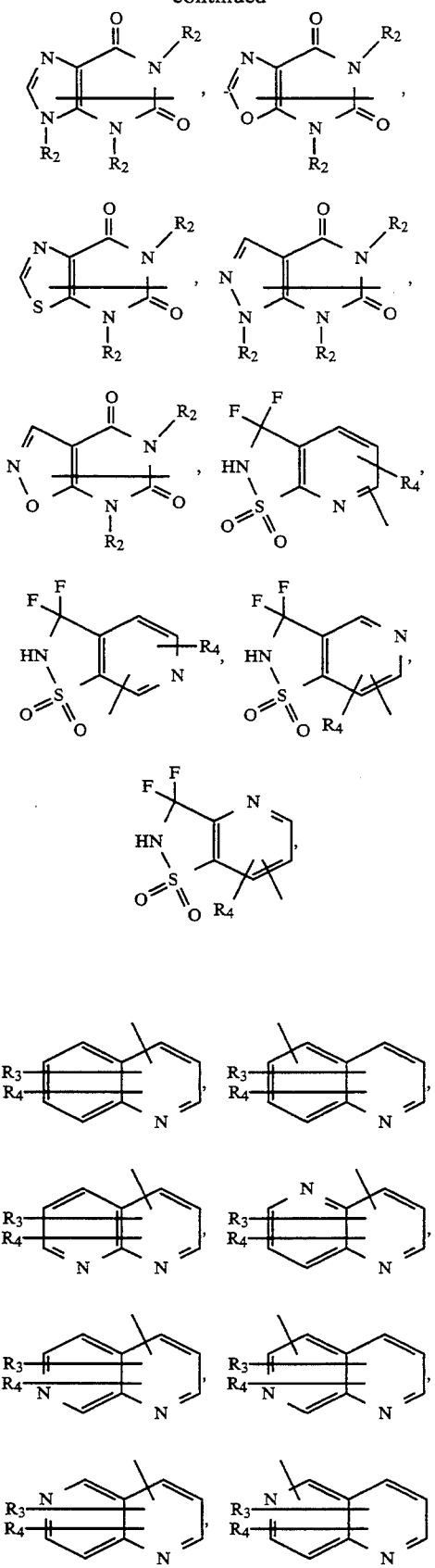

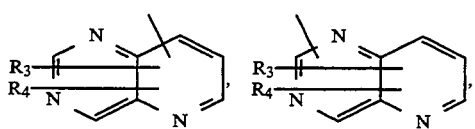
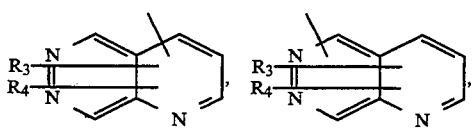
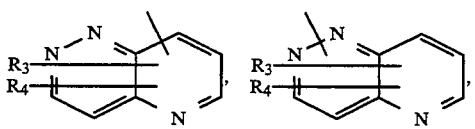
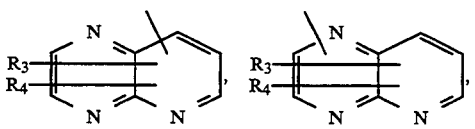
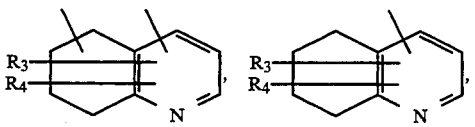
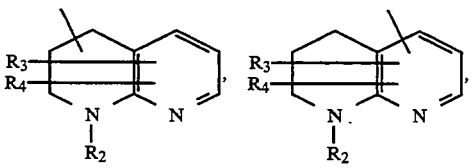
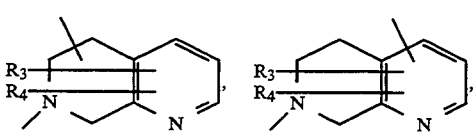
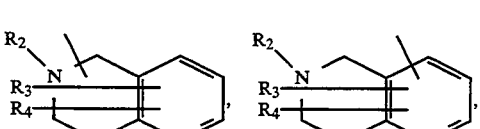
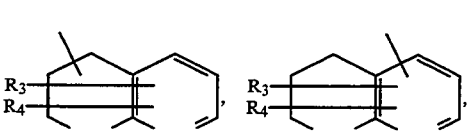
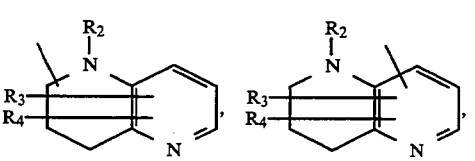
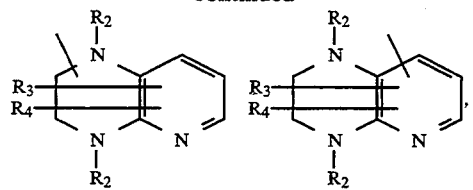
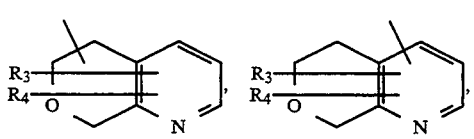
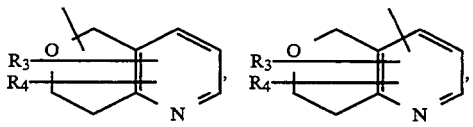
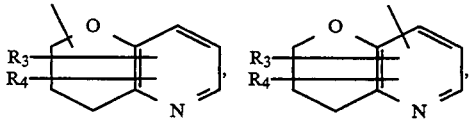
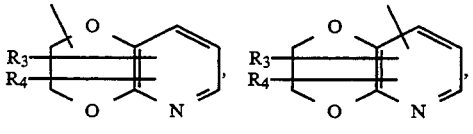
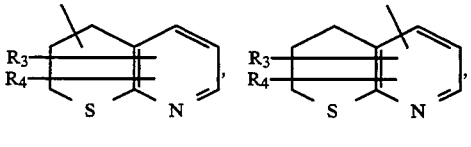
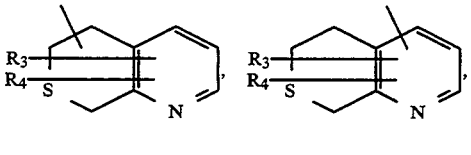
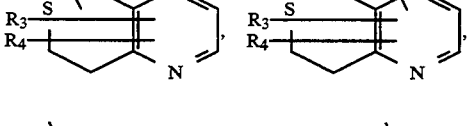
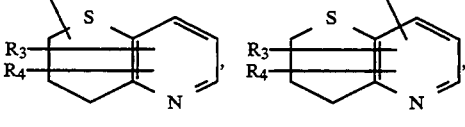
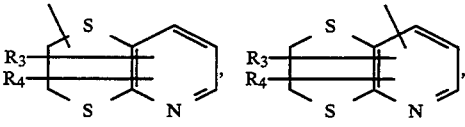
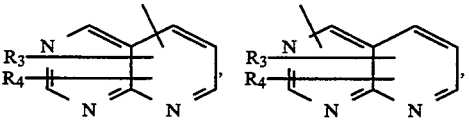

-continued
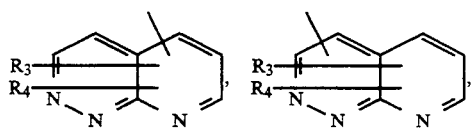 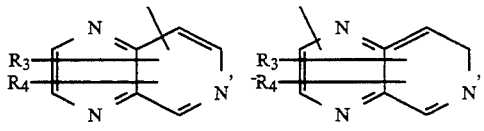
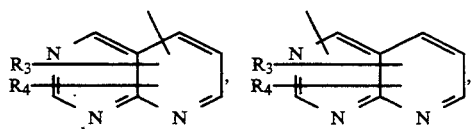 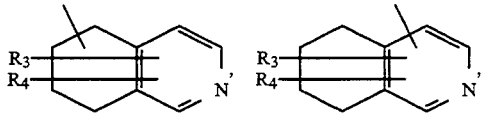
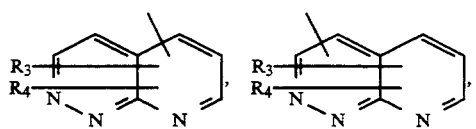 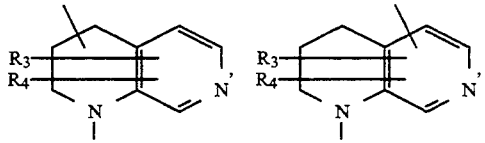
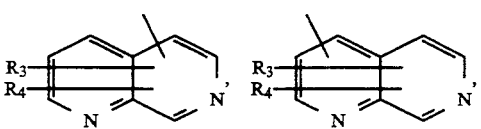 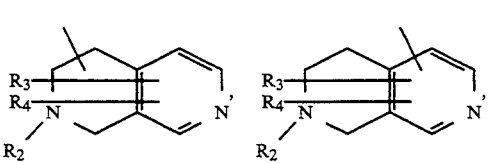
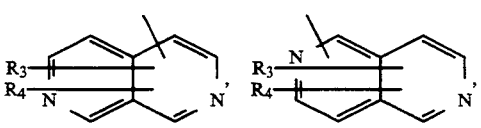 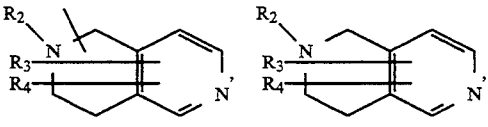
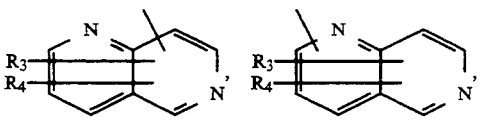 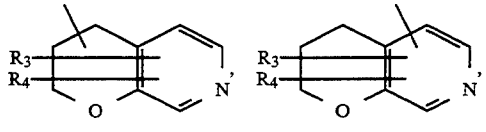
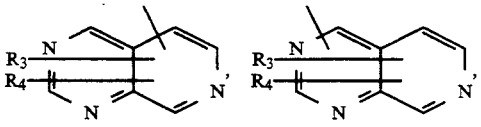 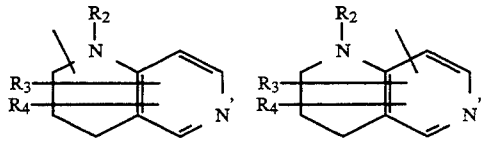
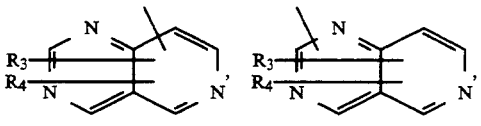 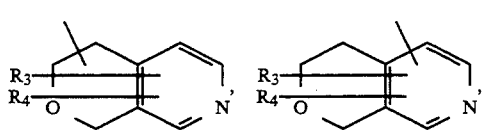
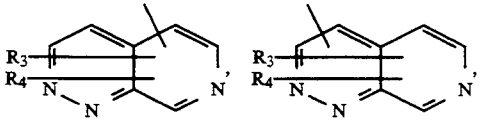 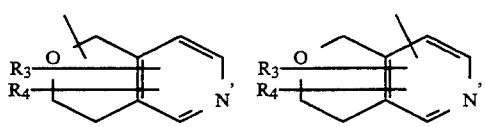
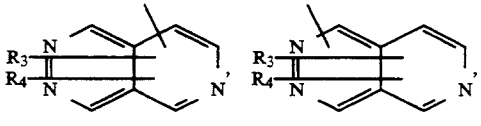 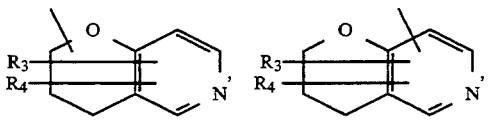
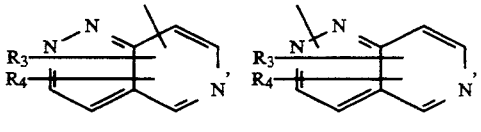 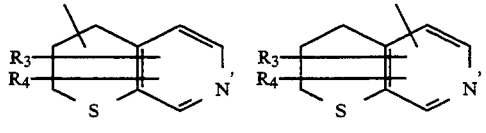

-continued
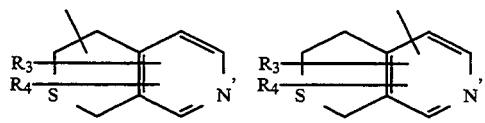
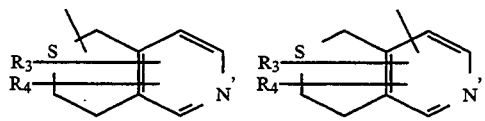
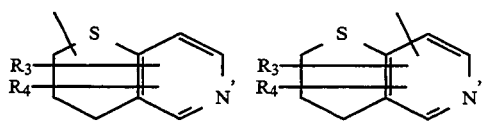
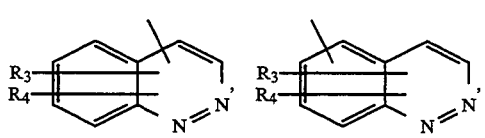
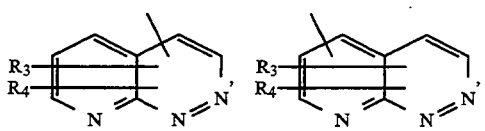
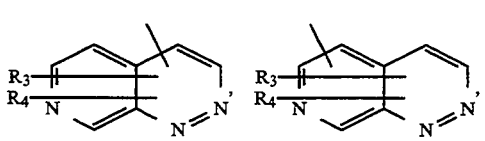
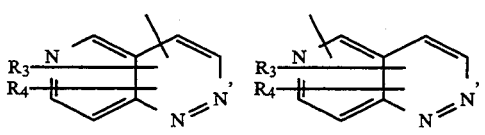
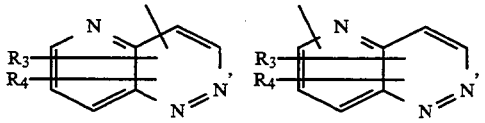
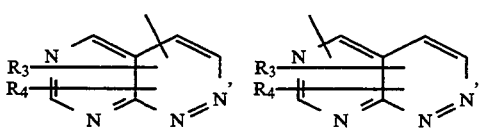
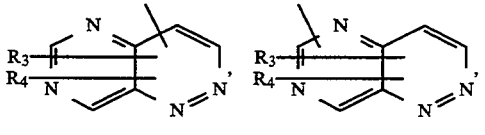
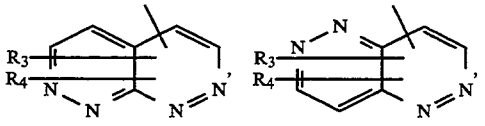
-continued
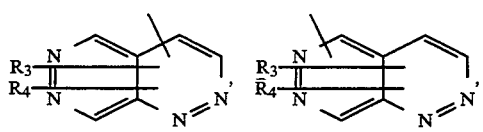
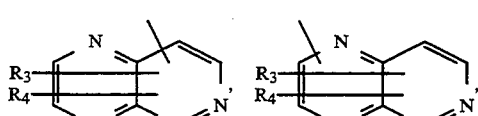
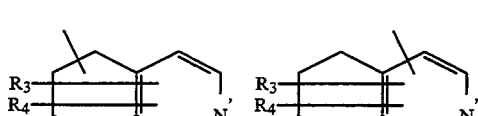
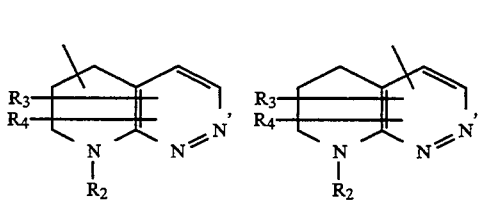
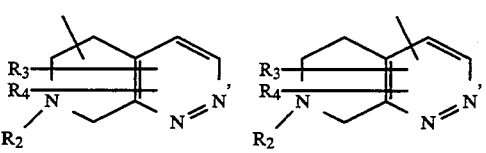
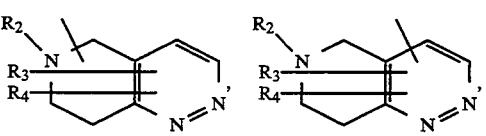
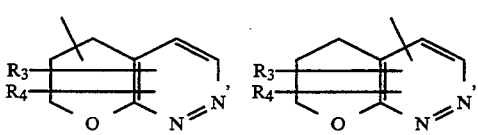
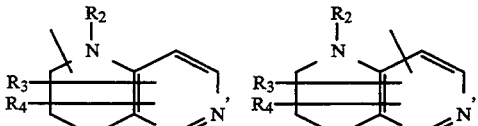
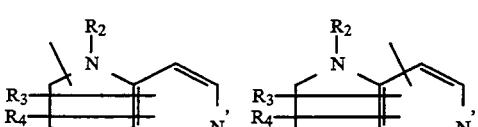
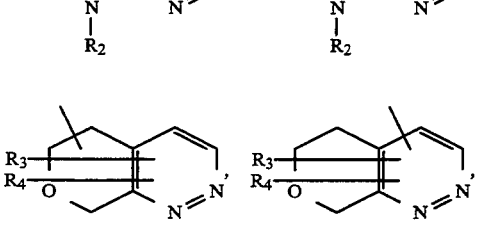

-continued
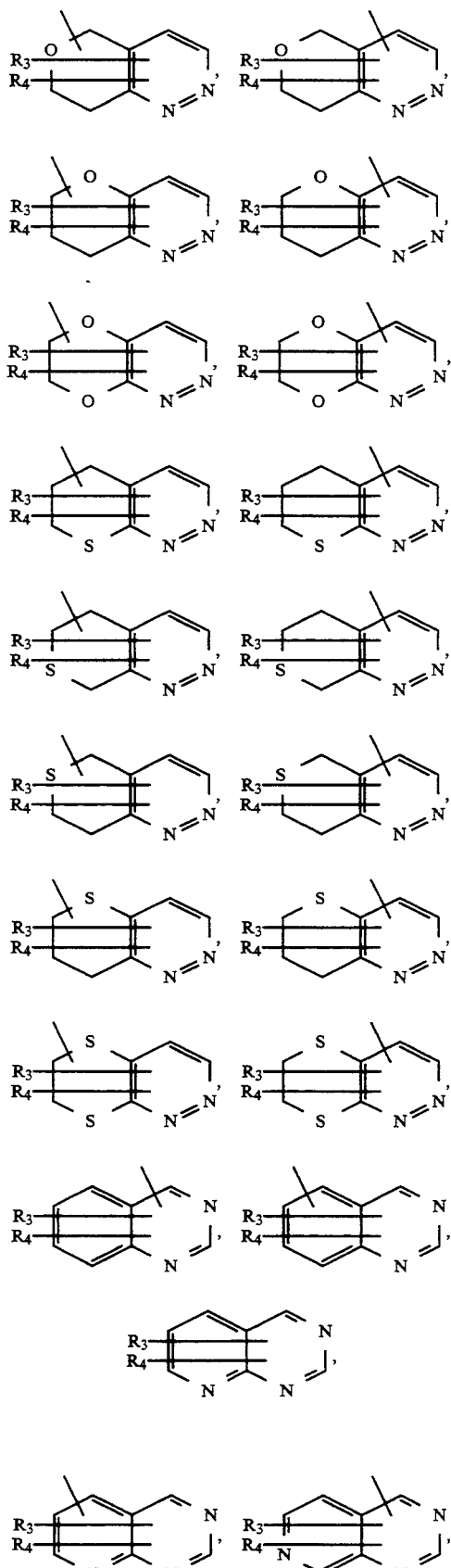
-continued
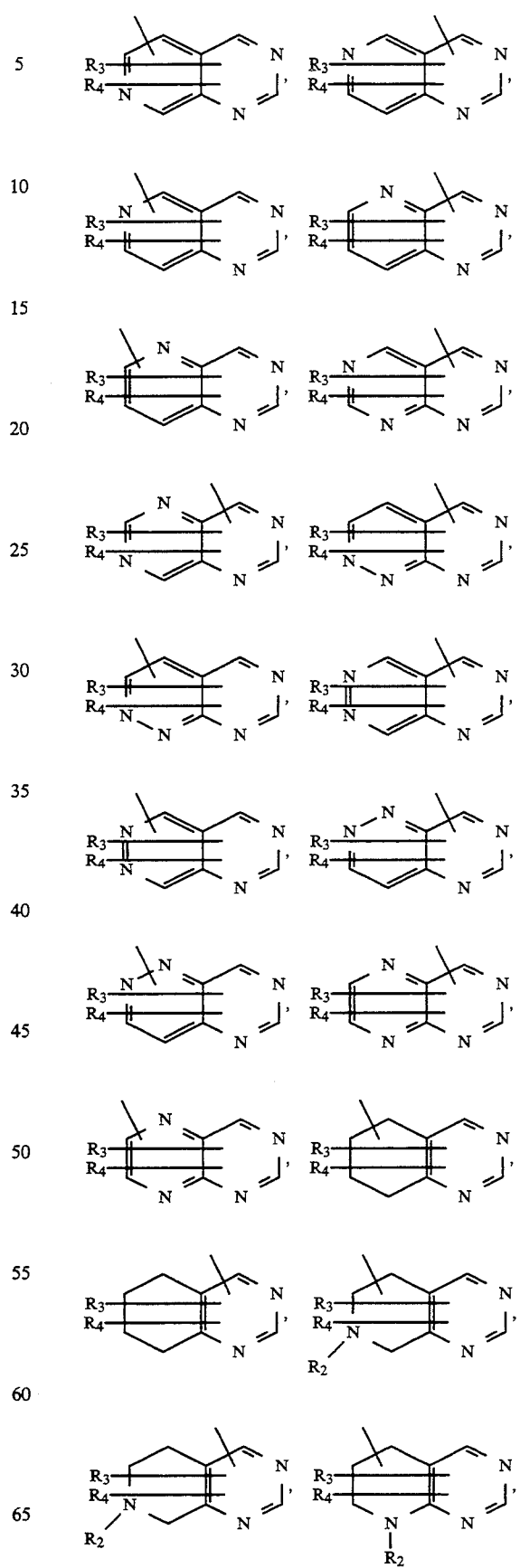

-continued
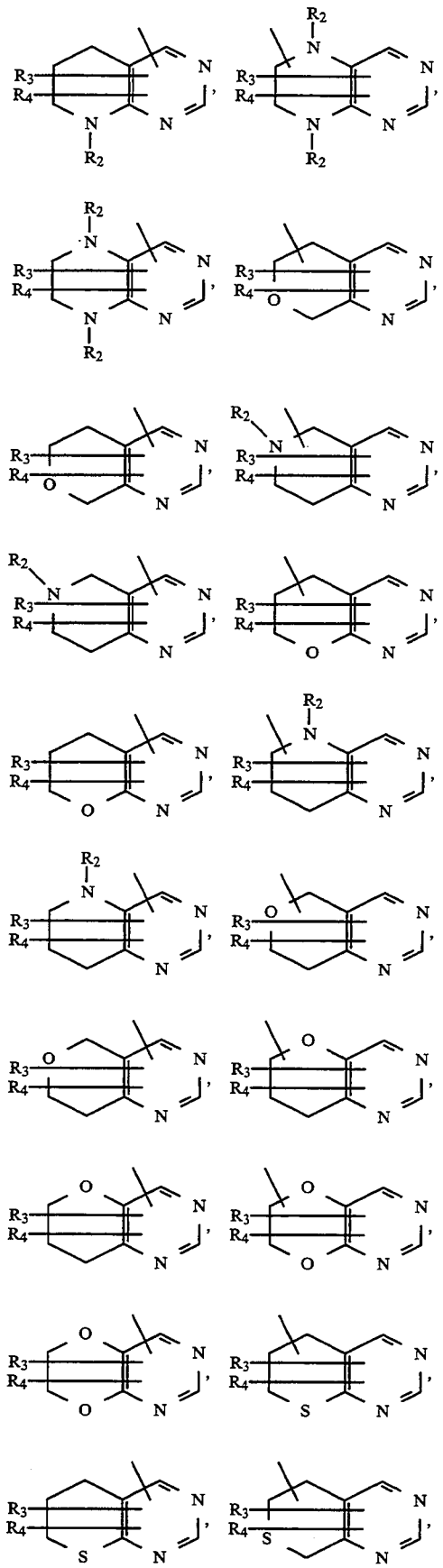
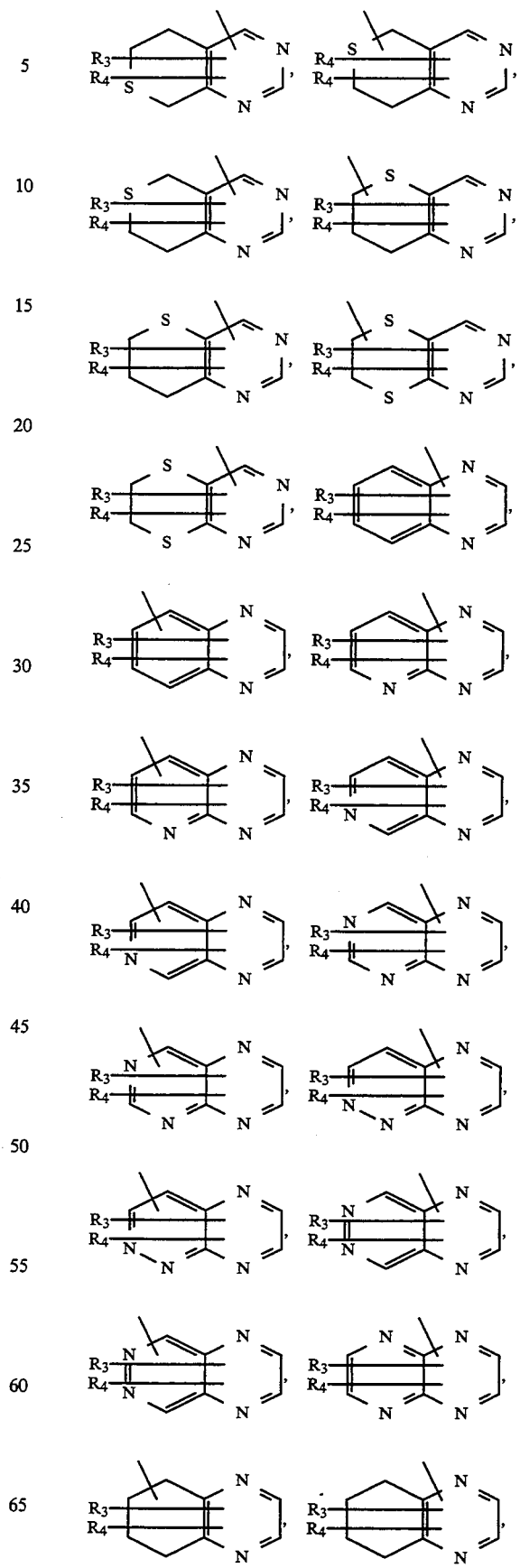

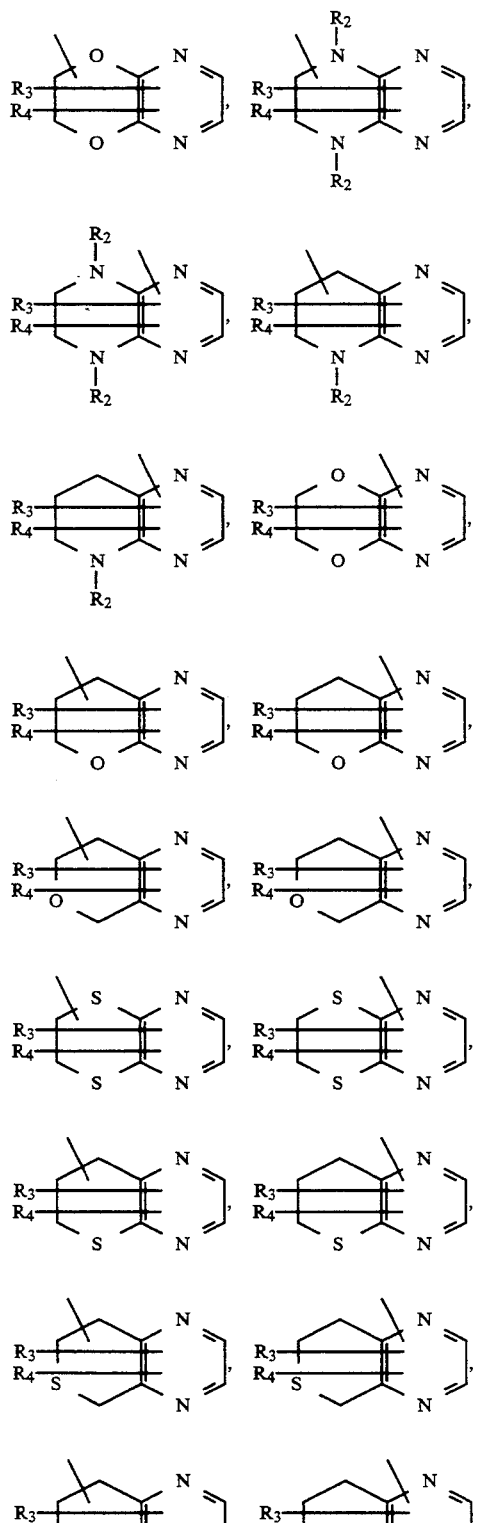
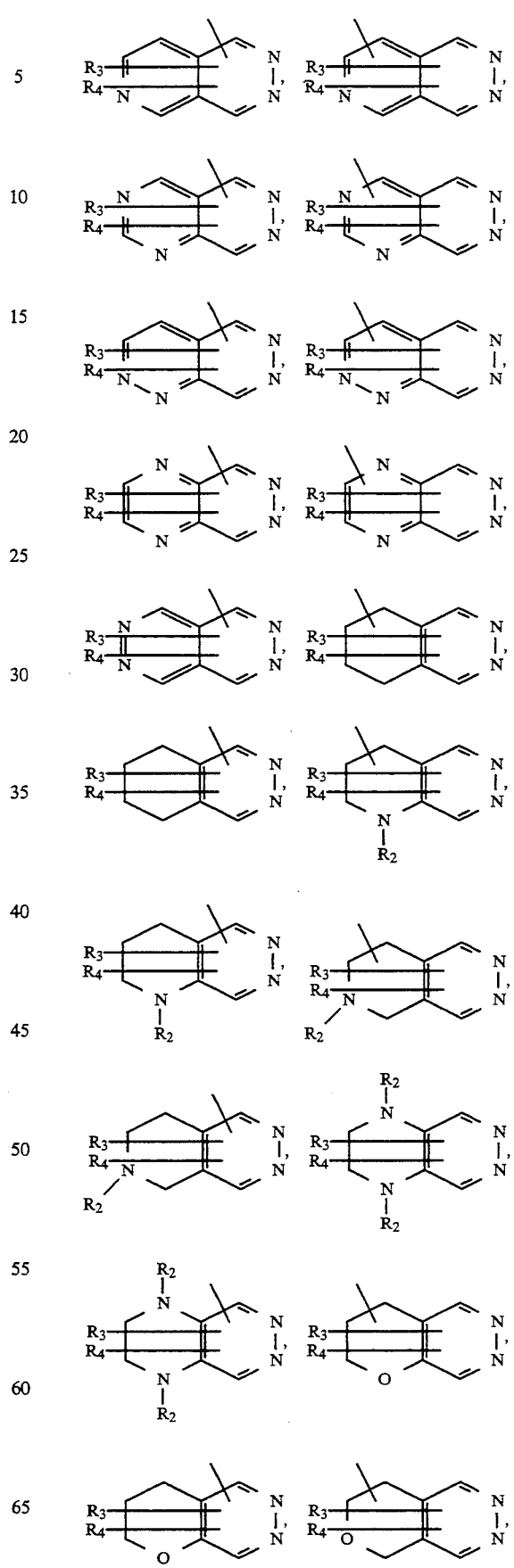

-continued
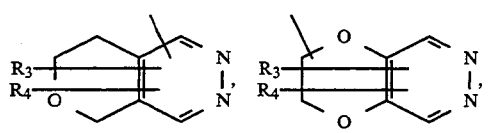
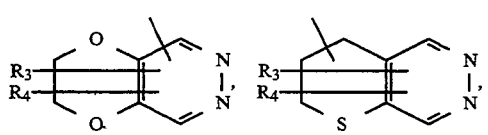
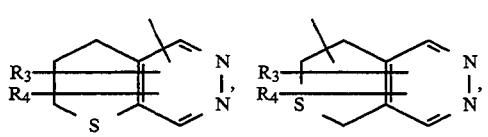
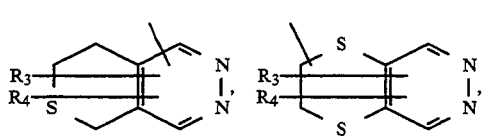
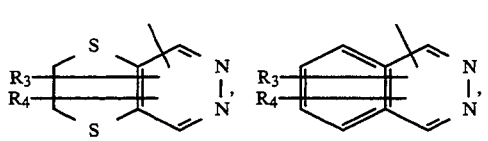
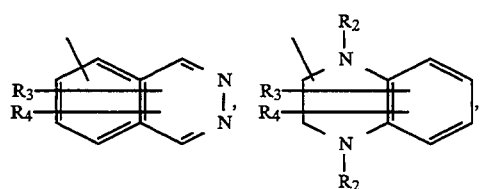
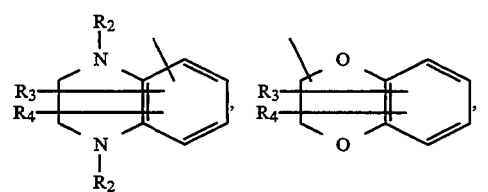
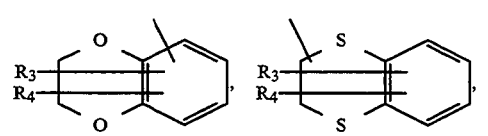
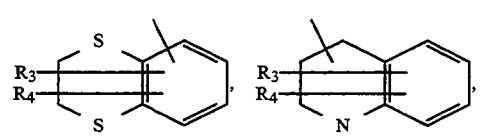
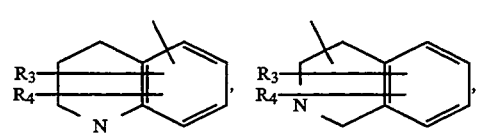
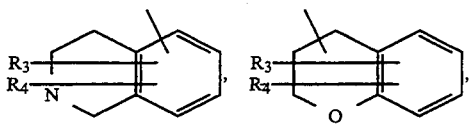
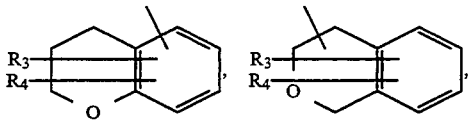
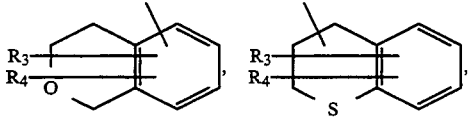
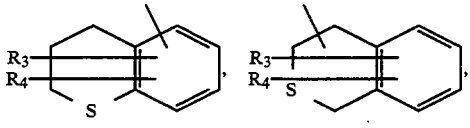
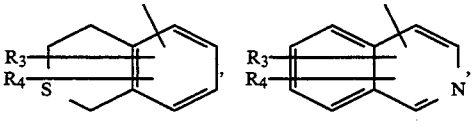
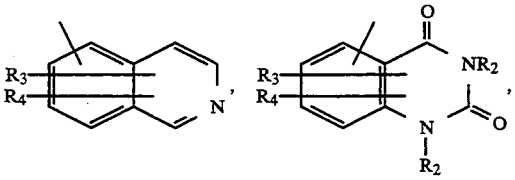
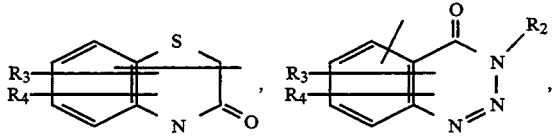
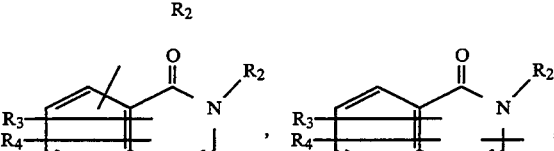
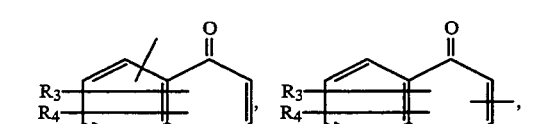
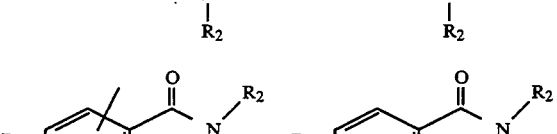
and the like. P The term "loweralkyl" as used herein refers to branched or straight chain alkyl groups comprising one to ten carbon atoms, including methyl, ethyl, propyl, isopropyl, n-butyl, t-butyl, neopentyl and the like.

The term "alkenyl" as used herein refers to a branched or straight chain comprising two to ten carbon atoms which has one or more carbon-carbon double bonds, including vinyl, propenyl, butenyl and the like.

The term "alkynyl" as used herein refers to a branched or straight chain comprising two to ten carbon atoms which has one or more carbon-carbon triple bonds, including ethynyl, propynyl, butynyl and the like.

The term "cycloalkyl" as used herein refers to an alicyclic group comprising from 3 to 7 carbon atoms, including cyclopropyl, cyclobutyl, cyclopentyl, cyclohexyl and the like.

The term "cycloalkylalkyl" as used herein refers to a loweralkyl radical to which is appended a cycloalkyl group, including cyclopentylmethyl, cyclohexylmethyl and the like.

The term "alkylene" as used herein refers to a 1 to 10 carbon straight or branched chain di-radical, including —$CH_2$—, —$CH(CH_3)$—, —$CH_2CH_2CH_2$—, —$CH(CH_3)CH_2CH_2$— and the like.

The term "halo-substituted loweralkyl" refers to a loweralkyl radical in which one or more of the hydrogen atoms are replaced by halogen, including chloromethyl, fluoroethyl, trifluoromethyl, pentafluoroethyl and the like.

The term "hydroxy-substituted loweralkyl" refers to a loweralkyl radical to which is appended one or two hydroxy (—OH) groups.

The term "halogen" or "halo" as used herein refers to I, Br, Cl or F.

The term "alkoxy" refers to $R_{34}O$— wherein $R_{34}$ is a loweralkyl or benzyl group. Representative examples of alkoxy groups include methoxy, ethoxy, t-butoxy, benzyloxy and the like.

The term "thioalkoxy" as used herein refers to $R_{35}S$— wherein $R_{35}$ is a loweralkyl or benzyl group.

The term "alkoxy-substituted loweralkyl" as used herein refers to a loweralkyl radical to which is appended an alkoxy group.

The term "thioalkoxy-substituted loweralkyl" as used herein refers to a a loweralkyl radical to which is appended a thioalkoxy group. Representative thioalkoxy-substituted loweralkyl groups include methylthiomethyl, methylthioethyl, ethylthioethyl, propylthiomethyl and the like.

The term "hydroxy-substituted loweralkyl" as used herein refers to a loweralkyl radical to which is appended one or two hydroxy (—OH) groups.

The term "carboxy-substituted loweralkyl" as used herein refers to a loweralkyl radical to which is appended a carboxy group (—COOH), including carboxymethyl, carboxyethyl and the like.

The term "alkoxycarbonyl" as used herein refers to —$C(O)OR_{36}$ wherein $R_{36}$ is a carboxy-protecting group.

The term "alkoxycarbonyl-substituted loweralkyl" as used herein refers to a loweralkyl radical to which is appended an alkoxycarbonyl group.

The term "alkoxy-substituted alkoxy" as used here refers to an alkoxy radical to which is appended another alkoxy radical, including methoxymethoxy, methoxyethoxy, ethoxyethoxy and the like.

The term "alkylamino" as used herein refers to —$NHR_{37}$ wherein $R_{37}$ is a loweralkyl group.

The term "dialkylamino" as used herein refers to —$NR_{38}R_{39}$ wherein $R_{38}$ and $R_{39}$ are independently selected from loweralkyl.

The term "alkanoyloxyalkyl" as used herein refers to a loweralkyl radical to which is appended —$OC(O)R_{40}$ wherein $R_{40}$ is loweralkyl.

The term "aroyloxyalkyl" as used herein refers to a loweralkyl radical to which is appended —$OC(O)R_{41}$ wherein $R_{41}$ is aryl.

The term "alkoxycarbonylalkyl" as used herein refers to a loweralkyl radical to which is appended an alkoxycarbonyl group.

The term "alkoxycarbonyloxyalkyl" as used herein refers to a loweralkyl radical to which is appended —$OC(O)OR_{42}$ wherein $R_{42}$ is loweralkyl or cycloalkyl.

The term "alkoxycarbonylaminoalkyl" as used herein refers to a loweralkyl radical to which is appended —$NHC(O)OR_{43}$ wherein $R_{43}$ is loweralkyl.

The term "alkylaminocarbonylaminoalkyl" as used herein refers to a loweralkyl radical to which is appended —$NHC(O)NHR_{44}$ wherein $R_{44}$ is loweralkyl.

The term "alkanoylaminoalkyl" as used herein refers to a loweralkyl radical to which is appended —$NHC(O)R_{45}$ wherein $R_{45}$ is loweralkyl.

The term "heterocycliccarbonyloxyalkyl" as used herein refers to a loweralkyl radical to which is appended —$OC(O)R_{46}$ wherein $R_{46}$ is a heterocyclic group.

The term "aryl" as used herein refers to a phenyl or a $C_9$ or $C_{10}$ bicyclic carbocyclic ring system having one or more aromatic rings, including naphthyl, tetrahydronaphthyl, indanyl, indenyl and the like. Aryl groups can be unsubstituted or substituted with one, two or three substituents independently selected from loweralkyl, halo-substituted loweralkyl, alkoxy, thioalkoxy, alkoxycarbonyl, hydroxy, halo, mercapto, nitro, amino, alkylamino, dialkylamino, carboxaldehyde, carboxy and carboxamide.

The term "arylalkyl" as used herein refers to a loweralkyl radical to which is appended an aryl group. Representative arylalkyl groups include benzyl, phenylethyl, fluorobenzyl, fluorophenylethyl and the like.

The term "aliphatic heterocycle" as used herein refers to a saturated cyclic group containing 5 to 7 ring atoms and, in particular, at least 1 nitrogen atom in the ring and optionally 1 additional heteroatom selected from S, $S(O)_2$, O and N, with the remaining ring atoms being carbon atoms. The ring can be substituted on a carbon atom or a heteroatom, for example, with loweralkyl, alkoxy or alkoxy-substitute alkoxy. Representative aliphatic heterocycles include, pyrrolidine, piperidine, piperazine, morpholine, thiomorpholine, S,S-dioxothiomorpholine, 4-methoxymethoxypiperidine and the like.

The term "heterocyclic group" or "heterocyclic" as used herein in the context of the terms "heterocyclic-substituted loweralkyl" and "5- to 7-membered aliphatic heterocycle" refers to any 3- or 4-membered ring containing a heteroatom selected from oxygen, nitrogen and sulfur, or a 5-, 6- or 7-membered ring containing one, two or three nitrogen atoms; one nitrogen and one sulfur atom; or one nitrogen and one oxygen atom; wherein the 5-membered ring has 0-2 double bonds and the 6- or 7-membered ring has 0-3 double bonds; wherein the nitrogen and sulfur heteroatoms can optionally be oxidized; wherein the nitrogen heteroatom can optionally be quaternized; and including any bicyclic group in which any of the above heterocyclic rings is fused to a benzene ring or another 5-, 6- or 7-membered heterocyclic ring independently as defined above. Heterocyclics include indolyl, quinolyl, isoquinolyl, tetrahydroquinolyl, benzofuryl, benzothienyl, azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl, benzothienyl, homopiperazinyl, homopiperidinyl, homomorpholinyl and the like.

Heterocyclics can be unsubstituted or monosubstituted or disubstituted with substitutents independently selected from hydroxy, halo, oxo (=O), amino, alkylamino, dialkylamino, alkoxy, thioalkoxy, carboxy, alkoxycarbonyl, loweralkyl, cycloalkyl, —OSO$_3$H and halo-substituted loweralkyl.

The term "heterocyclic-substituted loweralkyl" as used herein refers to a loweralkyl radical to which is appended a heterocyclic group.

The term "N-protecting group" or "N-protected" as used herein refers to those groups intended to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, phenylsulfonyl, benzyl, triphenylmethyl (trityl), t-butyloxycarbonyl (Boc), benzyloxycarbonyl (Cbz) and the like.

As used herein, the term "carboxy-protecting group" refers to a carboxy group which has been esterified with one of the commonly used carboxylic acid protecting ester groups employed to block or protect the carboxylic acid functionality while the reactions involving other functional sites of the compound are carried out. Carboxy-protecting groups are disclosed in Greene, "Protective Groups in Organic Synthesis" pp. 152-186 (1981), which is incorporated herein by reference. In addition, a carboxy-protecting group can be used as a prodrug whereby the carboxy-protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975). Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are incorporated herein by reference. Examples of esters useful as prodrugs for compounds containing carboxyl groups can be found on pages 14-21 of "Bioreversible Carriers in Drug Design: Theory and Application", edited by E. B. Roche, Pergamon Press:New York (1987). Representative carboxy-protecting groups are C$_1$ to C$_8$ alkyl (e.g., methyl, ethyl or tertiary butyl and the like), benzyl and substituted derivatives thereof such as alkoxybenzyl or nitrobenzyl groups and the like, dialkylaminoalkyl (e.g., dimethylaminoethyl and the like), alkanoyloxyalkyl groups such as pivaloyloxymethyl or propionyloxymethyl and the like, aroyloxyalkyl, such as benzoyloxyethyl and the like, alkoxycarbonylalkyl, such as methoxycarbonylmethyl, cyclohexyloxycarbonylmethyl and the like, alkoxycarbonyloxyalkyl, such as t-buyloxycarbonyloxymethyl and the like, alkoxycarbonylaminoalkyl, such as t-butyloxycarbonylaminomethyl and the like, alkylaminocarbonylaminoalkyl, such as methylaminocarbonylaminomethyl and the like, alkanoylaminoalkyl, such as acetylaminomethyl and the like, heterocycliccarbonyloxyalkyl, such as 4-methylpiperazinylcarbonyloxymethyl and the like, dialkylaminocarbonylalkyl, such as dimethylaminocarbonylmethyl and the like, (5-(loweralkyl)-2-oxo-1,3-dioxolen-4-yl)alkyl, such as (5-t-butyl-2-oxo-1,3-dioxolen-4-yl)methyl and the like and (5-phenyl-2-oxo-1,3-dioxolen-4-yl)alkyl, such as (5-phenyl-2-oxo-1,3-dioxolen-4-yl)methyl and the like.

When used herein, a formula such as

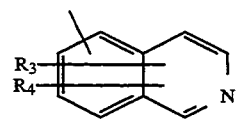

represents a bicyclic heterocycle where R$_3$ is bonded to either of the 6-membered rings and R$_4$ is bonded to either of the 6-membered rings.

When the compounds of formula I contain one asymmetric carbon atom, they can exist as pure enantiomers or mixtures of enantiomers. When the compounds of formula I contain more than one asymmetric carbon atom, they can exist as diastereomers, mixtures of diastereomers, diastereomeric racemates or mixtures of diastereomeric racemates. The present invention includes within its scope all of the isomeric forms. The terms "R" and "S" configuration used herein are as defined by IUPAC 1974 Recommendations for Section E, Fundamental Stereochemistry, Pure Appl. Chem (1976) 45, 13-30.

In addition, in the compounds of the invention, combinations of substituents and/or variables (i.e., A, D, E, G, R$_1$, R$_2$, R$_3$, R$_4$, etc.) are permissible only if such combinations result in stable compounds.

In general, the compounds of this invention can be prepared by the processes illustrated in Schemes I through XXII. It should be understood that substituents D, E, G, Q, R$_1$, R$_2$, R$_3$, R$_4$, etc. as used herein correspond to the groups identified by formula (I). P is a protecting group. In the course of synthesis, certain groups present in the molecule, particulary carboxylic acid and tetrazole groups, are protected and deprotected as necessary. The term "protecting group" is well known in the art and refers to substituents on functional groups of compounds undergoing chemical transformation which prevent undesired reactions and degradations during a synthesis; see, for example, T. H. Greene, "Protective Groups in Organic Synthesis", John Wiley & Sons, New York (1981) for methods of introducing and removing appropriate protecting groups. Suitable carboxy-protecting groups include t-butyl and benzyl groups. Suitable tetrazole nitrogen-protecting groups include triphenylmethyl (Tr), benzyl, t-butyl, methoxymethyl, benzyloxymethyl, p-nitrobenzyl, 1-ethoxyethyl and the like.

The compounds of formula (I) may be prepared using the reactions and techniques described in this section. The reactions are performed in a solvent appropriate to the reagents and materials employed and suitable for the transformation being effected. It is understood by those skilled in the art of organic synthesis that the functionality present on the heterocycle and other portions of the molecule must be consistent with the chemical transformation proposed. This will frequently necessitate judgment as to the order of synthetic steps, protecting groups required and deprotection conditions. Throughout the following section, not all compounds of formula (I) falling into a given class may necessarily be prepared by all methods described for that class. Substituents on the starting materials may be incompatible with some of the reaction conditions required in, some of the methods described. Such restrictions to the substituents which are compatible with the reaction conditions will be readily apparent to one skilled in the art and alternative methods described must then be used.

Schemes I-XV illustrate methods of preparing compounds of the invention comprising various —G—E— substituents.

Scheme I

Reaction Scheme I illustrates a method of preparing compounds wherein —G—E— is —N($R_5$)—. According to Scheme I an amino compound of Formula 82 is alkylated under standard conditions (e.g., $R_5$—X' wherein X' is a leaving group) and then reacted with a chloro-heterocycle to give a compound of Formula 81.

Scheme II

According to Scheme II, compounds wherein —G—E— is —O— are prepared by coupling a hydroxy-substituted heterocycle with a bromo compound of Formula 80 in the presence of a copper salt to give a compound of Formula 83.

Scheme III

Reaction Scheme III illustrates a method of preparing compounds wherein —G—E— is —S—. According to Scheme III, a thiol of Formula 85 is reacted with a chloro-heterocycle to give a compound of Formula 84.

Scheme IV

Reaction Schemes IVA and IVB illustrate alternative methods of preparing compounds wherein —G—E— is —CH$_2$—N($R_5$)—. According to Scheme IVA, an amino compound of Formula 86 is reacted with a chloro-heterocycle in the presence of a base, such as triethylamine or lithium hexamethyldisilazide, to give a compound of Formula 87. Alternatively, according to Scheme IVB, a chloro-heterocycle is reacted with a primary amine to give a compound of Formula 88. This secondary amine is reacted with a bromo compound of Formula 89 to give a tertiary amine of Formula 87.

Scheme V

According to Scheme V, compounds wherein —G—E— is —CH($R_5$)—NH— are prepared by oxidizing a compound of Formula 90 to aldehyde 91. Addition of an organometallic reagent (e.g., $R_5$-M is propyl-Grignard reagent) yields secondary alcohol 92. The alcohol is convened to a leaving group (e.g., X' is a mesylate) which is displaced with a heterocyclic amine to afford a compound of Formula 94.

Scheme VI

Reaction Schemes VIA and VIB illustrate alternative methods of preparing compounds wherein —G—E— is —CH($R_5$)—O—. According to Scheme VIA, a compound of Formula 93 having a leaving group X', e.g., mesylate, is reacted with a hydroxy-substituted heterocyclic compound in the presence of a base to give a compound of Formula 95. Alternatively, according to Scheme VIB, secondary alcohol 92, whose preparation is illustrated in Scheme V, is reacted with a chloro-heterocycle in the presence of a base to give a compound of Formula 95.

Scheme VII

According to Scheme VII, compounds wherein —G—E— is —CH($R_5$)—S— are prepared by reacting a compound of Formula 93, whose preparation is illustrated in Scheme V, with a thiol-substituted heterocycle in the presence of a base to give a compound of Formula 96.

Scheme VIII

According to Scheme VIII, compounds wherein —G—E— is —CH$_2$—CH($R_5$)— are prepared by reacting a heterocyclic aldehyde of Formula 97 with a Wittig reagent (CH$_2$=P(Ph)$_3$) to yield vinyl-heterocycle 98. Olefin epoxidation with m-chloroperoxybenzoic acid affords epoxide 99. Epoxide 99 is opened with a Grignard reagent 100 prepared from the corresponding bromo compound. The resulting alcohol 101 is oxidized (e.g., Swern oxidation) to afford ketone 102. The ketone is reacted with the desired Wittig reagent (e.g., Pr—P(Ph)$_3$) to give an intermediate olefin which is reduced with hydrogen in the presence of a catalyst (e.g., platinum or palladium) to afford a compound of Formula 103.

Scheme IX

According to Scheme IX, compounds wherein —G—E— is —CH($R_5$)—CH$_2$— are prepared by converting an aldehyde of Formula 91 to a halo-alkylated compound of the Formula 93A (X' is halogen). Compound 93A is converted into Wittig reagent 110 using triphenylphosphine and a suitable base. This Wittig reagent is reacted with heterocyclic aldehyde 97 to give a compound of Formula 111. This olefin is reduced with hydrogen in the presence of a catalyst such as platinum or palladium to give a compound of the Formula 112.

Scheme X

According to Scheme X, compounds wherein —G—E— is —N($R_5$)—CH$_2$— are prepared by alkylating amine 82 with $R_5$Cl in the presence of a base. The resulting amine 82a is reductively aminated with aldehyde 97 to give a compound of the Formula 114.

Scheme XI

According to Scheme XI, compounds wherein —G—E— is —NH—CH($R_5$)— are prepared by reacting a heterocyclic nitrile 115 with an alkyl Grignard reagent (e.g., propylmagnesium bromide) and then hydrolyzing the intermediate imine to give a ketone of Formula 116. Reductive amination with an amino compound of Formula 82 yields a compound of the Formula 117.

Scheme XII

According to Scheme XII, compounds wherein —G—E— is —O—CH($R_5$)— are prepared by reacting a heterocyclic aldehyde with an organometallic reagent (e.g., $R_5$-M is propylmagnesium bromide) to produce a secondary alcohol of Formula 120. The alcohol is converted to a leaving group (for example, mesylate) and then is coupled with an alcohol Q—OH in the presence of a base to afford a compound of Formula 121.

Scheme XIII

According to Scheme XIII, compounds wherein —G—E— is —S—CH($R_5$)— are prepared by converting a secondary alcohol to a leaving group (e.g., X' is mesylate) and then displacing it with a thiol of Formula 85 in the presence of a base to afford a compound of Formula 123.

Scheme XIV

According to Scheme XIV, compounds wherein —G—E— is —NH—N($R_5$)— are prepared by converting an amine of Formula 82 into a urea 124. The urea is reacted with bromine in the presence of a base to yield hydrazine 125. Alkylation with an alkyl bromide (e.g., $R_5$X' is propyl bromide), followed by displacement of a chloro heterocycle with the secondary amine 125, affords a compound of Formula 126.

Scheme XV

According to Scheme XV, compounds wherein —G—E— is —N($R_5$)—NH— are prepared by first converting amine 82a to urea 130. Urea 130 is converted to hydrazine 131 by treatment with bromine in base. Hydrazine 131 is reacted with chloro-heterocycle D-Cl to afford a compound of Formula 132.

SCHEME I

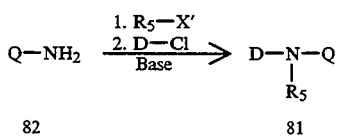

SCHEME II

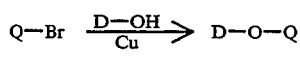

SCHEME III

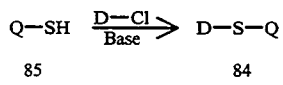

SCHEME IVA

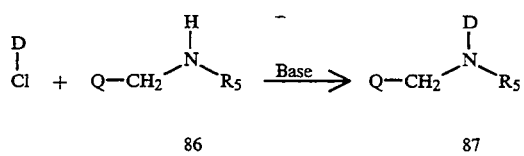

SCHEME IVB

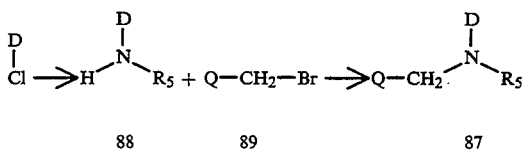

SCHEME V

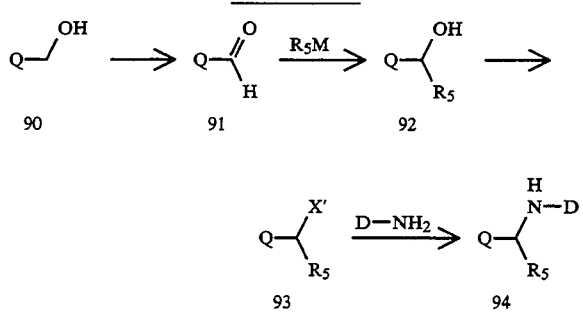

SCHEME VIA

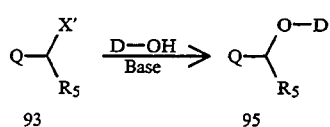

SCHEME VIB

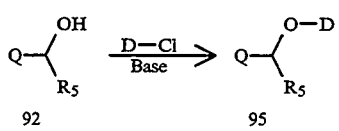

SCHEME VII

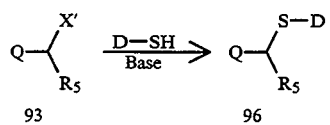

SCHEME VIII

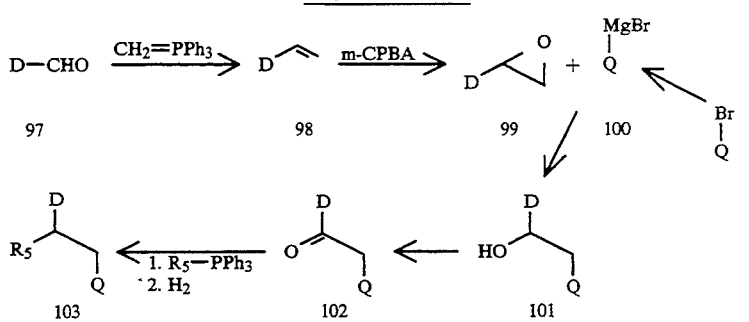

SCHEME IX

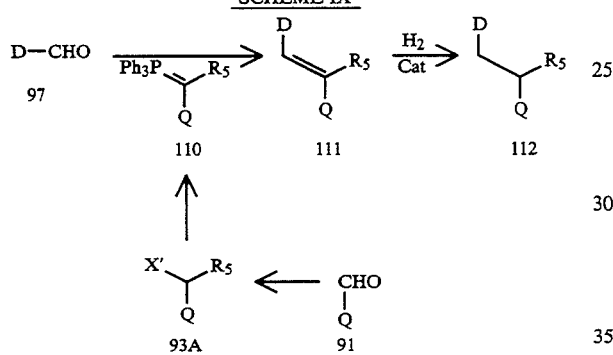

SCHEME X

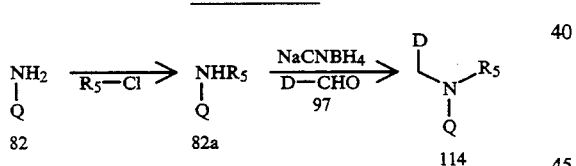

SCHEME XI

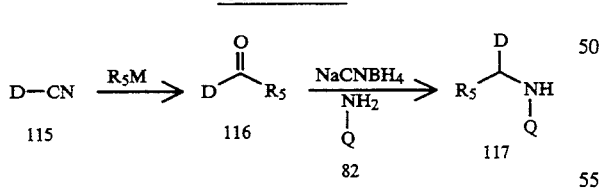

SCHEME XII

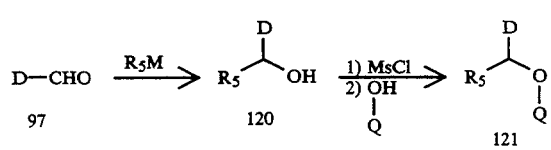

SCHEME XIII

-continued

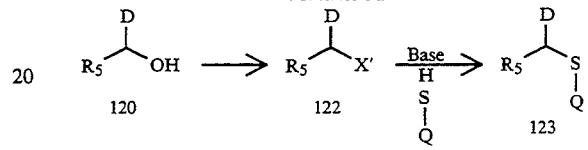

SCHEME XIV

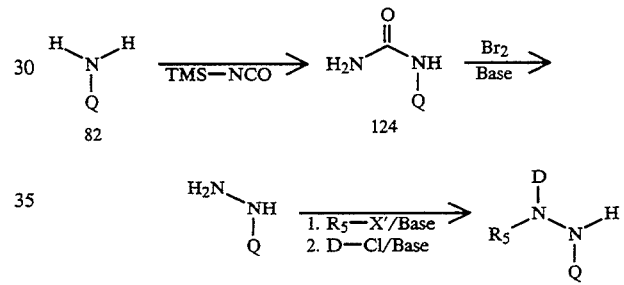

SCHEME XV

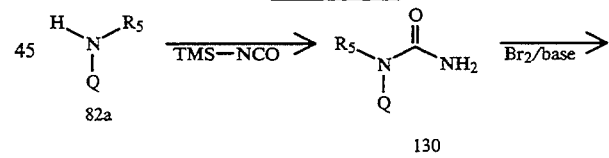

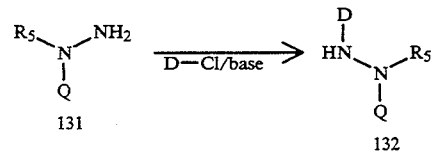

Schemes XVI–XXII illustrate the preparation of representative compounds of the invention;

Scheme XVI

Reaction Scheme XVI illustrates a method of preparing 2-{N-propyl-N-[(6-[1H-tetrazol-5-yl]naphthyl-2-yl)methyl]amino}pyridine-3-carboxylic acid. Secondary amine 140 is alkylated with bromomethylnaphthalene 141, prepared by the method of Buhlmayer in J. Med. Chem. 34, 3105 (1991), in the presence of base to give tertiary amine 142. The nitrile of 142 is transformed into a tetrazole using trimethyl tin azide and then the methyl ester is hydrolyzed with base to give a compound of Formula 143.

Scheme XVII

Reaction Scheme XVII illustrates a method of preparing 2-{N-propyl-N-[(1,2,3,4-tetrahydro-2-carboxynaphthyl-6-yl)methyl]amino}pyridine-3-carboxylic acid. Secondary amine 140 is alkylated with tetrahydronaphthalene 144, prepared by the method of Buhlmayer in J. Med. Chem. 34, 3105 (1991), in the presence of a base to give a tertiary amine the ester of which is hydrolyzed with base to give a compound of Formula 145.

Scheme XVIII

Reaction Scheme XVIII illustrates a method of preparing 2-{N-propyl-N-[(2-(2-[1H-tetrazol-5-yl]phenyl)-1,3,4-oxadiazol-5-yl)methyl]amino}pyridine-3-carboxylic acid. Cyanobenzoic acid methyl ester 150 is reacted with hydrazine followed by triethyl orthoacetate to give substituted oxadiazole 151 (Orlek, J. Med. Chem. 34, 2729 (1991)). Bromination with N-bromosuccinimide gives a compound of Formula 152. Treatment of 152 with secondary amine 140 in the presence of base gives a tertiary amine of Formula 153. The nitrile is converted to a tetrazole with trimethyl tin azide and then the methyl ester is hydrolyzed with base to give a compound of Formula 154.

Scheme XIX

Scheme XIX illustrates a method of preparing 2-{N-propyl-N-[(2-carboxymethylamino-benzimidazole-5-yl)methyl]amino}pyridine-3-carboxylic acid. 3,4-Diaminobenzoic acid 160 is converted to Cbz-protected aminobenzimidazole 161 (Ram, J. Med. Chem. 35, 539 (1992)). The acid is reduced to aldehyde 162 via the Rosemund procedure. The aldehyde is reductively aminated with secondary amine 140 to give tertiary amine 163. The Cbz-group is removed and the primary amine is alkylated with bromoacetate to give the compound of Formula 164. Ester hydrolysis catalyzed by base gives a compound of Formula 165.

Scheme XX

Scheme XX illustrates a method of preparing 5-phenyl-2-{N-propyl-N-[(substituted-phenyl)methyl]amino}pyridine-4-carboxylic acid. The reaction of 3,5-dichloro-1,6-diphenyl-pyrazin-2-one 170 with ethyl propiolate by the procedure described in Tetrahedron Lett.27, 2509 (1986) gives a compound of the Formula 171. Treatment of this dichloro compound with compound 172 with heating in the presence of a base affords tertiary amine 173. This compound is dechlorinated using palladium on carbon catalyst under hydrogen in the presence of triethylamine to give a compound of Formula 174. A tetrazole, if present, is deprotected, and the ester is hydrolyzed to give a compound of Formula 175.

Scheme XXI

Scheme XXI illustrates a method of preparing 2-N-(4-[4-(benzo[d]isothiazolyl-3-one-1,1-dioxide)benzyl)-N-propyl}aminopyridine-3-carboxylic acid. A compound of Formula 180 is reacted with phosgene and diethylamine to give an amide of Formula 181. Treatment of 181 with sec-butyl lithium followed by sulfur dioxide and then aminosulfate gives a compound of Formula 182. Treatment of 182 with acetic acid gives the cyclized compound 183 (Hlasta, Tetrahedron Lett. 32 (49), 7179 (1991)). Compound 183 is protected with trityl chloride and then brominated with N-bromosuccinimide to give bromo compound 184. Compound 184 is coupled with alkylamino pyridine carboxylate 185 under basic conditions to give a tertiary amine of Formula 186. Formic acid detritylation followed by basic ester hydrolysis affords a compound of Formula 187.

Scheme XXII

Scheme XXII illustrates a method of preparing (E)-3-{2-[N-propyl-N-(4-carboxybenzyl)amino]-3-pyridyl}-2-(2-thienylmethyl)acrylic acid. 2-Amino-3pyridine carboxaldehyde, prepared by the method described in Syn. Comm. 17(14), 1695 (1987), is treated with base and then alkylated with allyl bromide to give the N-allyl compound. Catalytic hydrogenation affords the N-propyl amine 191. Treatment with base followed by bromo compound 192 affords tertiary amine 193. Using the procedure of Weinstock, J. Med. Chem. 34(4), 1514 (1991), the aldehyde is reacted with thienyl compound 194 to give compound 195 which is hydrolyzed using potassium hydroxide in ethanol to give a compound of Formula 196.

Scheme XXIII

Scheme XVI illustrates the preparation of pyrrolophenyl compounds 206 (wherein R3' is halogen). Reaction of methyl aniline with dimethoxytetrahydrofuran in acetic acid gives the coupled compound 200. Treatment of 200 with chlorosulfonyl isocyanate gives the cyano compound 201. Bromination with N-bromosuccinimide gives the bromo compound 202. Treatment of 202 with N-bromosuccinimide in the presence of a radical initiator such as AIBN gives the dibromo compound 203. Reaction of the bromomethyl compound with R5NH2 gives the secondary amine 204. Treatment of the secondary amine with a 2-chlorinated pyridine carboxylic ester gives the tertiary amine 205. The nitrile functionality is converted to a tetrazole 206A using trimethyltin chloride and sodium azide. In the final step the ester is hydrolyzed with sodium hydroxide to give the carboxylic acid 206B.

Other substituted pyrrolo compounds or the analogous thienyl or furyl compounds can be prepared according to methods analogous to those disclosed in EP480204 (published Apr. 15, 1992) or by methods well known in the art.

Scheme XXIV

Alternatively, as shown in Scheme XXIV, reaction of 203 with amino-substituted nicotinate 207 provides 205.

SCHEME XVI

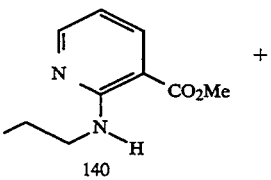

5,364,869
69
-continued
SCHEME XVI
70
SCHEME XVII
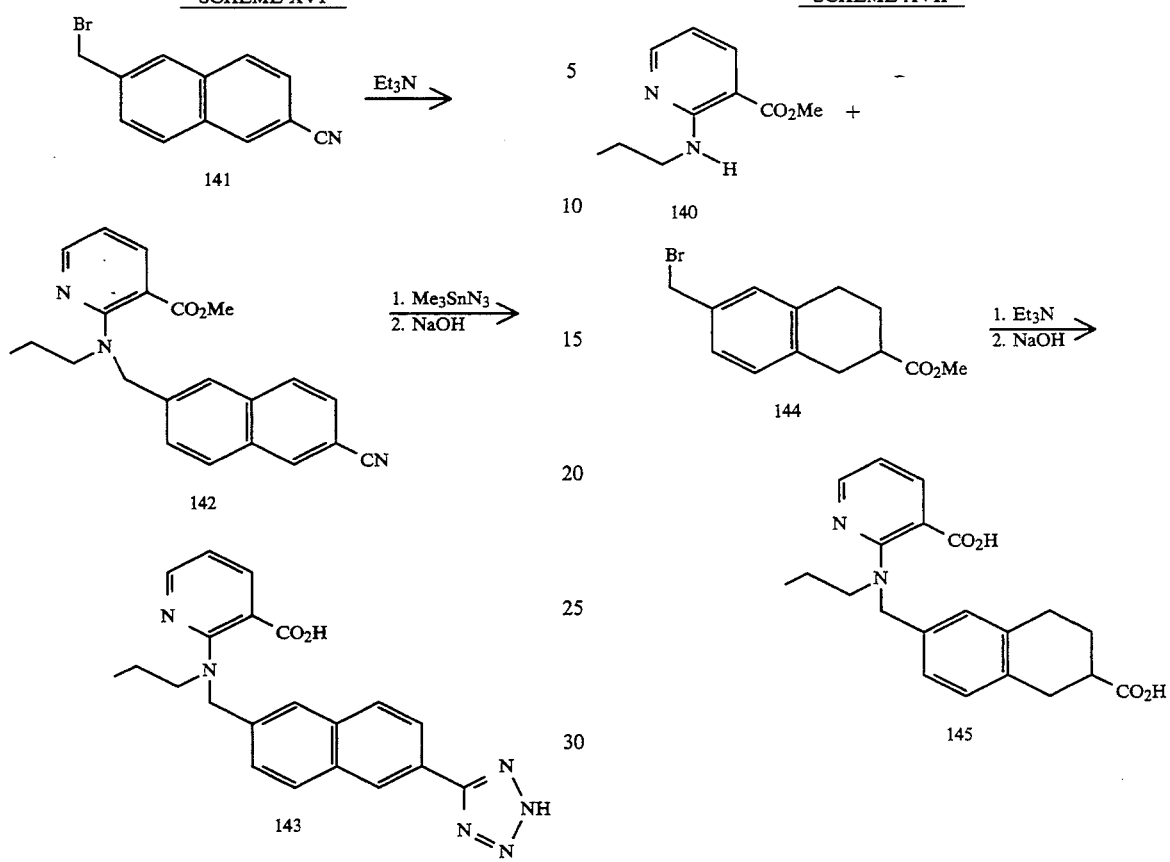
SCHEME XVIII
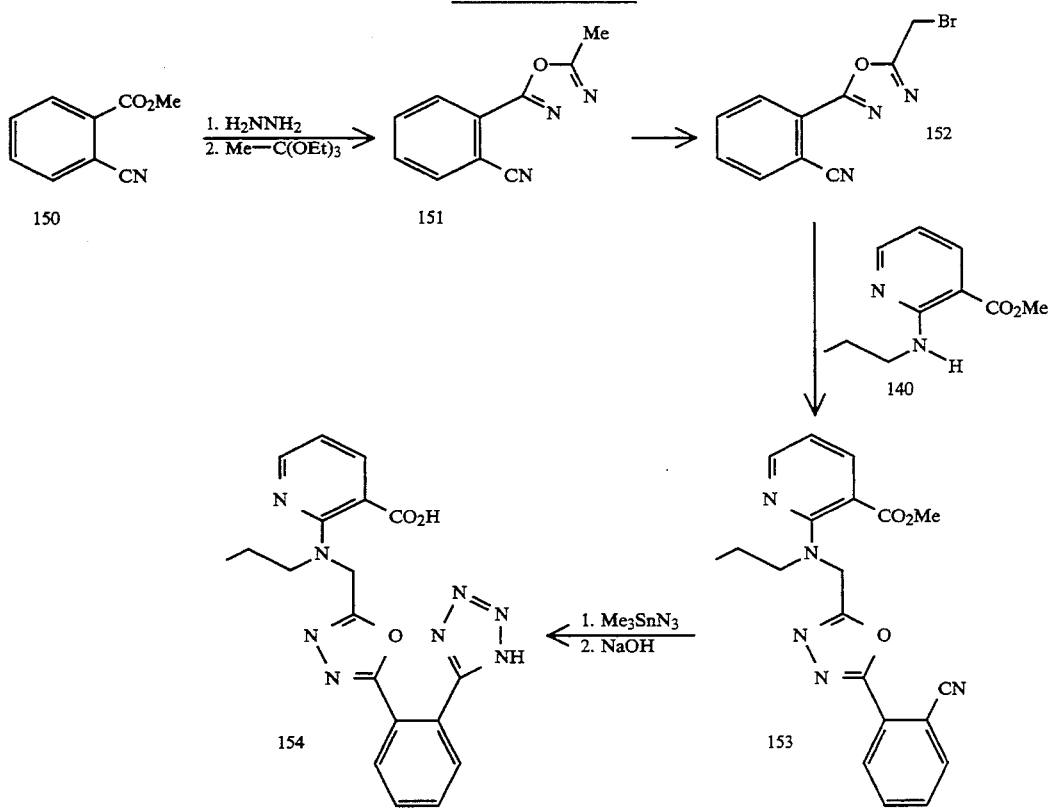

SCHEME XIX
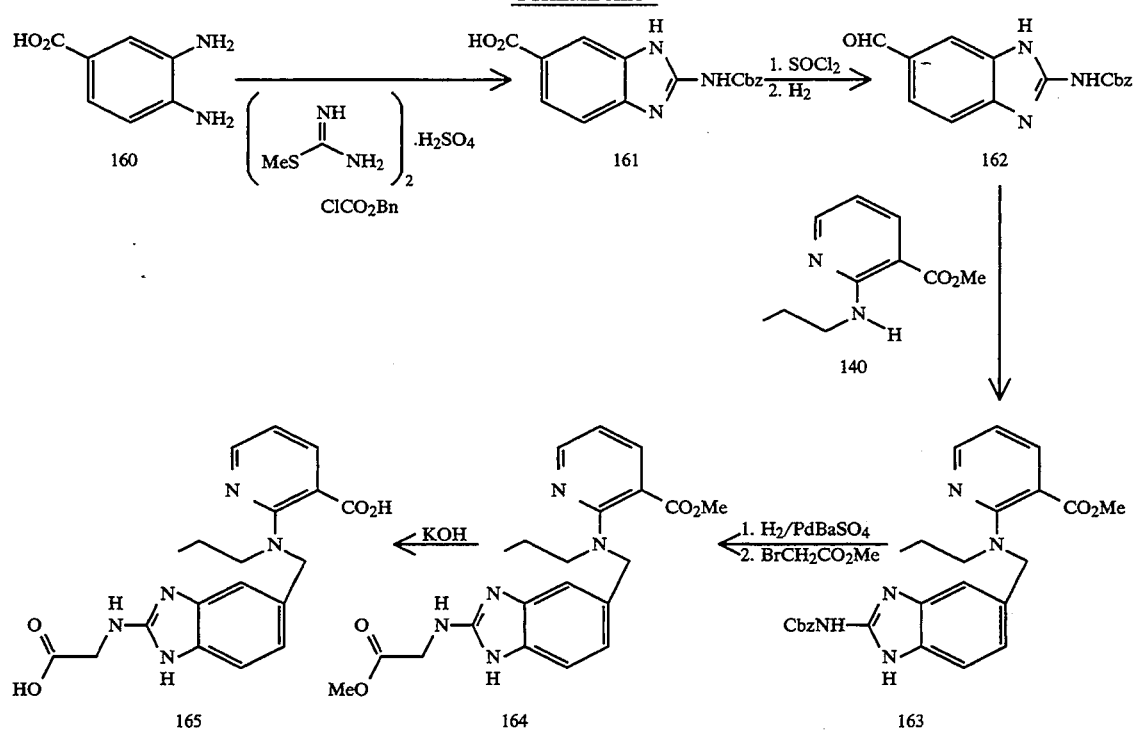
SCHEME XX
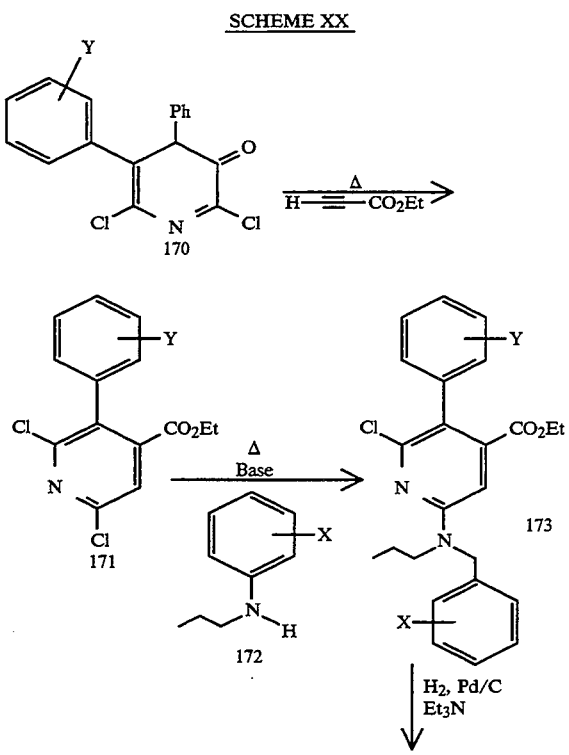
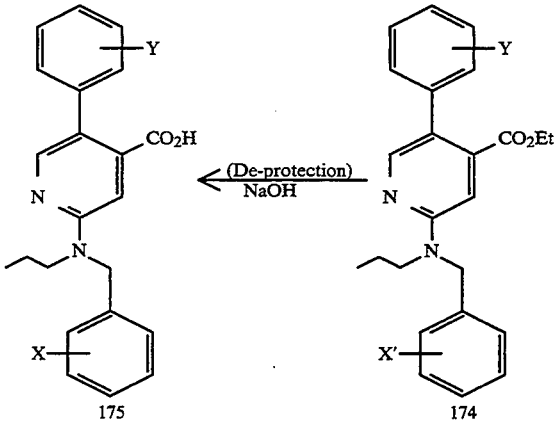
X' = CO$_2$Me, NHSO$_2$CF$_3$, 
X = CO$_2$H, NHSO$_2$CF$_3$, 
Y = H, OR, Halogen, Alkyl, CO$_2$R', NHR"

SCHEME XXI
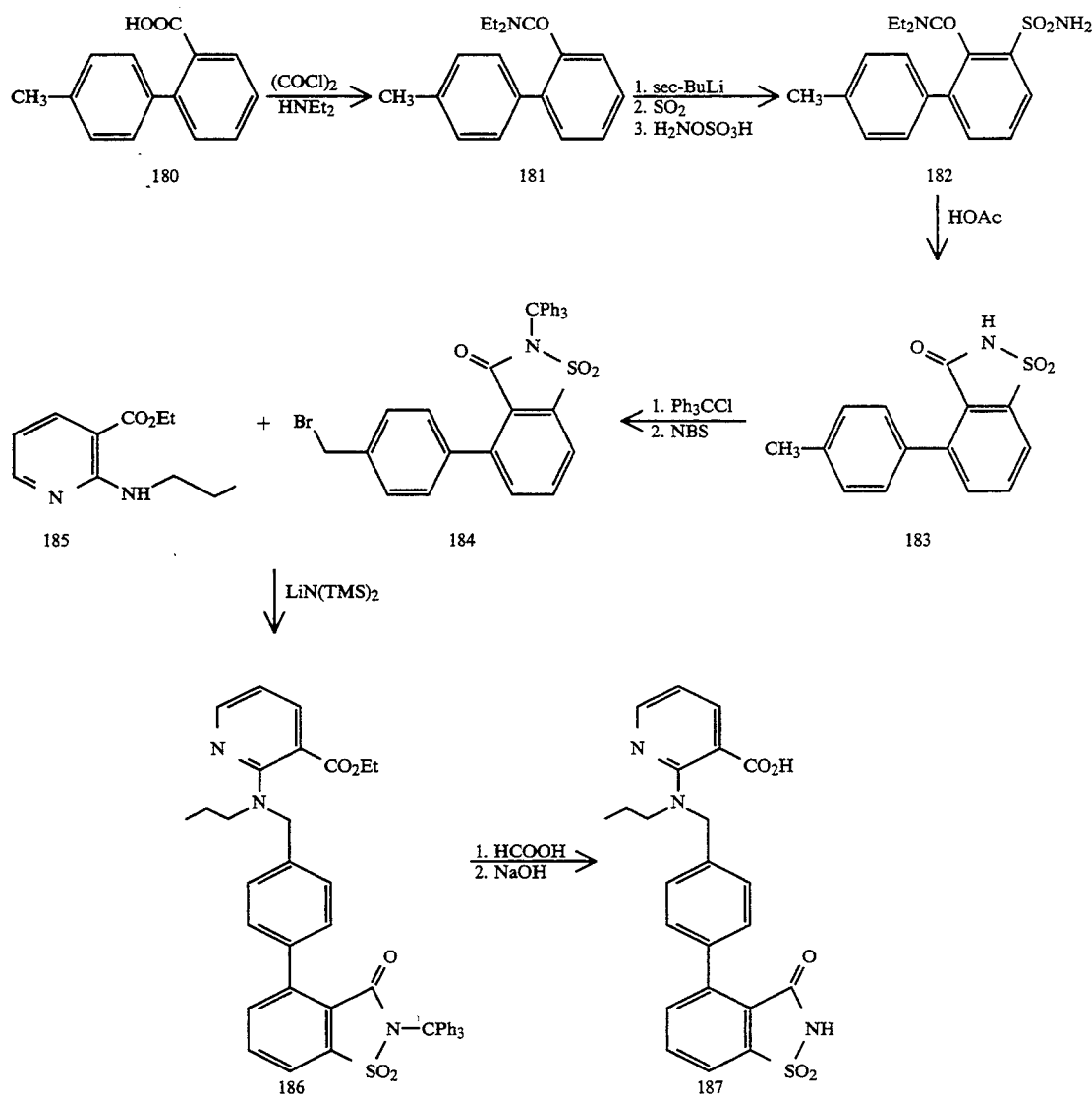
SCHEME XXII
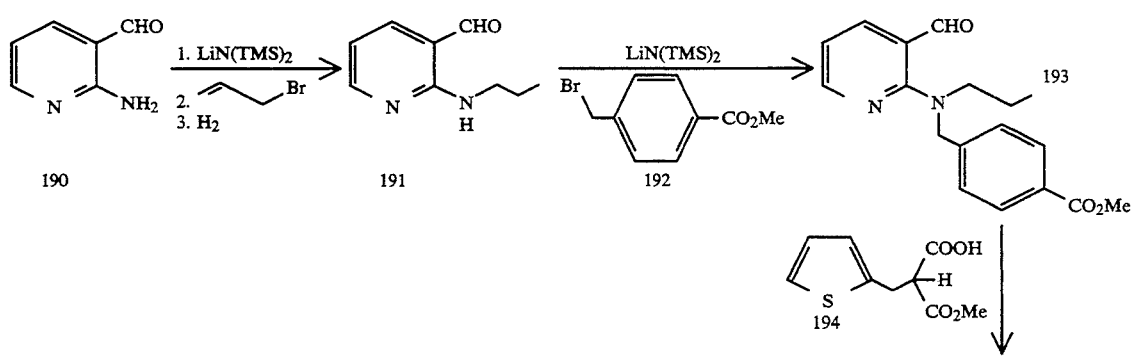

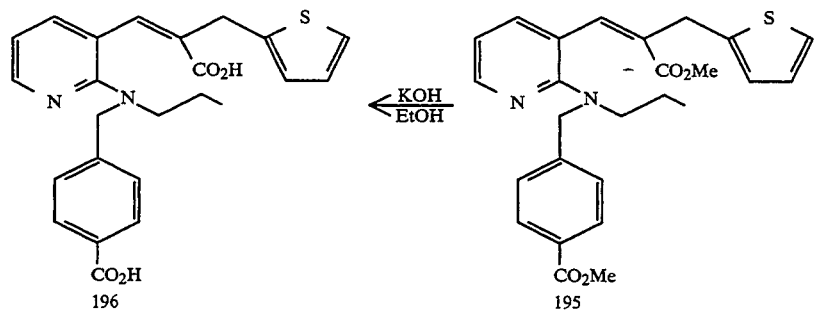
-continued
SCHEME XXII
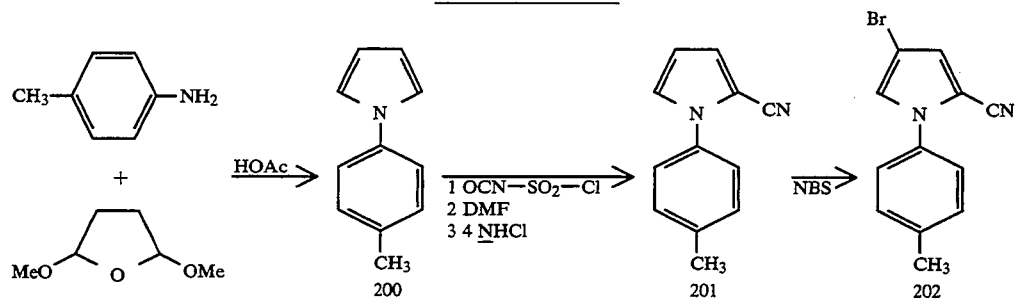
SCHEME XXIII
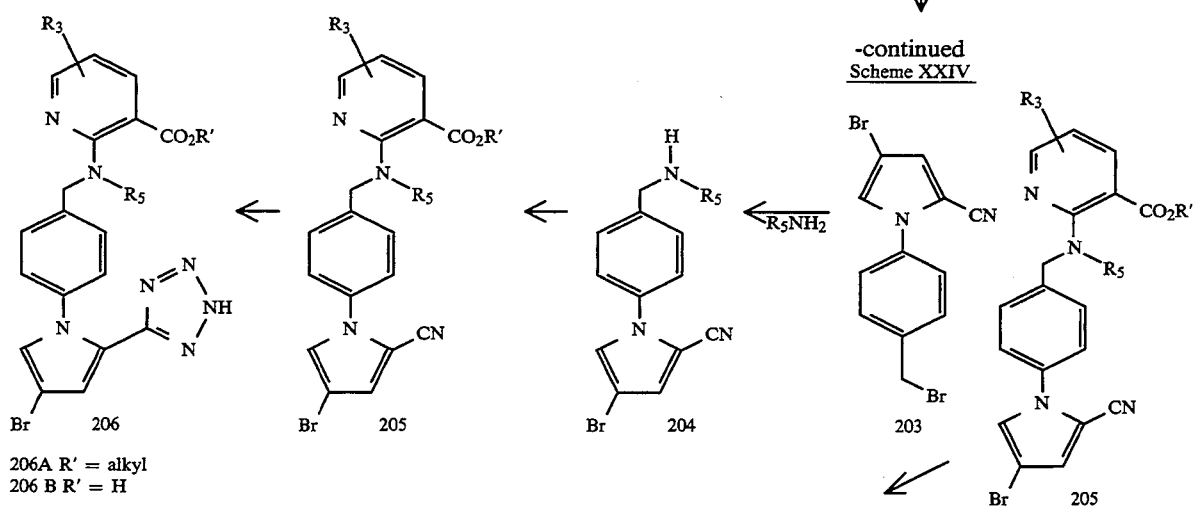
-continued
Scheme XXIV
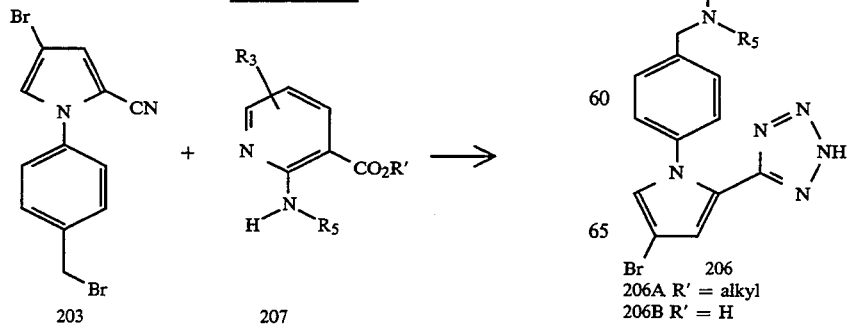
Scheme XXIV Useful intermediates for the preparation of the more preferred compounds of the invention are compounds of the formula:

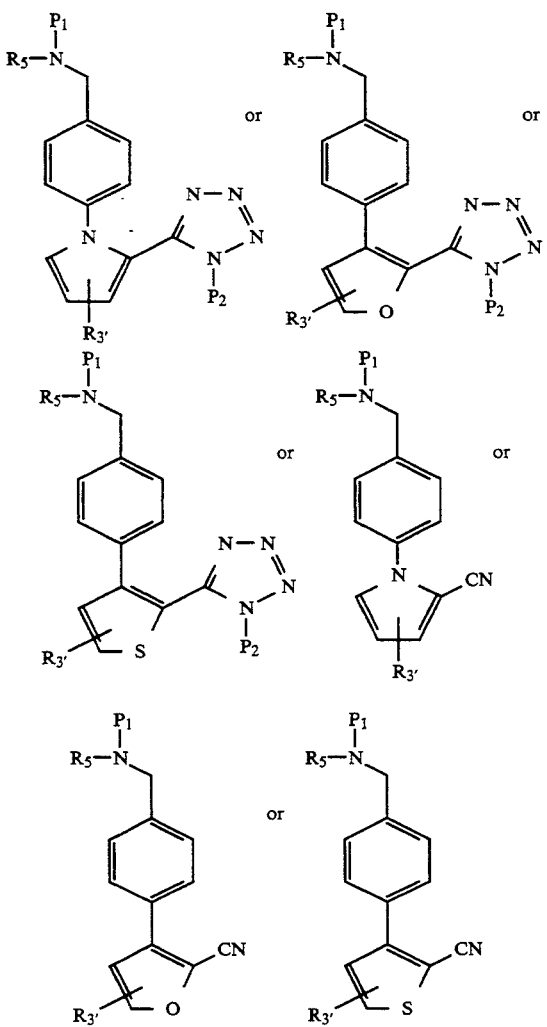

wherein $P_1$ is hydrogen or an N-protecting group; $P_2$ is hydrogen or an N-protecting group; $R_{3'}$ is hydrogen, loweralkyl or halo; and $R_5$ is hydrogen, loweralkyl, alkoxy-substituted loweralkyl, halo-substituted loweralkyl, alkenyl, alkynyl, cycloalkyl or cycloalkylalkyl; or a salt thereof.

Useful intermediates for the preparation of the most preferred compounds of the invention are compounds of the formula:

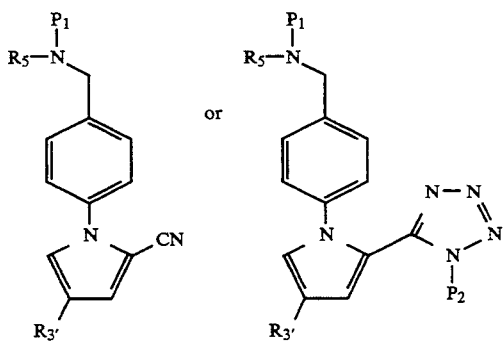

wherein $P_1$ is hydrogen or an N-protecting group; $P_2$ is hydrogen or an N-protecting group; $R_{3'}$ is hydrogen, loweralkyl or halo; and $R_5$ is hydrogen, loweralkyl, alkoxy-substituted loweralkyl, halo-substituted loweralkyl, alkenyl, alkynyl, cycloalkyl or cycloalkylalkyl; or a salt thereof.

The foregoing may be better understood from the following examples, which are presented for the purpose of illustration and not intended to limit the scope of the inventive concept.

EXAMPLE 1

4-[N-4-(1-Carboxy-1-phenylmethoxy)benzyl-N-propyl-]amino-2-methylpyrimidine-5-carboxylic acid

Example 1A

4-Propylaminomethylphenol

Propylamine (4.13 g) was slowly added to 4-hydroxybenzaldehyde (11.2 g, 91.80 mmol) in 50 mL of isopropanol at ambient temperature. The reaction was stirred for 1 hour and then cooled in an ice bath to 0° C. The imine was then reduced with sodium borohydride (1.74 g, 46 mmol) for 1 hour. The reaction was diluted with 100 mL of ethanol and acidified with acetic acid. The resulting solid was filtered and recrystallized from ethanol/isopropanol to give 15.1 g (99%) of the title compound. TLC (3:1 ethyl acetate/ethanol, trace triethylamine) $R_f = 0.37$.

Example 1B

Ethyl 4-[N-4-hydroxybenzyl-N-propylamino-2-methylpyrimidine-5-carboxylate

A solution of the compound resulting from Example 1A (2.81 g, 17 mmol), ethyl 4-chloro-2-methylpyrimidine-5-carboxylate (3.4 g, 1. equivalent) and triethylamine (4.7 mL, 2 equivalents) in 10 mL of dimethylformamide was stirred at ambient temperature overnight. The reaction mixture was partitioned between ethyl acetate and water. The crude product was purified by column chromatography on silica gel to afford 2.93 g (52%) of the title compound. TLC (ethyl acetate) $R_f = 0.32$.

Example 1C

Ethyl 4-[N-4-(1-methoxycarbonyl-1-phenylmethoxy)benzyl-N-propylamino-2-methylpyrimidine-5-carboxylate 60% Oil dispersion sodium hydride (220 mg) was added to a solution of the compound resulting from Example 1B (1.51 g, 4.58 mmol) dissolved in 10 mL of dimethylformamide at 0° C. After stirring for 10 minutes, methyl 2-bromo-2-phenylacetate (1.05 g) was added. The reaction was stirred at ambient temperature for 6 hours and then quenched with ethyl acetate and ammonium chloride solution. The crude reaction mixture was purified by column chromatography to give 1.61 g (73%) of the title compound. TLC (ethyl acetate) $R_f = 0.53$.

Example 1D

4-[N-4-(1-Carboxy-1-phenylmethoxy)benzyl-N-propylamino-2-methylpyrimidine-5-carboxylic acid The compound resulting from Example 1C (1.42 g, 2.97 mmol) was dissolved in 5 mL of ethanol and 5 mL of dioxane and hydrolyzed with aqueous sodium hydroxide (5 equivalents) in 2 mL of water at ambient temperature for 15 hours. The resulting sodium salt was acidified with 6N hydrochloric acid and the resulting diacid purified by column chromatography (650 mg, 50%). TLC (16:2:2 ethyl acetate/formic acid/water) $R_f$=0.50. $^1$H NMR (DMSO-d$_6$, 300 MHz) d 0.72 (t, J=7 Hz, 3H), 1.50 (q, J=7 Hz, 2H), 2.40 (s, 3H), 3.32 (t, J=7 Hz, 2H), 4.72 (s, 2H), 5.78 (s, 1H), 6.90 (d, J=8 Hz, 2H), 7.17 (d, J=8 Hz, 2H), 7.38 (m, 3H), 7.54 (d, J=7 Hz, 2H), 8.39 (s, 1H). MS (DCI/NH$_3$) m/e 436 (M+H)+.

EXAMPLE 2

Methyl 4-{N-propyl-N-[(3-bromo-2-[2-(1H-tetrazol-5-yl)phenyl]benzo[6]thiophenyl-6-yl)methylamino}pyridine-3-carboxylate

Example 2A

3-Bromo-2-(2-cyanophenyl)-6-propylaminomethylbenzo[6]thiophene

3-Bromo-6-bromomethyl-2-(2-cyanophenyl)benzo[6]thiophene, prepared following a procedure described in European Patent Application 0430709 A2, (1.45 g, −80% pure) was dissolved in 20 mL of isopropyl alcohol and 5 mL of methylene chloride and reacted with 10 mL of n-propylamine at ambient temperature for 1 hour. The solvent was removed under reduced pressure, and the crude reaction mixture was diluted with methylene chloride and brine. The organic phase was dried and concentrated in vacuo. The residue obtained was purified by silica gel chromatography to give 700 mg of the desired product. TLC (ether) $R_f$=0.09.

Example 2B

Methyl 4-{N-propyl-N-[(3-bromo-2-(2-cyanophenyl)-benzo[6]-thiophenyl-6-yl)methyl]amino}pyridine-3-carboxylate A solution of the compound resulting from Example 2A (402 mg, 1.04 mmol) and methyl 2-chloropyridine-3-carboxylate (1.02 g, 5.7 equivalents) in 1 mL of diisopropylethylamine was heated at reflux for 1.5 hours. The crude reaction mixture was directly purified by column chromatography to give 252 mg (46%) of the desired coupled product. TLC (ethyl acetate) $R_f$=0.76.

Example 2C

Methyl 4-{N-propyl-N-[(3-bromo-2-[2-(1H-tetrazol-5-yl)phenyl]-benzo[6]thiophenyl-6-yl)methyl]amino}pyridine-3-carboxylate A suspension of the compound resulting from Example 2B (252 mg, 0.48 mmol), trimethyl tin chloride (200 mg, 1.5 equivalents) and sodium azide (65 mg, 1.5 equivalents) in 3 mL of toluene was heated at reflux for 15 hours. The solution was cooled to ambient temperature, diluted with hexane and filtered. The solid obtained was washed with water and then dissolved in a solution of hydrogen chloride in ethanol. After removal of the solvent under reduced pressure, the product was purified by recrystallization from ethanol and isopropanol to afford 248 mg of the title compound. TLC (1:1 ether-/ethyl acetate containing 1% acetic acid) $R_f$=0.53.

EXAMPLE 3

4-{N-Propyl-N-[(3-bromo-2-[2-(1H-tetrazol-5-yl)phenyl]-benzo[6]thiophenyl-6-yl)methyl]amino}pyridine-3-carboxylic acid The compound resulting from Example 2 (190 mg, 0.33 mmol) was dissolved in 4 mL of dioxane and 2 mL of ethanol and reacted with excess aqueous sodium hydroxide solution (12 equivalents in 1.5 mL of water) at 60° C. for 6 hours. The reaction was acidified with aqueous hydrochloric acid and the product was (109 mg, 60%) was purified by column chromatography on silica gel eluting with 5% formic acid in ethyl acetate to afford the title compound. TLC (16:2:2 ethyl acetate/-formic acid/water) $R_f$=0.56. $^1$H NMR (DMSO-d$_6$, 300 MHz) d 0.74 (t, J=8 Hz, 3H), 1.55 (q, J=8 Hz, 2H), 3.30 (m, 2H), 4.85 (s, 2H), 6.80 (dd, J=5 Hz, 7 Hz, 1H), 7.40 (d, J=9 Hz, 1H), 7.70 (m, 4H), 7.90 (m, 3H), 8.25 (dd, j=1 Hz, 5 Hz, 1H).

EXAMPLE 4

2-{N-Propyl-N-[(1-[3-bromo-5-(1H-tetrazol-5-yl)pyrrole-1-yl]phenyl-4-yl)methyl]amino}pyridine-3-carboxylic acid

Example 4A

1-(4-Methylphenyl)pyrrole

The title compound was prepared in analogy to the procedure described in European Patent Application 480204. 4-Methylaniline (30 g, 280 mmol), 2,5-dimethoxytetrahydrofuran (22 g, 166 mmol) and acetic acid (200 mL) were combined under a nitrogen atmosphere and heated at −100° C. for 90 minutes. The solvent was removed under reduced pressure and the residue obtained suspended in hexane and filtered. The filtrate was passed through a pad of silica gel and concentrated in vacuo. The residue obtained was crystallized from methanol to afford 10.6 g (45%) of the title compound. MS (DCI/NH$_3$) m/e 158 (M+H)+.

Example 4B

1-(4-Methylphenyl)pyrrole-2-carbonitrile

The title compound was prepared in analogy to the procedure described in European Patent Application 480204. Chlorosulfonyl isocyanate (7.20 mL) in methylene chloride (50 mL) was slowly added to a solution of the compound resulting from Example 4A (10.1 g, 64.33 mmol) in 100 mL of methylene chloride at 0° C. over 30 minutes. The reaction mixture was stirred at ambient temperature for 1 hour and then cooled back to 0° C. DMF (10 mL) was added and stirring was continued at 0° C. for 30 minutes. After stirring at ambient temperature for 1 hour, the solution was cooled back to 0° C and treated with 4 N hydrochloric acid. The solution was diluted with hexane-ethyl acetate and washed with brine. The organic solution was dried over magnesium sulfate and concentrated under reduced pressure. The residue obtained was purified by silica gel chromatography to afford 7.82 g (66%) of the title compound. MS (DCI/NH$_3$) m/e 200 (M+H+NH$_3$)+.

Example 4C

3-Bromo-1-(4-methylphenyl)pyrrole-5-carbonitrile

To a solution of the compound resulting from Example 4B (8.4 g, 46.15 mmol) in 150 mL of THF was added N-bromosuccinimide (11.72 g, 65.84 mmol, 1.4 equivalents) in portions. The reaction mixture was stirred at ambient temperature for 3 hours and then the solvent was removed under reduced pressure. The residue obtained was diluted with ether, the solution filtered and the filtrate concentrated in vacuo. The residue obtained was chromatographed on silica gel eluting with a 4:1 mixture of hexane-ethyl acetate to give 12.92 g of the title compound. MS (DCI/NH$_3$) m/e 278, 280 (M+H+NH$_3$)$^+$.

Example 4D

3-Bromo-1-(4-bromomethylphenyl)pyrrole-5-carbonitrile

The title compound was prepared in analogy to the procedure described in European Patent Application 480204. To the compound resulting from Example 4C (5.85 g, 22.41 mmol) dissolved in 50 mL of carbon tetrachloride was added N-bromosuccinimide (4.78 g, 26.89 mmol) and azo(bisisobutyronitrile) (AIBN) (50 mg). The reaction mixture was heated at reflux for 2.5 hours, cooled to ambient temperature, and diluted with water-methylene chloride. The organic phase was dried, concentrated in vacuo and purified by column chromatography on silica gel eluting with 1:5 ethyl acetate-hexane to give 5.98 g of the title compound. MS (DCI/NH$_3$) m/e 358, 360 (M+H+NH$_3$)$^+$.

Example 4E

3-Bromo-1-(4-propylaminomethylphenyl)pyrrole-5-carbonitrile

To the compound resulting from Example 4D (5.98 g, 17.58 mmol) dissolved in 60 mL of anhydrous THF was added 15 ml (169 mmol, −10 equivalents) of n-propylamine. The reaction mixture was stirred for 3 hours at ambient temperature and then heated at 60° C. for 1 hour. After cooling to ambient temperature, the solvent was removed under reduced pressure and the residue obtained chromatographed on silica gel eluting with 1:4 ethyl acetate-hexane containing −1-5% triethylamine to afford 2.1 g (37%) of the title compound. MS (DCI/NH$_3$) m/e 318, 320 (M+H)$^+$.

Example 4F

Methyl 2-{N-propyl-N-[(1-[3-bromo-5-cyanopyrrole-1-yl]phenyl-4-yl)methyl]amino}pyridine-3-carboxylate The compound resulting from Example 4E (2 g, 6.28 mmol), methyl 2-chloropyridine-3-carboxylate (2.16 g, 12.57 mmol) and 2 mL of diisobutylethylamine (2 mL) were dissolved in 10 mL of toluene and heated at reflux for 5 hours. The reaction mixture was allowed to cool to ambient temperature and diluted with water and a mixture of ethyl acetate in hexane. The aqueous phase was extracted with an additional portion of ethyl acetate in hexane. The combined organic extracts were dried and concentrated in vacuo. The residue obtained was purified by chromatography on silica gel eluting with 1:6 ethyl acetate-hexane to give 1.42 g of the title compound. MS (DCI/NH$_3$) m/e 455, 457 (M+H)$^+$.

Example 4G

Methyl 2-{N-propyl-N-[(1-[3-bromo-5-(1H-tetrazol-5-yl)pyrrole-1-yl]phenyl-4-yl)methyl]amino}pyridine-3-carboxylate To the compound resulting from Example 4F (1.40 g, 3.09 mmol) dissolved in 5 mL of xylene was added trimethyltin chloride (1.5 g, 4.6 mmol) and sodium azide (300 mg, 4.6 mmol). The reaction mixture was heated at reflux for 2 hours, allowed to cool to ambient temperature and treated with 0.5 mL of 85% formic acid and 50 mL of hexane. The mixture was slurried in water and ethyl acetate and the aqueous phase extracted with additional ethyl acetate. The combined organic extracts were dried, concentrated in vacuo and the resulting residue purified by column chromatography on silica gel eluting with −5% formic acid in ethyl acetate to afford 2.1 g of the title compound. MS (DCI/NH$_3$) m/e 496, 498 (M+H)$^+$.

Example 4H

2-{N-Propyl-N-[(1-[3-bromo-5-(1H-tetrazol-5-yl)pyrrole-1-yl]phenyl-4-yl)methyl]amino}pyridine-3-carboxylic acid To the compound resulting from Example 4G (2.1 g) dissolved in 25 mL of ethanol at ambient temperature was added 2.00 g of sodium hydroxide in 10 mL of water. The reaction mixture was stirred overnight at ambient temperature and then acidified with 8 mL of 6N hydrochloric acid. The solvent was removed under reduced pressure and the residue obtained purified by column chromatography on silica gel eluting with 3% formic acid in ethyl acetete. The residue obtained was crystallized from ethyl acetate-hexane to give 1.1 g (73%) of the title compound. $^1$H NMR (DMSO-d$_6$, 300 MHz) δ0.74 (t, 3H), 1.55 (m, 2H), 3.26 (m, 2H), 4.76 (s, 2H), 6.80 (dd, 1H), 6.97 (d, 1H), 7.22 (m, 2H), 7.37 (m, 2H), 7.50 (d, 1H), 7.88 (dd, 1H), 8.23 (dd, 1H). MS (DCL/NH$_3$) m/e 482, 484 (M+H)$^+$. Anal calcd for C$_{21}$H$_{20}$BrN$_7$O$_2$. 0.25 ethyl acetate: C, 52.39; H, 4.40; N, 19.44. Found: C, 52.37; H, 4.39; N, 19.20.

The compounds of the present invention can be used in the form of salts derived from inorganic or organic acids. Pharmaceutically acceptable salts are described in Berge, et al., *J. Pharmaceutical Sciences* 66 1-19 (1977). These salts include but are not limited to the following: acetate, adipate, alginate, citrate, ascorbate, aspartate, benzoate, benzenesulfonate, bisulfate, borate, butyrate, camphorate, camphorsulfonate, citrate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxyethanesulfonate, lactobionate, lactate, laurate, lauryl sulfate, maleate, methanesulfonate, nicotinate, 2-naphthalenesulfonate, oleate, oxalate, palmitate, pamoate, pectinate, persulfate, phosphate, 3-phenyl-propionate, picrate, pivalate, propionate, stearate, succinate, tartrate, thiocyanate, toluenesulfonate (tosylate), undecanoate and valerate. Examples of acids which can be employed to form pharmaceutically acceptable acid addition salts include such inorganic acids as hydrochloric acid, sulphuric acid and phosphoric acid and such organic acids as oxalic acid, maleic acid, succinic acid, methanesulfonic acid and citric acid. Other salts include salts with alkali metals or alkaline earth metals, such as sodium, potassium, calcium or magnesium or with organic bases. The salts can be prepared in situ during the final isolation and purification of the compounds of formula (I), or separately by reacting the free base function with a suitable acid or by reacting the acidic function with a suitable base.

The compounds of the present invention are useful for blocking the interaction of angiotensin II with angiotensin II receptors and for treating hypertension, edema, renal failure, congestive heart failure, glaucoma, psoriasis, benign prostatic hypertrophy, diabetic nephropathy, diabetic retinopathy, or to prevent atherosclerosis or for treating gastrointestinal disorders associated with enhanced contractility and/or motility of intestinal smooth muscle or for treating contractile disorders of the uterus (including premature contractions, dysmenorrhea and the like) or for treating or preventing stroke, cerebral vasospasm or cerebral infarction or for treating CNS disorders (depression, schizophrenia, anxiety or cognitive disorders (Alzheimer's disease, amnesia and senile dementia)) in a human or other mammal. The compounds of the invention are also useful for enhancing intimal wound closure and for reducing luminal thrombogenicity in a human or other mammal.

The ability of the compounds of the invention to block the interaction of angiotensin II with angiotensin II receptors can be demonstrated as described below.

ANGIOTENSIN II FUNCTIONAL ASSAY

Antagonism of Contraction of Rabbit Aorta

The protocol reported by A. T. Chiu and P. Timmermans (P. C. Wong, et al. *Hypertension*, 13, 489–497 (1989)) was followed with a few modifications. Female New Zealand White rabbits weighing 2–5 kg were sedated with carbon dioxide and then sacrificed. Main abdominal aortas were removed and placed in Krebs-Henseleit buffer at room temperature.

| Krebs-Henseleit buffer | |
| --- | --- |
| Buffer Component | mM Concentration |
| sodium chloride | 119.00 |
| potassium chloride | 4.70 |
| potassium dihydrogen phosphate | 1.20 |
| calcium chloride | 2.50 |
| sodium bicarbonate | 20.00 |
| magnesium sulfate | 1.50 |
| dextrose | 11.00 |
| EDTA* disodium calcium salt | 0.01 |

*EDTA = ethylenediamine tetraacetic acid
The buffer contained no cocaine, propanolol or steroid.
The pH of the buffer was 7.40 at 37° C. when saturated with 5% carbon dioxide/95% oxygen.

The tissues were cleaned of extraneous connective tissue, cut into 3 mm rings, and suspended within a 10 mL tissue bath. All dilutions of peptide preparations were made with 0.3% aqueous BSA. The tissues were primed with 55 mM potassium chloride. Tissues were pre-loaded with 1 g of tension. Tension was recorded on a model 7 Grass polygraph using FT03 transducers. At the end of the equilibrium period, a control cumulative concentration-contractile response curve for angiotensin II (A II: $1 \times 10^{-10}$–$10^{-8}$M) was obtained. The tissue was washed several times until the baseline was reached. Forty five minutes later, test compound (antagonist) was added and the tissue was incubated for 30 minutes. The concentration-response curve for A II was then repeated in the presence of the test compound. One dose of antagonist was tested per tissue only. For single dose shift experiments a dose of 1 mM of test compound was used, for a full $pA_2$ experiment multiple doses were used depending upon the potency of the antagonist.

All responses to the control agonist were calculated as a percentage of the maximum response. These points in duplicate were plotted and analyzed according to standard Schild analysis (H. O. Schild, *British J Pharmacology and Chemotherapy*, 2, 189–206 (1947). The $pA_2$ values calculated for the compounds of the invention are shown in Table 1. The $pA_2$ value is the negative logarithm of the $[A]_2$ value. $[A]_2$ is the concentration of antagonist which necessitates doubling the agonist concentration in order to achieve the agonist effect which was measured in the absence of antagonist.

The $pA_2$ value, therefore is a measure of the effectiveness of the compound as an antagonist. The data in Table 1 show that the compounds of the invention are potent antagonists at the angiotensin II receptor.

TABLE 1

| $pA_2$ Values from Isolated Rabbit Aorta Assay | |
| --- | --- |
| Example | $pA_2$ |
| 1 | 6.23 |
| 2 | 6.88 |
| 3 | 7.53 |
| 4H | 9.88 |
| Sar,-1, Thr-8 AII (SARILE) | 9.02 |

The ability of the compounds of the invention to lower blood pressure in vivo in renal artery ligated rats can be demonstrated according to the method disclosed by Cangiano, et al., *J. Pharmacol. Exp. Ther.* 208 310 (1979)).

The total daily dose of the compounds of this invention administered to a human or other mammal in single or in divided doses can be in amounts, for example, from 0.01 to 25 mg/kg body weight or more usually from 0.1 to 15 mg/kg body weight. Single dose compositions can contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose of from 10 mg to 1000 mg.

It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches. The term parenteral as used herein includes subcutaneous injections, intravenous, intramuscular, intrasternal injection, or infusion techniques.

Liquid dosage forms for oral administration can include pharmaceutically acceptable emulsions, microemulsions, solutions, suspensions, syrups and elixirs containing inert diluents commonly used in the art such as water. Such compositions can also comprise adjuvants, such as wetting agents; emulsifying and suspending agents; sweetening, flavoring and perfuming agents.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at ordinary temperature but liquid at the rectal temperature and will therefore melt in the rectum and release the drug.

Solid dosage forms for oral administration can include capsules, tablets, pills, powders, prills and granules. In such solid dosage forms the active compound can be admixed with at least one inert diluent such as sucrose, lactose or starch. Such dosage forms can also comprise, as is normal practice, additional substances other than inert diluents, e.g., tableting lubricants and other tableting aids such as magnesium stearate and microcrystalline cellulose. In the case of capsules, tablets and pills, the dosage forms can also comprise buffering agents. Tablets and pills can additionally be prepared with enteric coatings and other release-controlling coatings.

Solid compositions of a similar type can also be employed as fillers in soft and hard-filled gelatin capsules using such exipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulations, ear drops, eye ointments, powders and solutions are also contemplated as being within the scope of this invention.

The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a-compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

The compounds of the present invention can be administered alone or in combination or in concurrent therapy with other cardiovascular agents independently selected from diuretics, adrenergic blocking agents, vasodilators, calcium channel blockers, angiotensin converting enzyme (ACE) inhibitors, potassium channel activators, antiserotoninergic agents, thromboxane synthetase inhibitors, renin inhibitors and other agents useful for treating (in a human or other mammal) hypertension, edema or congestive heart failure.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof. Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside, flosequinan and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Representative antiserotoninergic agents include ketanserin and the like or a pharmaceutically acceptable salt thereof.

Representative renin inhibitiors include enalkiren, A-72517, PD-134672 or Ro 42-5892 and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compound of formula I and the other cardiovascular agent can be administered at the recommended maximum clinical dosage or at lower doses. Dosage levels of the active compounds in the compositions of the invention can be varied so as to obtain a desired therapeutic response depending on the route of administration, severity of the disease and the response of the patient. The combination can be administered as separate compositions or as a single dosage form containing both agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

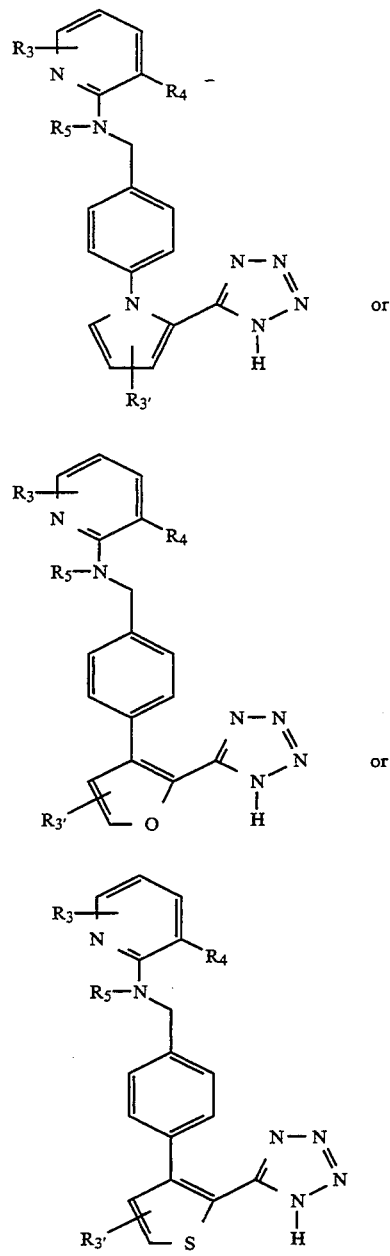

wherein $R_3$ is hydrogen, loweralkyl, halo or alkoxy, $R_{3'}$ is hydrogen, loweralkyl or halo, $R_4$ is —COOR$_{24}$ wherein $R_{24}$ is hydrogen or a carboxy-protecting group selected from the group consisting of $C_1$–$C_8$ alkyl, benzyl, alkoxybenzyl, nitrobenzyl, dialkylaminoalkyl, alkanoyloxyalkyl, aroyloxyalkyl, alkoxycarbonylalkyl, alkoxycarbonyloxyalkyl, alkoxycarbonylaminoalkyl, alkylaminocarbonylaminoalkyl, alkanoylaminoalkyl, dialkylaminocarbonylalkyl, (5-(loweralkyl)-2-oxo-1,3-dioxolen-4-yl)alkyl and (5-phenyl-2-oxo-1,3-dioxolen-4-yl)alkyl and $R_5$ is hydrogen, loweralkyl, alkoxy-substituted loweralkyl, halo-substituted loweralkyl, alkenyl, alkynyl, cycloalkyl or cycloalkylalkyl; or a pharmaceutically acceptable salt thereof.

2. The compound of claim 1 wherein $R_3$ is hydrogen, $R_4$ is —COOH and $R_5$ is loweralkyl.

3. A compound of the formula:

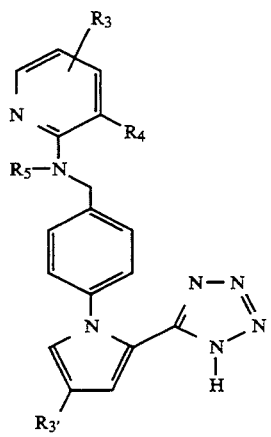

wherein $R_3$ is hydrogen, loweralkyl, halo or alkoxy, $R_{3'}$ is hydrogen, loweralkyl or halo, $R_4$ is —COOR$_{24}$ wherein $R_{24}$ is hydrogen or a carboxy-protecting group selected from the group consisting of $C_1$-$C_8$ alkyl, benzyl, alkoxybenzyl, nitrobenzyl, dialkylaminoalkyl, alkanoyloxyalkyl, aroyloxyalkyl, alkoxycarbonylalkyl, alkoxycarbonyloxyalkyl, alkoxycarbonylaminoalkyl, alkylaminocarbonylaminoalkyl, alkanoylaminoalkyl, dialkylaminocarbonylalkyl, (5-(loweralkyl)-2-oxo-1,3-dioxolen-4-yl)alkyl and (5-phenyl-2-oxo-1,3-dioxolen-4-yl)alkyl and $R_5$ is hydrogen, loweralkyl, alkoxy-substituted loweralkyl, halo-substituted loweralkyl, alkenyl, alkynyl, cycloalkyl or cycloalkylalkyl; or a pharmaceutically acceptable salt thereof.

4. The compound of claim 1 wherein $R_3$ is hydrogen, $R_4$ is —COOH and $R_5$ is loweralkyl.

5. 2-{N-Propyl-N-[(1-[3-bromo-5-(1H-tetrazol-5-yl)pyrrole-1 -yl]phenyl-4-yl)methyl]amino}pyridine-3-carboxylic acid; or a pharmaceutically acceptable salt or prodrug ester thereof wherein the prodrug ester is selected from the group consisting of $C_1$-$C_8$ alkyl, benzyl, alkoxybenzyl, nitrobenzyl, dialkylaminoalkyl, alkanoyloxyalkyl, aroyloxyalkyl, alkoxycarbonylalkyl, alkoxycarbonyloxyalkyl, alkoxycarbonylaminoalkyl, alkylaminocarbonylaminoalkyl, allsanoylaminoallsyl, dialkylaminocarbonylalkyl, (5-(loweralkyl)-2-oxo-1,3-dioxolen-4-yl)alkyl and (5-phenyl-2-oxo-1,3-dioxolen-4-yl)alkyl.

6. A pharmaceutical composition for blocking the interaction of angiotensin II with angiotensin II receptors comprising a pharmaceutically acceptable carrier and a therapeutically effective amount of a compound of claim 1.

7. A method of blocking the interaction of angiotensin II with angiotensin II receptors comprising administering to a human or other mammal in need a therapeutically effective amount of a compound of claim 1.

8. A method of treating hypertension or congestive heart failure comprising administering to a human or other mammal in need a therapeutically effective amount of a compound of claim 1.

* * * * *